(12) United States Patent
Guthrie

(10) Patent No.: US 10,987,333 B2
(45) Date of Patent: *Apr. 27, 2021

(54) METHODS AND COMPOSITIONS FOR PREVENTING AND TREATING AUDITORY DYSFUNCTIONS

(71) Applicant: United States Government as represented by the Department of Veterans Affairs, Washington, DC (US)

(72) Inventor: O'Neil W. Guthrie, Flagstaff, AZ (US)

(73) Assignee: United States Government as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/506,904

(22) Filed: Jul. 9, 2019

(65) Prior Publication Data

US 2020/0069628 A1    Mar. 5, 2020

Related U.S. Application Data

(60) Continuation of application No. 15/854,660, filed on Dec. 26, 2017, now abandoned, which is a division of application No. 15/230,257, filed on Aug. 5, 2016, now Pat. No. 9,889,107, which is a division of application No. 13/907,590, filed on May 31, 2013, now Pat. No. 9,457,009.

(60) Provisional application No. 61/701,397, filed on Sep. 14, 2012, provisional application No. 61/653,577, filed on May 31, 2012.

(51) Int. Cl.
| A61K 31/215 | (2006.01) |
| A61K 31/216 | (2006.01) |
| A61K 31/365 | (2006.01) |
| A61K 45/06 | (2006.01) |
| A61K 36/74 | (2006.01) |

(52) U.S. Cl.
CPC .......... *A61K 31/216* (2013.01); *A61K 31/215* (2013.01); *A61K 31/365* (2013.01); *A61K 36/74* (2013.01); *A61K 45/06* (2013.01)

(58) Field of Classification Search
CPC .................................................. A61K 31/216
See application file for complete search history.

(56) References Cited

U.S. PATENT DOCUMENTS

| 4,872,987 A | 8/1989 | Kopsch |
| 5,401,858 A | 3/1995 | Huynh-Ba |
| 6,039,949 A | 3/2000 | Pero |
| 6,361,805 B2 | 3/2002 | Pero |
| 6,797,286 B2 | 9/2004 | Brobrowski |
| 7,285,293 B2 | 8/2007 | Castillo |
| 7,314,642 B2 | 1/2008 | Castillo et al. |
| 7,579,023 B2 | 8/2009 | Pero |
| 7,595,064 B2 | 9/2009 | Pero |
| 7,947,312 B2 | 5/2011 | Pero |
| 7,955,626 B2 | 6/2011 | Pero |
| 9,457,009 B2 | 10/2016 | Guthrie |
| 9,889,107 B2 | 2/2018 | Guthrie |
| 2013/0324594 A1 | 12/2013 | Guthrie |
| 2016/0338986 A1 | 11/2016 | Guthrie |

FOREIGN PATENT DOCUMENTS

KR    10-2013-0023875    3/2013

OTHER PUBLICATIONS

Dharmananda, Treatment of Tinnitus, Vertigo, and Meniere's Disease with Chinese herbs, Jun. 1998, available at http://www.itmonline.org/arts/tinmen.htm.*
Zeng, Discovery of Quinic Acid Derivatives as Oral Anti-Inflammatory Agents, doctoral dissertation, May 2010, available at https://dc.uthsc.edu/dissertations/314/.*
U.S. Appl. No. 61/653,577, filed May 31, 2012, O'neil W. Guthrie.
U.S. Appl. No. 61/701,397, filed Sep. 14, 2012, O'neil W. Guthrie.
U.S. Appl. No. 13/907,590 (U.S. Pat. No. 9,457,009), filed May 31, 2012 (Oct. 4, 2016), O'neil W. Guthrie.
U.S. Appl. No. 15/230,257 (U.S. Pat. No. 9,889,107), filed Aug. 5, 2015 (Feb. 13, 2018), O'neil W. Guthrie.
U.S. Appl. No. 15/854,660, filed Dec. 26, 2017, O'neil W. Guthrie.
Bors et al. "Protective activity of the *Uncaria tormentosa* extracts on human erythrocytes in oxidative stress induced by 2,4-diclorophenol (2,4-DCP) and catechol," Food and Chemical Toxicology, vol. 49 (2011), pp. 2202-2211.
Dharmananda "Treatment of tinnitus, vertigo, and Meniere's disease with Chinese herbs," Institute of Traditional Medicine, Portland, Oregon, http://www.itmonline.org/arts/tinmen.htm.
Fetoni et al., "Therapeutic window for ferulic acid protection against noise-induced hearing loss in the guinea pig." Acta Oto-Laryngologica, vol. 131, No. 4 (2011), pp. 419-427.
Fetoni et al., "In Vivo protective effect of ferulic acid against noise-induced hearing loss in the guinea-pig," Neuroscience 169 (2010), pp. 1575-1588.
Guthrie et al., "Carboxy alkyl esters of *Uncaria tomentosa* augment recovery of sensorineural functions following noise injury," Brain Research, vol. 1407 (2011), pp. 97-106.

(Continued)

*Primary Examiner* — Svetlana M Ivanova

(74) *Attorney, Agent, or Firm* — Ballard Spahr LLP

(57) ABSTRACT

The invention provides methods for treating auditory impairments in a subject in need of treatment comprising administering to said subject an effective amount of a composition comprising, as an active agent, one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient, so as to treat auditory impairments in the subject.

16 Claims, 13 Drawing Sheets

(56) References Cited

OTHER PUBLICATIONS

Keplinger et al., "*Uncaria tomentosa* (Willd.) DC.—Ethnomedicinal use and new pharmacological, toxicological and botanical results," *Journal of Ethnopharmacology*, No. 64, 1999, pp. 23-34.

Pero, "Historical development of *Uncaria* preparations and their related bioactive components," DNA Damage Repair, Repair Mechanisms and Aging, 2010, pp. 223-226.

Sandoval et al. Anti-inflammatory and antioxidant activities of cat's claw (*Uncaria* tomentosa and *Uncaria* guianensis) are independent of their alkaloid content, Phytomedicine, No. 9, 2002, pp. 325-337.

Kaathu Iraichalukku Ennai-6, Key Attributes of TKDL.

"Age-related changed in DNA repair illuminate the connection between age and genetic damages," Science Daily, Oct. 24, 2006, http://www.sciencedaily.com/releases/2006/10/061024010423.htm.

Requirement for Restriction issued on Mar. 30, 2015 by the USPTO for U.S. Appl. No. 13/907,590, filed May 31, 2013 now U.S. Pat. No. 9,457,009 on Oct. 4, 2016 (Inventor—O'neil W. Guthrie) (9 Pages).

Response to Requirement for Restriction filed on May 27, 2015 with the USPTO for U.S. Appl. No. 13/907,590, filed May 31, 2013 now U.S. Pat. No. 9,457,009 on Oct. 4, 2016 (Inventor—O'neil W. Guthrie) (12 Pages).

Non-final Office Action issued on Jul. 13, 2015 by the USPTO for U.S. Appl. No. 13/907,590, filed May 31, 2013 now U.S. Pat. No. 9,457,009 on Oct. 4, 2016 (Inventor—O'neil W. Guthrie) (19 Pages).

Response to Office Action filed on Nov. 13, 2015 with the USPTO for U.S. Appl. No. 13/907,590, filed May 31, 2013 now U.S. Pat. No. 9,457,009 on Oct. 4, 2016 (Inventor—O'neil W. Guthrie) (43 Pages).

Final Office Action dated Dec. 22, 2015 by the USPTO for U.S. Appl. No. 13/907,590, filed May 31, 2013 now U.S. Pat. No. 9,457,009 on Oct. 4, 2016 (Inventor—O'neil W. Guthrie) (13 Pages).

Response to Office Action filed on Apr. 14, 2016 with the USPTO for U.S. Appl. No. 13/907,590, filed May 31, 2013 now U.S. Pat. No. 9,457,009 on Oct. 4, 2016 (Inventor—O'neil W. Guthrie) (58 Pages).

Notice of Allowance dated May 2, 2016 by the USPTO for U.S. Appl. No. 13/907,590, filed May 31, 2013 now U.S. Pat. No. 9,457,009 on Oct. 4, 2016 (Inventor—O'neil W. Guthrie) (7 Pages).

Requirement for Restriction dated Jun. 23, 2017 by the USPTO for U.S. Appl. No. 15/230,257, filed Aug. 5, 2016 now U.S. Pat. No. 9,889,107 on Feb. 13, 2018 (Inventor—O'neil W. Guthrie) (8 Pages).

Response to Requirement for Restriction filed on Aug. 22, 2017 with the USPTO for U.S. Appl. No. 15/230,257, filed Aug. 5, 2016 now U.S. Pat. No. 9,889,107 on Feb. 13, 2018 (Inventor—O'neil W. Guthrie) (9 Pages).

Supplemental Amendment filed on Sep. 18, 2017 with the USPTO for U.S. Appl. No. 15/230,257, filed Aug. 5, 2016 now U.S. Pat. No. 9,889,107 on Feb. 13, 2018 (Inventor—O'neil W. Guthrie) (7 Pages).

Notice of Allowance dated Oct. 3, 2017 by the USPTO for U.S. Appl. No. 15/230,257, filed Aug. 5, 2016 now U.S. Pat. No. 9,889,107 on Feb. 13, 2018 (Inventor—O'neil W. Guthrie) (8 Pages).

Requirement for Restriction dated Jun. 8, 2018 by the USPTO for U.S. Appl. No. 15/854,660, filed Dec. 26, 2017 (Inventor—O'neil W. Guthrie) (5 Pages).

Response to Requirement for Restriction filed on Aug. 8, 2018 with the USPTO for U.S. Appl. No. 15/854,660, filed Dec. 26, 2017 (Inventor—O'neil W. Guthrie) (5 Pages).

Non-final Office Action dated Aug. 23, 2018 by the USPTO for U.S. Appl. No. 15/854,660, filed Dec. 26, 2017 (Inventor—O'neil W. Guthrie) (12 Pages).

Response to Office Action filed on Sep. 28, 2018 with the USPTO for U.S. Appl. No. 15/854,660, filed Dec. 26, 2017 (Inventor—O'neil W. Guthrie) (15 Pages).

Final Office Action dated Nov. 14, 2018 by the USPTO for U.S. Appl. No. 15/854,660, filed Dec. 26, 2017 (Inventor—O'neil W. Guthrie) (13 Pages).

\* cited by examiner

METHODS AND COMPOSITIONS FOR PREVENTING AND TREATING AUDITORY DYSFUNCTIONS

This Application is a Continuation of U.S. application Ser. No. 15/854,660, filed on Dec. 26, 2017, which is a Division of U.S. application Ser. No. 15/230,257, filed Aug. 5, 2016, now issued as U.S. Pat. No. 9,889,107, which is a Division of U.S. application Ser. No. 13/907,590, filed May 31, 2013, now issued as U.S. Pat. No. 9,457,009, which claims the benefit of U.S. Provisional Application No. 61/653,577, filed May 31, 2012, and U.S. Provisional Application No. 61/701,397, filed Sep. 14, 2012, the contents of all of which are herein incorporated by reference in their entireties.

Throughout this application various publications are referenced. The disclosures of these publications in their entireties are hereby incorporated by reference into this application in order to more fully describe the state of the art to which this invention pertains.

FIELD OF THE INVENTION

This invention relates to auditory dysfunctions (e.g., hearing loss, tinnitus, hyperacusis, and related auditory processing disorders) and methods of preventing and treating such dysfunctions. Additionally, this invention relates to specific chemicals and chemical compositions and the uses of such chemicals and chemical compositions for preventing and/or treating auditory dysfunctions.

BACKGROUND OF THE INVENTION

Auditory dysfunction in people is an ongoing problem in the medical fields of otology and audiology. Auditory dysfunctions typically arise from both acute and chronic exposures to loud sounds, ototoxic chemicals and aging. Sounds exceeding 85 decibels can cause hearing loss and is generated by sound sources such as, gun shots, exploding bombs, jet engines, power tools, and musical concerts. Other common everyday activities and products also give rise to high intensity noise such as use of hair dryers, MP3 players, lawn mowers, and blenders. Military personnel are particularly at risk for noise induced hearing loss due to typical military noise exposures. Side effects to noise induced hearing loss include tinnitus (ringing in the ears), diminished speech understanding, hyperacusis, recruitment and various types of auditory processing impairments. Exposures to commonly used medications may also induce auditory dysfunctions. For instance, patients treated with anticancer therapies, antibiotics and other medications often develop hearing loss as a side effect. Furthermore, exposure to industrial chemicals and gasses may induce auditory impairments. Lastly, auditory dysfunction is a common consequence of aging in Western societies.

Approximately 17 percent of Americans (estimated at 36 million) have hearing loss and half of that number are under the age of 65. It is predicted that the number of Americans with hearing loss will exceed 70 million by the year 2030.

About 300 million people worldwide currently suffer from moderate to severe hearing loss, and this number is expected to increase to 700 million by the year 2015. Most of these people will suffer from noise induced hearing loss and one in four Americans will develop permanent hearing loss as a result of occupational exposure to noise hazards. According to the Center for Commercialization of Advanced Technology, the Department of Defense and the VA, the VA spends over $1 billion on hearing loss compensation. The Navy, Marine Corps, and Air Force (combined) file 22,000 new hearing loss claims, and hearing loss costs the economy more than $56 billion per year.

Very few cases of hearing loss can actually be cured. Audiological devices such as hearing aids have limitations including the inability to improve speech intelligibility. Of those impacted by hearing impairments, less than 20 percent presently use hearing instruments.

In cases of age-related, noise- or drug-induced auditory dysfunctions, the only effective way to currently "treat" the disorder or reduce its severity is prevention: avoiding excessive noise and using ear protectors, practicing a healthy lifestyle, and avoiding exposure to ototoxic drugs and substances if possible.

Once the hearing loss has developed, people may use a hearing aid to correct the inability to hear. However, despite advances in the performance of these prostheses, they still have their limits. For example, hearing aids mainly amplify sound and cannot correct for suprathreshold or retrocochlear impairments such as impaired speech intelligibility, speech in noise deficits, tinnitus, hyperacusis, loudness recruitment and various other types of central auditory processing disorders. Hearing aids essentially amplify sounds which stimulate unimpaired cells but there is no therapy for aiding recovery of impaired cells or maximizing the function of existing unimpaired cells. In cases of complete or profound deafness, a cochlear implant may be used. This device transmits electrical stimuli via electrodes surgically implanted into the cochlea. A cochlear implant can be of particular help for deaf children if it is implanted around the age of two or three, the time when language skills are developing fastest. However, cochlear implants involve invasive surgery and are expensive. Furthermore, cochlear implants require viable neurons in order to achieve benefit.

Thus, there remains a long felt need to protect auditory cells before injury and preserve/promote the function of existing cells after injury. As disclosed below, the present invention provides a novel means for preventing and treating auditory dysfunctions.

SUMMARY OF THE INVENTION

The invention provides methods for treating auditory impairments in a subject in need of treatment comprising administering to said subject an effective amount of a composition comprising, as an active agent, one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient, so as to treat auditory impairments in the subject.

In one embodiment, the invention provides methods for treating auditory impairments in a subject comprising administering to said subject an effective amount of a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient, so as to treat auditory impairments in the subject.

In another embodiment, the invention provides methods for inhibiting cochlear inflammation in a subject comprising administering to said subject an effective amount of a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient, thereby inhibiting cochlear inflammation in the subject.

In another embodiment, the invention provides methods for inhibiting cochlear inflammation in a subject comprising administering to said subject an effective amount of a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient, thereby inhibiting cochlear inflammation in the subject.

In one embodiment, the invention provides for methods for inhibiting the loss or death of the cells of the auditory system in a subject comprising administering to said subject an effective amount of a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient, thereby inhibiting loss or death of the cells of the auditory system in the subject.

In another embodiment, the invention provides methods for inhibiting the loss or death of the cells of the auditory system in a subject comprising administering to said subject an effective amount of a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient, thereby inhibiting loss or death of the cells of the auditory system in the subject.

In a further embodiment, the invention provides methods for maintaining or promoting the growth of cells of the auditory system in a subject comprising administering to said subject a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient in an effective amount so as to augment endogenous DNA repair, thereby maintaining or promoting the growth of cells of the auditory system in the subject.

In another embodiment, the invention provides methods for maintaining or promoting the growth of cells of the auditory system in a subject comprising administering to said subject a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient in an effective amount so as to augment endogenous DNA repair, thereby maintaining or promoting the growth of cells of the auditory system in the subject.

In another embodiment, the invention provides methods for inhibiting or reversing ion dyshomeostasis, mitochondriopathy, energy catastrophe and/or the proliferation of free radicals in the auditory system in a subject comprising administering to said subject an effective amount of a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient in an effective amount so as to maintain the viability or growth of auditory nerve cells or cochlear cells, thereby inhibiting or reversing ion dyshomeostasis, mitochondriopathy, energy catastrophe and/or the proliferation of free radicals in the auditory system.

In another embodiment, the invention provides methods for inhibiting or reversing ion dyshomeostasis, mitochondriopathy, energy catastrophe and/or the proliferation of free radicals in the auditory system in a subject comprising administering to said subject an effective amount of a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient in an effective amount so as to maintain the viability or growth of auditory nerve cells or cochlear cells, thereby inhibiting or reversing ion dyshomeostasis, mitochondriopathy, energy catastrophe and/or the proliferation of free radicals in the auditory system.

The invention also provides pharmaceutical formulations comprising any one or more of a carboxy alkyl ester, a quinic acid derivative, a caffeic acid derivative, a ferulic acid derivative, or a quinic acid lactone or a derivative thereof or pharmaceutically acceptable salt and pharmaceutically acceptable excipients.

The invention also provides pharmaceutical formulations comprising any one or more of a carboxy alkyl ester, pentacyclic alkaloid, tannin, or phytochemical derived from the inner bark or root of *Uncaria tomentosa* or a derivative thereof or pharmaceutically acceptable salt thereof and pharmaceutically acceptable excipients.

BRIEF DESCRIPTION OF THE FIGURES

The figures show that gastric gavage of laboratory rats with a formulation of the agents result in almost complete recovery from noise induced hearing loss. The noise induced hearing loss was induced with a damaging noise dose that exceeds the permissible doses for work-place safety in the United States. Note that both sensory and neural functions were preserved due to treatment with the agent. Additionally, the number of dead/missing auditory cells was reduced in the group that was treated with the agent and the noise while the group that received only the noise dose showed significant cellular loss.

The continuous gray lines in each panel represent baseline recordings and the broken gray lines are the noise floor. Errors bars are standard errors of the means.

Figure 17:
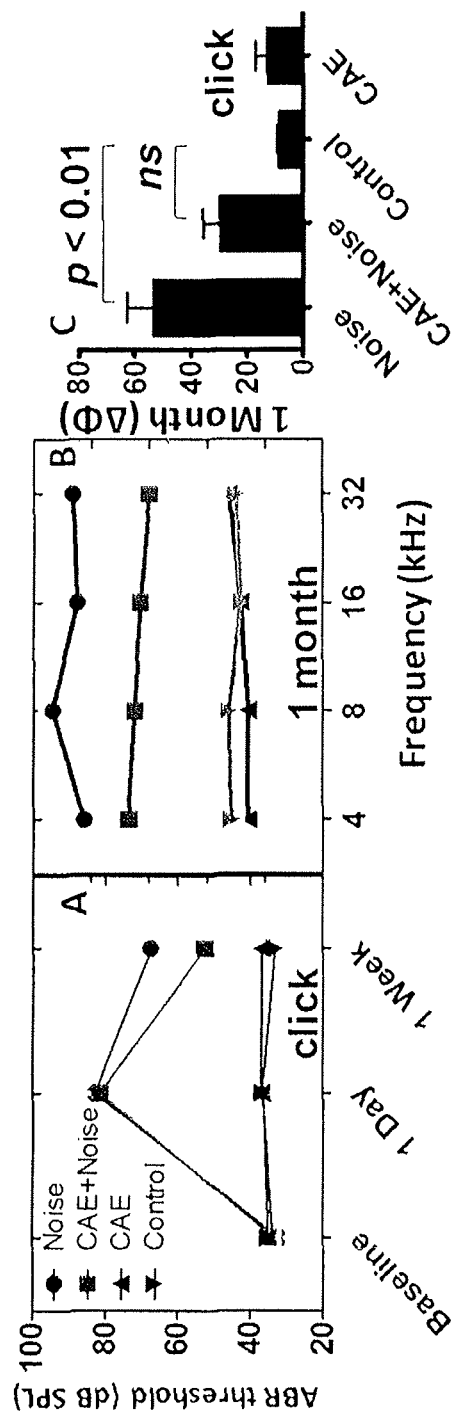

FIG. 17. Preliminary data showing that seven days of CAE treatment starting at 1 day after noise exposure resulted in accelerated recovery of auditory sensitivity (threshold) as determined by auditory brainstem response (ABR). Panel A (short term study; CAE 160 mg/kg/7 days) reveals that both the noise and CAE+noise groups exhibited the same level of loss at 1 day after the noise injury however, the CAE+noise groups showed significantly (ANOVA main effects of groups: $p<0.05$) faster recover at just 1 week after the noise exposure. Panel B (long term study; CAE 160 mg/kg/28 days) shows frequency specific thresholds at 1 month after the noise exposure. Note that the thresholds for the CAE+noise group is significantly (ANOVA main effects of groups: $p<0.05$) better (lower) than that of the noise-only group. Panel C (long term study; CAE 160 mg/kg/28 days) shows that at 1 month after noise exposure, the threshold shift ($\Delta\Phi$: relative to baseline) for the CAE+noise group is not significantly different (ns) from that of control. However, the noise-only group exhibited significant threshold shift compared to that of control. Each plot/bar represents mean±SEM for N=6 or 8 rats.

DETAILED DESCRIPTION OF THE INVENTION

Definitions. Before describing the invention in detail, several terms used in the context of the present invention will be defined. In addition to these terms, others are defined elsewhere in the specification as necessary. Unless otherwise expressly defined herein, terms of art used in this specification will have their art-recognized meanings.

Other features and advantages of the invention will be apparent from the following drawings, detailed description, and appended claims.

An "agent" or "active agent" refers to an active ingredient delivered to achieve an intended protective or therapeutic benefit. As used herein, an active agent can be any one or more of the following chemicals; phenylpropanoids, carboxy alkyl esters, alkaloids, pentacyclic alkaloids, tannins, phytochemicals, chlorogenic acids, quinic acid esters and quinic acids, and derivatives thereof and pharmaceutically acceptable salts thereof.

The term "combination therapy" refers to a therapeutic regimen that involves at least two of the agents. For example, a combination therapy may involve the administration of a chlorogenic acid and a quinic acid. Alternatively, a combination therapy may involve the administration of one or more agent in conjunction with another therapeutic chemical, compound or device. In the context of the administration of two or more chemically distinct agents, it is understood that the active ingredients may be administered as part of the same composition or as different compositions. When administered as separate compositions, the compositions comprising the different active ingredients may be administered at the same or different times, by the same or different routes, using the same or different dosing regimens, all as the particular context requires. Similarly, when one or more agents are combined with other drugs, the drug(s) may be delivered before, during, and/or after the period the subject or person is in therapy.

In the context of this invention, a "liquid composition" refers to one that, in its filled and finished form as provided from a manufacturer to an end user (e.g., a doctor, nurse, or patient), is a liquid or solution, as opposed to a solid. Here, "solid" refers to compositions that are not liquids or solutions. For example, such solids include dried compositions prepared by filtering, lyophilization, freeze-drying, precipitation, drying and similar procedures.

"Monotherapy" refers to a treatment regimen based on the delivery of one therapeutically effective composition of the gents, whether administered as a single dose or several doses over time.

A "plurality" means more than one.

The term "species" when used in the context of describing a particular drug species, refers to a population of chemically indistinct molecules.

A "subject" or "patient" refers to an animal in need of treatment that can be effected by molecules of the invention. Animals that can be treated in accordance with the invention include vertebrates, with mammals such as bovine, canine, equine, feline, ovine, porcine, murine and primate (including humans and non-human primates) animals being particularly preferred examples. Subjects in need of treatment include those with auditory dysfunctions (e.g., hearing loss, tinnitus, hyperacusis, and related auditory processing disorders) and subject that have a familial history of hearing impairments or auditory dysfunctions.

DP-grams as referred to herein are graphs of distortion product otoacoustic emissions.

Gavage, as used herein refers to supplying a nutritional substance into the stomach.

The term "pharmaceutically acceptable salt" refers to salts which retain the biological effectiveness and properties of the agents, and which are not biologically or otherwise undesirable. In many cases, the agents of this invention are capable of forming acid and/or base salts by virtue of the presence of amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts, see, e.g., Berge, et al. (*J. Pharm. Sci.*, vol. 66, 1 (1977)).

The expression "non-toxic pharmaceutically acceptable salts" refer to non-toxic salts formed with nontoxic, pharmaceutically acceptable inorganic or organic acids or inorganic or organic bases. For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicylic, sulfanilic, fumaric, methanesulfonic, trifluoromethanesulfonic, and toluenesulfonic acid and the like. Salts also include those from inorganic bases, such as ammonia, sodium hydroxide, potassium hydroxide, and hydrazine. Suitable organic bases include methylamine, ethylamine, propylamine, dimethylamine, diethylamine, diethanolamine, trimethylamine, triethylamine, triethanolamine, ethylenediamine, hydroxyethylamine, morpholine, piperazine, and guanidine, as the case may be as use of such salts are amenable to the agents.

The term "effective amount" of a compound (or composition of the invention, or the like) means an amount that is effective to exhibit the desired biological activity or achieve the desired clinical result in a subject response to the particular treatment, commensurate with a reasonable benefit/risk ratio when used in the manner of this invention.

A "therapeutically effective amount" refers to an amount of an active ingredient sufficient to effect treatment when administered to a subject in need of such treatment. In the context of auditory treatment, a "therapeutically effective amount" is one that produces an objective response in evaluable patients. Such responses include changes in one or more parameters associated with auditory function and structure. The therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy.

The term "treatment" or "treating" means any treatment of a disease or disorder, including preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "protection" thus includes "prophylaxis".

The present invention also includes derivatives of the compounds of the invention, including structural analogues, compounds derived from compounds of the invention, prodrug, polymorph forms, metabolites, heat-transformed chemical products, and pharmaceutically acceptable salts, and combinations thereof.

The present invention also includes other forms of the compounds of the invention, including prodrug and polymorph forms. Here, a "prodrug" is a compound that contains one or more functional groups that can be removed or modified in vivo to result in a molecule that can exhibit therapeutic utility in vivo. A "polymorph" refers to a compound that has an identical chemical composition (i.e., it is of the same compound species) as compared to another compound but that differs in crystal structure. In preferred embodiments, the agents, could be removed or modified in vivo or comprise the same composition as other natural or synthetic compounds but differing in specific structure.

Methods of the Invention

The invention provides methods of treating auditory impairments in a subject, e.g., a subject suffering from or experiencing an auditory impairment, cochlear inflammation, permanent sensorineural hearing loss, tinnitus, loudness recruitment, hyperacusis, diplacusis or speech intelligibility deficits. In one embodiment, the method comprises administering to said subject an effective amount of any of the compositions of the invention (e.g., a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient) so as to treat an auditory impairment in the subject. In another embodiment, the method comprises administering to the subject one or more of a purified or isolated carboxy alkyl ester, purified or isolated quinic acid or derivative, purified or isolated caffeic acid or derivative, a purified or isolated ferulic acid or derivative, or a purified or isolated quinic acid lactone or derivative thereof or a pharmaceutically acceptable salt thereof in a sufficient amount so as to treat the auditory impairment. The active agents of the invention may be included in one or more nutraceutical compositions, such as nutritional and/or dietary supplements.

In a further embodiment of the invention, the method comprises administering to said subject an effective amount of a composition comprising, as an active agent, one or more of a carboxy alkyl ester, alkaloid, pentacyclic alkaloid, tannin, or phytochemical derived from the inner bark or root of Uncaria tomentosa or derivative thereof or pharmaceutically acceptable salt thereof and an acceptable carrier or excipient so as to treat auditory impairments in the subject. In yet another embodiment, the active agent is a purified or isolated carboxy alkyl ester, alkaloid, pentacyclic alkaloid, tannin, or phytochemical derived from the inner bark, leaves or root of Uncaria tomentosa and other plants. For example, the active agents may be found in extracts or extracted from Uncaria tomentosa and used as nutraceuticals or as pharmaceuticals. Nutraceutical includes a composition that may have healthful effects in a subject upon administration, wherein the composition is, for example, available to a subject without a doctor's prescription.

In one embodiment, the carboxy alkyl ester may be any of (1) 3,4-O-dicaffeoylquinic acid; (2) 3,5-O-dicaffeoylquinic acid (CAS Registry Number: 2450-53-5); (3) 1,3-O-dicaffeoylquinic acid (CAS Registry Number: 19870-46-3); (4) 4,5-O-dicaffeoylquinic acid (CAS Registry Number: 32451-88-0); (5) 1,5-O-dicaffeoylquinic acid (CAS Registry Number: 19870-46-3); (6) 3-O-feruloylquinic acid; (7) 4-O-feruloylquinic acid; (8) 5-O-feruloylquinic acid; (9) 1-O-caffeoylquinic acid; (10) 3-O-caffeoylquinic acid; (11) 4-O-caffeoylquinic acid; (12) 5-O-caffeoylquinic acid; (13) (1S,3R,4R,5R)-3-[3-(3,4-dihydroxyphenyl)-3R-hydroxypropanoyl] 1,4,5-trihydroxycyclohexanecarboxylic acid; (14) (1 S,3R,4R,5R)-3-[3-(3,4 dihydroxyphenyl)-3S-hydroxypropanoyl]-1,4,5-trihydroxycyclohexanecarboxylic acid; (15) (1 S,3R,4R,5R)-5-[3-(3,4-dihydroxyphenyl)-3R-hydroxypropanoyl]-1,3,4-trihydroxycyclohexanecarboxylic acid; (16) (1S,3R,4R,5R)-5-[3-(3,4-dihydroxyphenyl)-3S-hydroxypropanoyl]-1,3,4-trihydroxycyclohexanecarboxylic acid; (17) (1 S,3R,4R,5R)-4-[3-(3,4-dihydroxyphenyl)-3R-hydroxypropanoyl]-1,3,5-trihydroxycyclohexanecarboxylic acid; (18) (1 S,3R,4R,5R)-4-[3-(3,4-dihydroxyphenyl)-3S-hydroxypropanoyl]-1,3,5-trihydroxycyclohexanecarboxylic acid; (19) cis-5-O-caffeoylquinic acid; (20) 3-O-caffeoylquinic acid lactone; (21) 3-O-caffeoyl-4-O-feruloylquinic acid; and (22) other quinic acid esters, and pharmaceutically acceptable salt thereof. The carboxy alkyl esters may be included in one or more nutraceutical compositions, such as nutritional and/or dietary supplements.

Merely by way of example, the active agents may also be found in a nutritional supplement formerly referred to as C-Med-100 and now commonly referred to as AC-11 (sold, for example, by Activar Company, Onnit Labs, Solgar Company, Sotrue Company, Optigenex Company and Ceregenex Company).

In one embodiment, the composition of the invention further comprises any one or more of an alkaloid, pentacyclic alkaloid, tannin, or a phytochemical of Uncaria *tomentosa* or derivative thereof or pharmaceutically acceptable salt thereof.

In another embodiment, the composition may be an aqueous extract from said bark, other plants or plant parts or synthetic derivatives. Some extracts according to the invention may also be provided to a subject as nutraceuticals, for example, as adjuvants in the treatment of a variety of condition including, but not limited to, auditory dysfunctions (e.g., hearing loss, tinnitus, hyperacusis, and related auditory processing disorders).

In one embodiment, the composition may be formulated for administration selected from the group consisting of auricular, oral, parenteral, intraperitoneal, local, buccal, nasal, and topical administration.

In another embodiment, the composition may be in the form of a liquid, tablet or capsule.

In another embodiment, the hearing impairment may be hearing loss or deafness. For example, a subject is hearing impaired when the subject's audiogram shows hearing thresholds greater than 25 dB HL at any frequency or the subject exhibits difficulty understanding speech with or without the presence of background noise.

In another embodiment, administration of the composition may be effected during or after an insult that can damage the auditory system.

Examples of auditory impairments may include but not limited to permanent sensorineural hearing loss, tinnitus, loudness recruitment, hyperacusis, diplacusis and speech intelligibility deficits.

The invention also provides methods for inhibiting cochlear inflammation in a subject suffering cochlear inflammation. In one embodiment, the method comprises administering to said subject an effective amount of any of the compositions of the invention (e.g., a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient) so as to inhibit cochlear inflammation in the subject. In another embodiment, the method comprises administering to the subject one or more of a purified or isolated carboxy alkyl ester, purified or isolated quinic acid or derivative, purified or isolated caffeic acid or derivative, a ferulic acid or derivative, or a quinic acid lactone or derivative thereof or a pharmaceutically acceptable salt thereof in a sufficient amount so as to inhibit cochlear inflammation.

In a further embodiment of the invention, the method comprises administering to said subject an effective amount of a composition comprising as an active agent one or more of a carboxy alkyl ester, alkaloid, pentacyclic alkaloid, tannin, or phytochemical derived from the inner bark or root of Uncaria *tomentosa* or derivative thereof or pharmaceutically acceptable salt thereof and an acceptable carrier or excipient so as to inhibit cochlear inflammation in the subject. In yet another embodiment, the method comprises administering to the subject one or more of a purified or isolated carboxy alkyl ester, alkaloid, pentacyclic alkaloid, tannin, or phytochemical derived from the inner bark or root of Uncaria *tomentosa* or derivative thereof or pharmaceutically acceptable salt thereof in a sufficient amount so as to inhibit cochlear inflammation.

In one embodiment, the method of the invention inhibits hearing loss in a subject by inhibiting cochlear inflammation.

In one embodiment, the composition further comprises any one or more of an alkaloid, pentacyclic alkaloid, tannin, or a phytochemical of Uncaria *tomentosa* or derivative thereof or pharmaceutically acceptable salt thereof.

The invention also provides a method of inhibiting the loss or death of the cells of the auditory system in a subject, e.g., a subject suffering from or experiencing an auditory impairment, cochlear inflammation, permanent sensorineural hearing loss, tinnitus, loudness recruitment, hyperacusis, diplacusis or speech intelligibility deficits.

In one embodiment, the method comprises administering to said subject an effective amount of any of the compositions of the invention (e.g., a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient) so as to inhibit the loss or death of the cells of the auditory system in the subject. In another embodiment, the method comprises administering to the subject one or more of a purified or isolated carboxy alkyl ester, purified or isolated quinic acid or derivative, purified or isolated caffeic acid or derivative, a ferulic acid or derivative, or a quinic acid lactone or derivative thereof or a pharmaceutically acceptable salt thereof in a sufficient amount so as to inhibit the loss or death of the cells of the auditory system.

In a further embodiment of the invention, the method comprises administering to said subject an effective amount of a composition comprising as an active agent one or more of a carboxy alkyl ester, alkaloid, pentacyclic alkaloid, tannin, or phytochemical derived from the inner bark or root of Uncaria *tomentosa* or derivative thereof or pharmaceutically acceptable salt thereof and an acceptable carrier or excipient so as to inhibit the loss or death of the cells of the auditory system in the subject. In yet another embodiment, the method comprises administering to the subject one or more of a purified or isolated carboxy alkyl ester, alkaloid, pentacyclic alkaloid, tannin, or phytochemical derived from the inner bark or root of Uncaria *tomentosa* or derivative thereof or pharmaceutically acceptable salt thereof in a sufficient amount so as to inhibit the loss or death of the cells of the auditory system.

In one embodiment, the method of the invention inhibits hearing loss in a subject by inhibiting the loss or death of the cells of the auditory system.

In another embodiment, administration of the composition may be effected prior to an insult that can damage the auditory system.

In another embodiment, the composition may be administered prophylactically over a period of days, weeks, or months.

The invention also provides a method of maintaining or promoting the growth of cells of the auditory system of a subject.

In one embodiment, the method comprises administering to said subject an effective amount of any of the compositions of the invention (e.g., a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient) so as to maintain or promote the growth of cells of the auditory system in the subject. In another embodiment, the method comprises administering to the subject one or more of a purified or isolated carboxy alkyl ester, purified or isolated quinic acid or derivative, purified or isolated caffeic acid or derivative, a ferulic acid or derivative, or a quinic acid lactone or derivative thereof or a pharmaceutically acceptable salt thereof in a sufficient amount so as to maintain or promote the growth of cells of the auditory system.

In a further embodiment of the invention, the method comprises administering to said subject an effective amount of a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient so as to maintain or promote the growth of cells of the auditory system in the subject. In yet another embodiment, the method comprises administering to the subject one or more of a purified or isolated carboxy alkyl ester, alkaloid, pentacyclic alkaloid, tannin, or phytochemical derived from the inner bark or root of *Uncaria tomentosa* or derivative thereof or pharmaceutically acceptable salt thereof in a sufficient amount so as to maintain or promote the growth of cells of the auditory system.

In one embodiment, the method of the invention inhibits hearing loss in a subject by maintaining or promoting the growth of cells of the auditory system of the subject.

The invention also provides a method of inhibiting or reversing ion dyshomeostasis, mitochondriopathy, energy catastrophe and/or the proliferation of free radicals in the auditory system of a subject.

In one embodiment, the method comprises administering to said subject an effective amount of any of the compositions of the invention (e.g., a composition comprising as an active agent one or more of a carboxy alkyl ester, a quinic acid derivative, a caffeic acid derivative, a ferulic acid derivative, or a quinic acid lactone or derivative thereof or pharmaceutically acceptable salt thereof and an acceptable carrier or excipient) so as to inhibit or reverse ion dyshomeostasis, mitochondriopathy, energy catastrophe and/or the proliferation of free radicals in the auditory system in the subject. In another embodiment, the method comprises administering to the subject one or more of a purified or isolated carboxy alkyl ester, purified or isolated quinic acid or derivative, purified or isolated caffeic acid or derivative, a ferulic acid or derivative, or a quinic acid lactone or derivative thereof or a pharmaceutically acceptable salt thereof in a sufficient amount so as to inhibit or reverse ion dyshomeostasis, mitochondriopathy, energy catastrophe and/or the proliferation of free radicals in the auditory system.

In a further embodiment of the invention, the method comprises administering to said subject an effective amount of a composition comprising as an active agent one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof and an acceptable carrier or excipient so as to inhibit or reverse ion dyshomeostasis, mitochondriopathy, energy catastrophe and/or the proliferation of free radicals in the auditory system in the subject. In yet another embodiment, the method comprises administering to the subject one or more of a purified or isolated carboxy alkyl ester, alkaloid, pentacyclic alkaloid, tannin, or phytochemical derived from the inner bark or root of *Uncaria tomentosa* or derivative thereof or pharmaceutically acceptable salt thereof in a sufficient amount so as to inhibit or reverse ion dyshomeostasis, mitochondriopathy, energy catastrophe and/or the proliferation of free radicals in the auditory system.

Compositions of the Invention

This invention also concerns treatment compositions for use in treating or inhibiting auditory dysfunctions (e.g., hearing loss, tinnitus, hyperacusis, and related auditory processing disorders), particularly nutraceutical, pharmaceutical or veterinary compositions, comprising the agent formulated together with one or more non-toxic acceptable carriers, preferably pharmaceutically acceptable carriers. The terms "pharmaceutically acceptable carrier" and "physiologically acceptable carrier" refer to molecular entities and compositions that are physiologically tolerable and do not typically produce an unintended allergic or similar untoward reaction, such as gastric upset, dizziness and the like, when administered to a subject. In the context of therapeutic compositions intended for human administration, pharmaceutically acceptable carriers are used. The agents may be processed in accordance with conventional methods of pharmaceutical compounding techniques to produce medicinal agents (i.e., medicaments or therapeutic compositions) for administration to subjects, including humans and other mammals, i.e., "pharmaceutical" and "veterinary" administration, respectively. See, for example, the latest edition of Remington's Pharmaceutical Sciences (Mack Publishing Co., Easton, Pa.). Typically, a composition such as one or more of the agents are combined as a composition with a pharmaceutically acceptable carrier. The composition(s) may also include one or more of the following: excipients; preserving agents; solubilizing agents; stabilizing agents; wetting agents; emulsifiers; sweeteners; colorants; odorants; salts; buffers; coating agents; and antioxidants.

The present invention provides pharmaceutical formulations for use in treating or inhibiting auditory dysfunctions (e.g., hearing loss, tinnitus, hyperacusis, and related auditory processing disorders), (also known as pharmaceutical compositions or dosage forms) comprising as its only active agent, one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof, and a pharmaceutically acceptable carrier or vehicle. In another embodiment, the active agent may be one or more of a carboxy alkyl ester, quinic acid or derivative, caffeic acid or derivative, a ferulic acid or derivative, or a quinic acid lactone or derivative thereof or a pharmaceutically acceptable salt thereof. In an embodiment of the invention, no other active agents except any one or more of those listed supra (or its specific embodiments listed infra) are included in the pharmaceutical formulation.

Further, the present invention also provides pharmaceutical formulations for use in treating or inhibiting auditory dysfunctions (e.g., hearing loss, tinnitus, hyperacusis, and related auditory processing disorders), (also known as pharmaceutical compositions or dosage forms) consisting of as the active agent(s), one or more of a carboxy alkyl ester, alkaloid, pentacyclic alkaloid, tannin, or phytochemical derived from the inner bark or root of *Uncaria tomentosa* or derivative thereof or pharmaceutically acceptable salt thereof, and pharmaceutically acceptable carrier(s) or vehicle(s). In another embodiment, the pharmaceutical formulation consists of an active agent(s), which is one or more of a carboxy alkyl ester, quinic acid or derivative, caffeic acid or derivative, a ferulic acid or derivative, or a quinic acid lactone or derivative thereof or a pharmaceutically acceptable salt thereof. In an embodiment of the invention, no other active agents except those listed supra (or its specific embodiments listed infra) are included in the pharmaceutical formulation.

Suitable examples of carboxy alkyl esters include, but are not limited to, any of (1) 3,4-O-dicaffeoylquinic acid; (2) 3,5-O-dicaffeoylquinic acid (CAS Registry Number: 2450-53-5); (3) 1,3-O-dicaffeoylquinic acid (CAS Registry Number: 19870-46-3); (4) 4,5-O-dicaffeoylquinic acid (CAS Registry Number: 32451-88-0); (5) 1,5-O-dicaffeoylquinic acid (CAS Registry Number: 19870-46-3); (6) 3-O-feruloylquinic acid; (7) 4-O-feruloylquinic acid; (8) 5-O-feruloylquinic acid; (9) 1-O-caffeoylquinic acid; (10) 3-O-caffeoylquinic acid; (11) 4-O-caffeoylquinic acid; (12) 5-O-caffeoylquinic acid; (13) (1S,3R,4R,5R)-3-[3-(3,4-dihydroxyphenyl)-3R-hydroxypropanoyl] 1,4,5-trihydroxycyclohexanecarboxylic acid; (14) (1S,3R,4R,5R)-3-[3-(3,4 dihydroxyphenyl)-3S-hydroxypropanoyl]-1,4,5-trihydroxycyclohexanecarboxylic acid; (15) (1S,3R,4R,5R)-5-[3-(3,4-dihydroxyphenyl)-3R-hydroxypropanoyl]-1,3,4-trihydroxycyclohexanecarboxylic acid; (16) (1 S,3R,4R,5R)-5-[3-(3,4-dihydroxyphenyl)-3S-hydroxypropanoyl]-1,3,4-trihydroxycyclohexanecarboxylic acid; (17) (1 S,3R,4R,5R)-4-[3-(3,4-dihydroxyphenyl)-3R-hydroxypropanoyl]-1,3,5-trihydroxycyclohexanecarboxylic acid; (18) (1S,3R,4R,5R)-4-[3-(3,4-dihydroxyphenyl)-3S-hydroxypropanoyl]-1,3,5-trihydroxycyclohexanecarboxylic acid; (19) cis-5-O-caffeoylquinic acid; (20) 3-O-caffeoylquinic acid lactone; (21) 3-O-caffeoyl-4-O-feruloylquinic acid; and (22) other quinic acid esters, and pharmaceutically acceptable salt thereof.

Typically, the pharmaceutically acceptable carriers or vehicles will include, but are not limited to, binders, diluents, adjuvants, excipients, preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polyvinylpyrrolidine, povidone, crospovidones, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Hom, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225). Tritoqualine and anti H1 may form either a solution in a selected oil vehicle or a suspension of fine particles (comprising any of the excipients disclosed herein, e.g., typical excipients for softgels).

Examples of disintegrating agents include, but are not limited to, complex silicates, croscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, lycopodium and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention, in addition to the active agents, while maintaining effectiveness of the formulations in treating the auditory dysfunctions (e.g., hearing loss, tinnitus, hyperacusis, and related auditory processing disorders). The list provided herein is not exhaustive.

Further still, the agents, and their respective acid or base salts, can be formulated into liquid, preferably aqueous, formulations for storage and administration, as well as dried formulations that may, for example, be used as powders for intranasal or oral administration or be reconstituted into liquid form just prior to administration to a subject. Liquid pharmaceutically administrable compositions can, for example, be prepared by dissolving, dispersing, etc. the particular agent and optional pharmaceutical adjuvants in an aqueous carrier. Aqueous carriers include water (particularly water for injection into humans), alcoholic/aqueous solutions, and emulsions and suspensions. Preferred pharmaceutically acceptable aqueous carriers include sterile buffered isotonic saline solutions. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, and inert gases and the like. Non-aqueous solvents may also be included, although when included they preferably comprise less than about 50%, more preferably less than about 25%, and even more preferably less about 10%, of the total solvent of the solution. Examples of non-aqueous solvents include propylene glycol, ethanol, polyethylene glycol, vegetable oils such as olive oil, and injectable organic esters such as ethyl oleate. The neutraceutical, pharmaceutical and veterinary compositions of the agents, whether dry or liquid, are preferably formulated for oral administration.

If desired, the composition to be administered may also contain minor amounts of nontoxic auxiliary carrier or excipient substances such as wetting agents, emulsifying agents, or solubilizing agents, antioxidants, antimicrobials, pH buffering agents and the like, for example, sodium acetate, sodium citrate, cyclodextrin derivatives, sorbitan monolaurate, triethanolamine acetate, triethanolamine oleate, etc. Actual methods of preparing such dosage forms are known, or will be apparent, to those skilled in this art; for example, see Remington: The Science and Practice of Pharmacy, Mack Publishing Company, Easton, Pa., 20th Edition, 2000. The composition or formulation to be administered will, in any event, contain a quantity of the active compound in an amount effective to alleviate the symptoms of the subject being treated.

As those in the art will appreciate, the agents of the invention may also be formulated for targeted delivery to a subset of tissues or cells in a subject. In general, targeted delivery is accomplished by formulating a compound of the agents with a targeting moiety. Such moieties include lipids, liposomes, and ligands for molecules that bind, or are bound by, other molecules in vivo.

Any derived form of the agents (example synthetic or natural), or a conjugate thereof, can be prepared as an acid salt or as a base salt, as well as in free acid or free base forms. Such compositions if used to prevent or treat auditory dysfunctions are covered under the preferred embodiment of this invention.

The amount of the agent required for use in treatment will vary not only with the particular agent and salt selected, but also with the route of administration, the nature of the condition being treated, and the age and condition of the patient, among other factors, and ultimately is determined at the discretion of the attending physician or clinician. The desired dose may conveniently be presented in a single dose or as divided doses administered at appropriate intervals, for example, as two, three, four or more sub-doses per day. The sub-dose itself may be further divided, for example, into a number of discrete, loosely spaced administrations, such as multiple ingestations of pill doses, or liquid doses.

Administration

The agents of this invention may be administered in a therapeutically effective amount to a subject in need of treatment. Administration of compositions of the invention can be via any of suitable route of administration, particularly by ingestion, or alternatively parenterally, for example, intratympanically, intravenously, intra-arterially, intraperitoneally, intrathecally, intraventricularly, intraurethrally, intrasternally, intracranially, intramuscularly, intranasally, subcutaneously, sublingually, transdermally, or by inhalation or insufflations, or topical by ear instillation for absorption through the skin of the ear canal and membranes of the eardrum. Such administration may be as a single oral dose, defined number of ear drops, or a bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds are preferably formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives. The preparation of suitable, and preferably sterile, parenteral formulations is described in detail in the section entitled "Compositions", above.

In the context of this invention, actual dosage levels for the compositions of the invention can be varied so as to obtain an amount of the active agent(s) that is effective to achieve the desired therapeutic response for a particular patient, compositions and mode of administration. In general, daily administration or continuous infusion at dosages less than those known to produce toxicities will be the preferred therapeutic protocol to enhance the activity of the agent(s). The selected dosage level will depend upon the activity of the particular agent(s), the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

With regard to human and veterinary treatment, the amount of a particular agent(s) that is administered will, of course, be dependent on a variety of factors, including the disorder being treated and the severity of the disorder; activity of the specific agent(s) employed; the age, body weight, general health, sex and diet of the patient; the time of administration, route of administration, and rate of excretion of the specific agent(s) employed; the duration of the treatment; drugs used in combination or coincidental with the specific agent(s) employed; the judgment of the prescribing physician or veterinarian; and like factors well known in the medical and veterinary arts.

In further embodiments, the agent(s) comprises treatment formulations that can be made in powdered form for administration via ingestion, with or without additional ingredients, such as dietary supplements, comprising combination formulas with vitamins, minerals and other nutritional supplements.

Dosage forms include tablets, troches, dispersions, suspensions, solutions, capsules, patches, and the like. The agent(s) may be administered prior to, concurrently with, or after administration of other auditory therapies, or continuously, i.e., in daily doses, during all or part of, a separate auditory therapy regimen. The agent, in some cases, may be combined with the same carrier or vehicle used to deliver the other auditory therapy.

Thus, the present agent(s) may be systemically administered, e.g., orally, in combination with a pharmaceutically acceptable vehicle such as an inert diluent or an assimilable edible carrier. The agent(s) may be enclosed in hard or soft shell gelatin capsules, may be compressed into tablets, or may be incorporated directly with the food of the patient's diet. For oral therapeutic administration, the agent(s) may be combined with one or more excipients and used in the form of ingestible tablets, buccal tablets, troches, capsules, elixirs, suspensions, syrups, wafers, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. Tablets, capsules, pills, granules, microparticles and the like can also comprise an enteric coating, such as a coating of one of the Eudragit® polymers, that will permit release of the agent(s) in the intestines, not in the acidic environment of the stomach.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the agent(s) may be incorporated into sustained-release preparations and devices.

The agent(s) or their compositions may also be administered intravenously or intraperitoneally by infusion or injection. Solutions of the agent(s) or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the agent(s) in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the agent(s) plus any additional desired ingredient present in the previously sterile-filtered solutions.

The present agent(s) may be locally administered, e.g., topically.

For topical administration, the agent(s) may be applied in liquid or cream-based formulations, which preferably will include a dermatologically acceptable carrier, which may be a solid, gel, or liquid. Useful solid carriers include finely divided solids such as talc, clay, microcrystalline cellulose, silica, alumina and the like. Useful liquid carriers include water, alcohols, or glycols or water-alcohol/glycol blends, in which the agent(s) can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, or dripped or flowed into the ear canal using ear droppers or the like. Thickeners such as synthetic polymers, fatty acids, fatty acid salts and esters, fatty alcohols, modified celluloses, and/or modified mineral materials can also be employed with liquid carriers to form spreadable pastes, gels, ointments, soaps, and the like, for application directly to the skin of the user.

Useful dosages of the agent(s) of the invention can be determined by comparing their in vitro activity, and in vivo activity in animal models. Methods for the extrapolation of effective dosages in mice, and other animals, to humans are known to the art. See, e.g., U.S. Pat. No. 4,938,949.

Other drugs or treatments, including treatment with other agents such as chemotherapeutic agents, irradiation, or other anti-cancer agents such as alkylating agents, anti-tumor antibodies, or cytokines, can be used with the present agent(s). See, e.g., *Remington's Pharmaceutical Sciences* ($18^{th}$ ed. 1990) at pages 1138-1162.

In further embodiments, the agent(s) further provides a treatment for hearing injury by acting, in part, to stimulate endogenous protective mechanisms, particularly in cells involved in hearing. The capacity of the agent(s) to induce DNA repair is well documented. For example, Sheng Y, et al., (DNA repair enhancement of aqueous extracts of *Uncaria tomentosa* in a human volunteer study. Phytomedicine. 2001; 8: 275-283) discloses that in a randomized age and gender matched human study, two groups of subjects were treated with either 250 or 350 mg tablets comprising agent(s) extracted from *Uncaria tomentosa* bark for 8 consecutive weeks and compared against a control group not receiving the extract composition. Blood samples comprising blood cells were taken from each group and exposed to hydrogen peroxide to induce free radical DNA damage. Results proved a statistically significant increase in enzymatic DNA repair activity as evidenced by higher levels of repaired DNA single strand breaks in the groups that received the extracted agent(s) as compared to the control group. A similar study was conducted in an animal model (Sheng Y, et al., Enhanced DNA repair, Immune function and reduced toxicity of C-MED-100, a novel aqueous extract from *Uncaria tomentosa*. J Ethnopharmacol. 2000; 69: 115-126.) wherein female W/Fu rats were treated with the extracted agent(s) in doses up to 160 mg/kg body weight, for four weeks by gastric gavage then exposed to 12 Gy of whole body irradiation to induce wide-spread genomic damage. The results proved significantly ($p<0.05$) improved DNA repair capacity relative to control rats not treated with the extract composition. In embodiments of the invention related to treating auditory dysfunctions, whether treating specifically hearing loss, or alternatively prevention of hearing loss such as in the case of treating a person subject to constant noise or high noise levels, or such as in the case of a cancer patient subject to exposure of ototoxic drugs, the current invention contemplates administration of the active agent(s) to a patient for providing protection to the auditory system. Regarding isolation and preparation of the agent(s). Agent(s) of the invention may be produced by chemical synthesis or biochemical synthesis. Agent(s) of the invention may be obtained by extraction or extraction followed by purification from plants, e.g., *Uncaria tomentosa*, microbes, or genetically engineered organisms. Synthesized, extracted, or purified agent(s) may be subject to further chemical modifications or salt formation so long as the intended protective or therapeutic benefit to the auditory system exists in the modified agent(s) or salt. Agent(s) or modified agent(s) of the invention may be used to prepare formulations suitable for the particular route of administration, as discussed above. The extracts of the present invention may be included in one or more nutraceutical compositions, such as nutritional and/or dietary supplements and food additives, or one or more pharmaceutical compositions.

Applications

As described above, certain aspects of the invention relate to compositions that contain an agent(s) of the invention, which are useful in the treatment or prevention of hearing loss or other auditory dysfunctions in, humans, non-human primates (e.g., monkeys, chimpanzees, gorillas and lemurs) or other mammals (e.g., bovine, canine, equine, feline, ovine, murine and porcine animals), and perhaps other animals as well.

In the context of hearing therapy, the agent(s) of the present invention may be used alone, i.e., in monotherapy, or in combination with other therapeutic agents such as, for example, anti-cancer therapies (e.g., radiation, surgery, bone marrow transplantation, etc.), that involve use of drugs that are potentially detrimental to hearing or cells associated with hearing. As will be appreciated, "combination therapy" (in the context of hearing and other therapies) and the like refer to a course of therapy that involves the provision of at least two distinct therapies to achieve an indicated therapeutic effect. For example, a combination therapy may involve the administration of two or more chemically distinct active ingredients, for example, a fast-acting chemotherapeutic drug and the agent(s). The drugs may be delivered or may be administered as part of the same composition or as different compositions according to the same therapeutic regimen or different regimens, depending on the active ingredients involved, the disease to be treated, the age and condition of the patient, etc. Moreover, when used in combination with another therapeutic agent, the administration of the two agents may be simultaneous or sequential. Simultaneous administration includes the administration of a single dosage form that comprises both agents, and the administration of the two agents in separate dosage forms at substantially the same time. Sequential administration includes the prior, concurrent, or subsequent administration of the two or more agents according to the same or different schedules, provided that there is an overlap in the periods during which the treatment is provided. Alternatively, a combination therapy may involve the administration of one or more of the agents of the invention as well as the delivery of radiation therapy and/or surgery or other techniques to either improve the quality of life of the patient.

Kits

In a further embodiment, the present invention provides kits (i.e., a packaged combination of reagents with instructions) containing the active agents of the invention useful for treating an auditory impairment, cochlear inflammation, permanent sensorineural hearing loss, tinnitus, loudness recruitment, hyperacusis, diplacusis or speech intelligibility deficits.

The kit can contain a pharmaceutical composition that includes one or more agents of the invention effective for treating an auditory impairment, cochlear inflammation, permanent sensorineural hearing loss, tinnitus, loudness recruitment, hyperacusis, diplacusis or speech intelligibility deficits and an acceptable carrier or adjuvant, e.g., pharmaceutically acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the agents for example, dissolving of the dry powders, and/or treatment for an auditory impairment, cochlear inflammation, permanent sensorineural hearing loss, tinnitus, loudness recruitment, hyperacusis, diplacusis or speech intelligibility deficits.

The label and/or the instructions can indicate directions for in vivo use of the pharmaceutical composition. The label and/or the instructions can indicate that the pharmaceutical composition is used alone, or in combination with another agent to treat an auditory impairment, cochlear inflammation, permanent sensorineural hearing loss, tinnitus, loudness recruitment, hyperacusis, diplacusis or speech intelligibility deficits.

The label can indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

In one embodiment, the active agent, alkaloid, pentacyclic alkaloid, tannin or phytochemical may be less than 10,000 molecular weight.

In another embodiment, the active agent, alkaloid, pentacyclic alkaloid, tannin or phytochemical may be hydrophilic.

In yet another embodiment, the active agent, alkaloid, pentacyclic alkaloid, tannin or phytochemical or the aqueous extract may be spray dried on maltodextrin.

The following examples are presented to illustrate the present invention and to assist one of ordinary skill in making and using the same. The examples are not intended in any way to otherwise limit the scope of the invention.

EXAMPLES

Example 1

Figure 1:
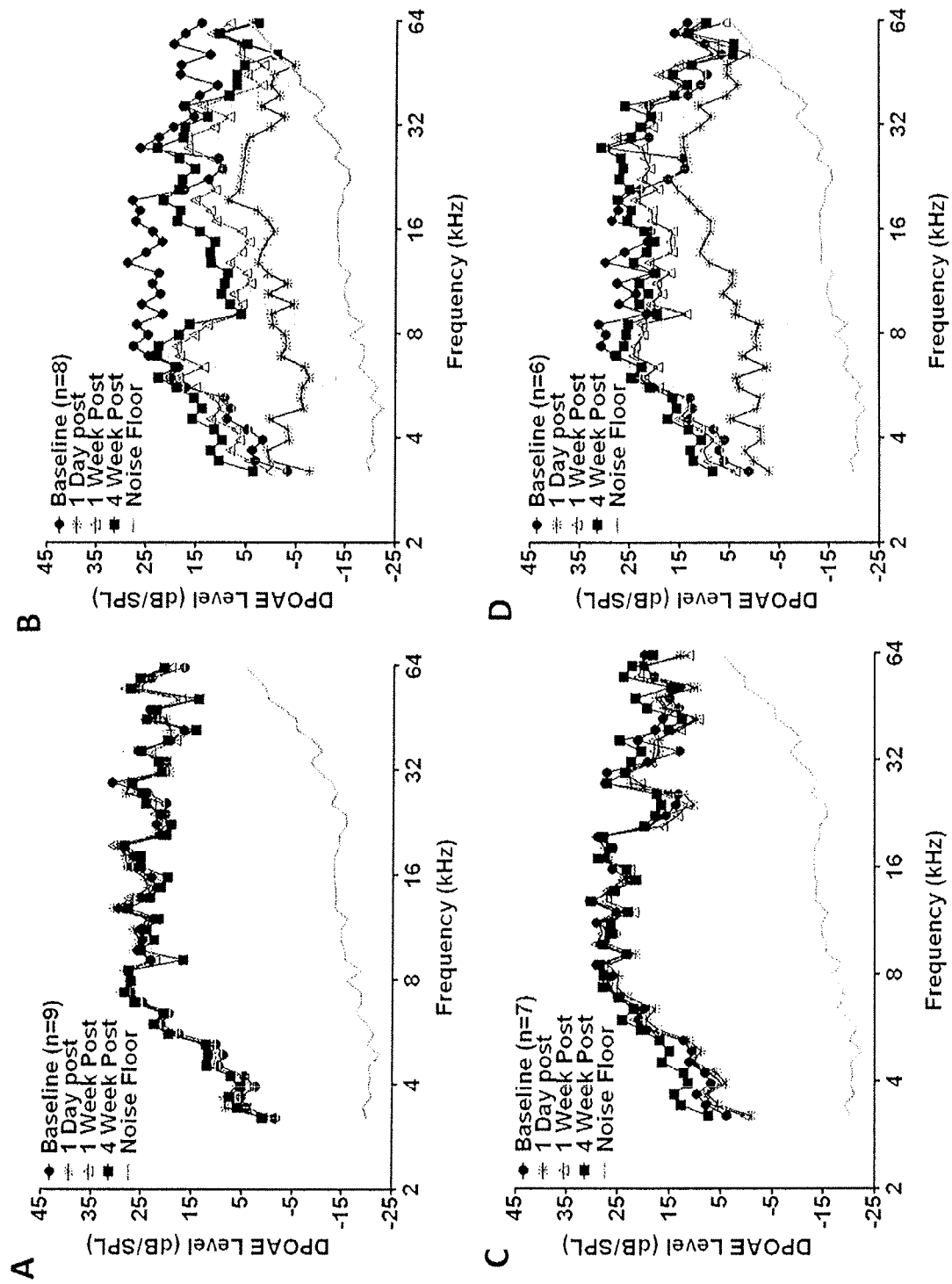
FIG. 1. Sensory Function. DPOAE levels as a function of $f_2$ frequency are shown for each treatment group: (A) control (water gavage-only), (B) noise exposure-only (no gavage), (C) CAE-only and (D) CAE+noise. The gray bars in this and subsequent figures represent the frequency range of the damaging noise. Note that the noise-only group showed depressed DPOAE levels out to 4 weeks after noise exposure while the CAE+noise group showed almost complete recovery as early as 1 week following the noise exposure. Errors bars are standard errors of the means.
Figure 2:
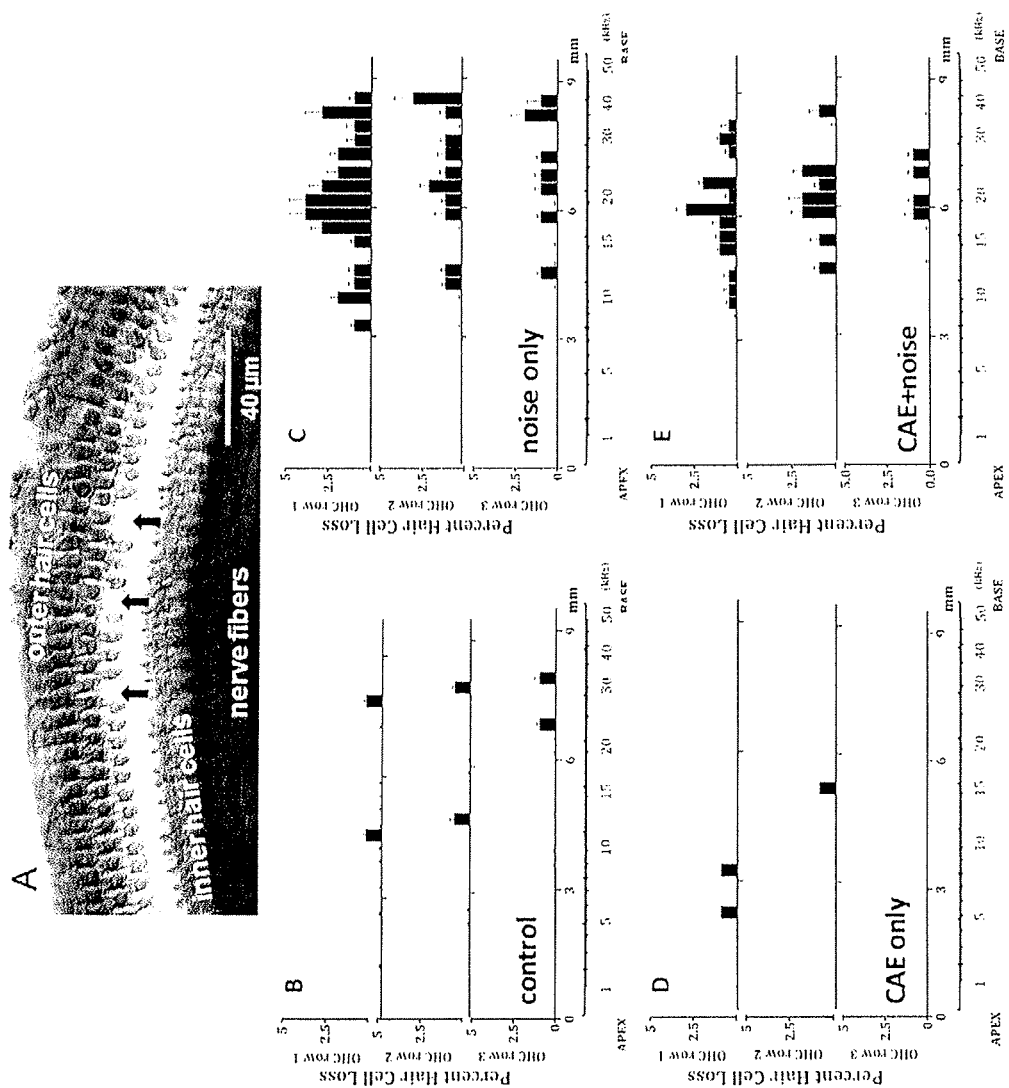
FIG. 2. Cytocochleograms of the peripheral auditory neurosensory epithelium. Photomicrograph of the peripheral auditory neurosensory epithelium is shown in (A) with dark arrows pointing to missing outer hair cells (OHCs) in row 1 of rows 1-3 of OHCs. OHC counts (called cytocochleograms) are displayed for (B) control (water gavage-only), (C) noise exposure-only (no gavage), (D) CAE-only (no noise exposure) and (E) CAE+noise treated groups. These cytocochleograms reveal the percent of missing OHCs from rows 1-3 as a function of distance (0-9 mm) and frequency (1-50 kHz). Note that the noise exposure produced OHCs loss, however the level of missing OHCs is less in the CAE+noise group compared to the noise-only group. Errors bars are standard errors of the means.
Figure 3:
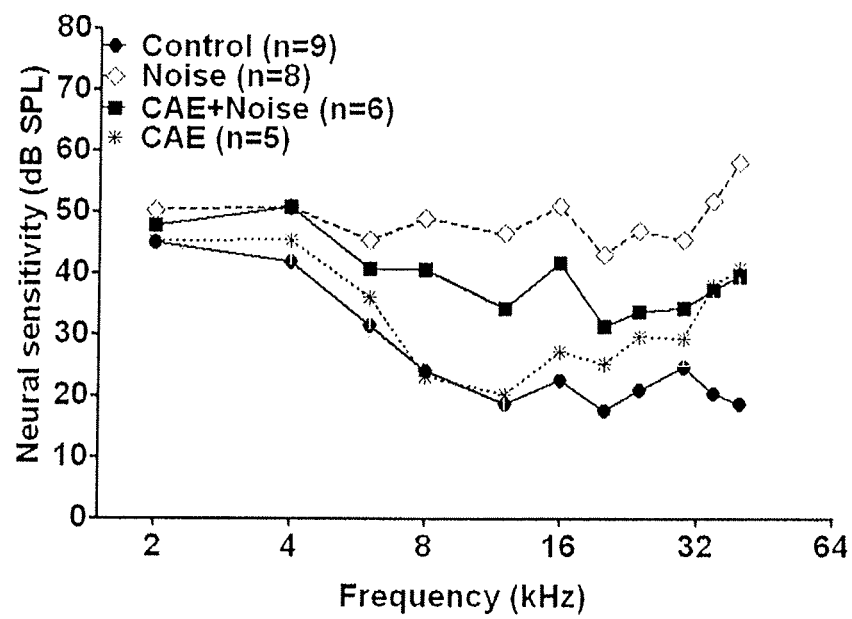
FIG. 3. Neural Function. CAP recordings of neural sensitivity in dB SPL are shown for each group. Note that the CAE+noise group exhibit better neural sensitivity than the noise-only group. Errors bars are standard errors of the means.
Figure 4:
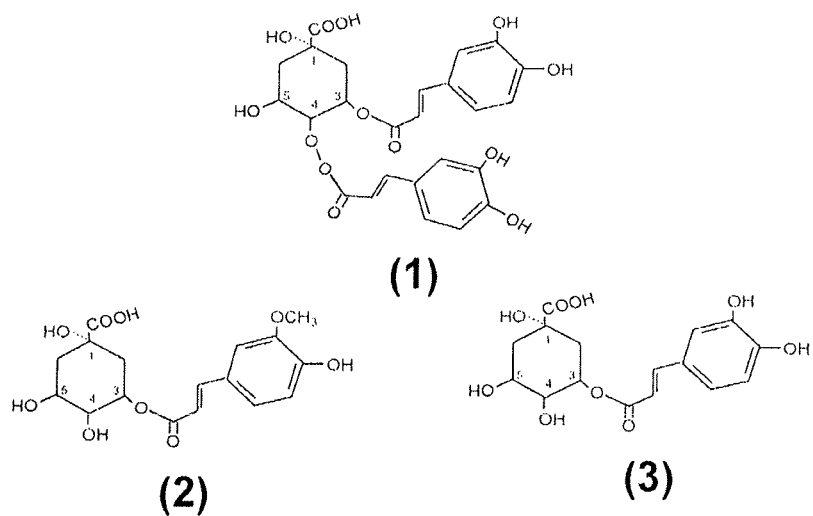
FIG. 4. Chemical Structure. The structure of three representative carboxy alkyl esters are shown: (1) 3,4-O-dicaffeoylquinic acid; (2) 3-O-feruloylquinic acid; (3) 3-O-caffeoylquinic acid.

Examples of the protective effect of a formulation of the agents are shown in FIGS. 1 to 3. FIG. 1 shows distortion product otoacoustic emission (DPOAE) levels as a function of frequency for each treatment group; (A) control (water gavage-only), (B) noise exposure-only (no gavage), (C) CAE-only and (D) CAE+noise. Note: CAE (carboxy alkyl esters) is a formulation of the agent. Within each treatment group DPOAE levels were measured at four time points; baseline (before any experimental treatment) and 1-day, 1-week and 4-weeks post-noise exposure. The control group and the CAE-only group did not receive noise exposure. The gray bar represents the frequency range of the damaging noise (8-kHz OBN at 105 dB SPL for 4 hours). Note that the noise-only group showed depressed DPOAE levels out to 4-weeks after noise exposure while the CAE+noise group showed almost complete recovery as early as 1 week following the noise exposure. Errors bars are standard errors of the means. In this and FIGS. 2 to 4, the data were taken from the publication, Guthrie et al., Brain Research, 1407; 97-106: 2011.

FIG. 2A shows a photomicrograph of the peripheral auditory neurosensory epithelium. Outer hair cell (OHC) counts (called cytocochleograms) are displayed for (B) control (water gavage-only), (C) noise exposure-only (no gavage), (D) CAE-only (no noise exposure) and (E) CAE+noise treated groups. These cytocochleograms reveal the percent of missing OHCs (see arrows in the photomicrograph) from rows 1-3 as a function of distance (0-9 mm) and frequency (1-50 kHz) along the basilar membrane. The noise exposure was an 8-kHz OBN at 105 dB SPL for 4 hours. Note that the noise exposure produced OHCs loss, however the level of missing OHCs is less in the CAE+noise group compared to the noise-only group. Errors bars are standard errors of the means.

FIG. 3 shows compound action potential (CAP) recordings of neural sensitivity in dB SPL for control (water gavage-only), noise exposure-only (no gavage), CAE-only (no noise exposure) and CAE+noise treated groups. The gray bar represents the frequency range of the damaging noise (8-kHz OBN at 105 dB SPL for 4 hours). Note that the CAE+noise group exhibit better neural sensitivity than the noise-only group. All CAP recordings were acquired 4-weeks following noise exposure to assess permanent damage. The frequencies tested ranged from 2.0-40.0 kHz. Errors bars are standard errors of the means.

*Uncaria tomentosa* (UT) also known as "ufia de gato" or cat's claw is a multifunctional medicinal vine that has been used for over 2000 years by ancient civilizations including that of the Tahuantinsuyo (*Inca*) empire (Pilarski et al., 2005). The bioactive components of UT can be divided into hydrophobic and hydrophilic chemotypes (Desmarchelier et al., 1997; Pilarski et al., 2005). The hydrophobic chemotypes include uncarine F, speciophylline, mitraphylline, isomitraphylline, pteropodine and isopteropodine (Bacher et al., 2006; Laus, 2004; Pilarski et al., 2005; Wagner et al., 1985). These hydrophobic chemotypes are derived from tincture preparations and have received considerable attention for their role in immunomodulation, antimicrobial defense, anti-inflammation and antimutagenicity (Keplinger et al., 1999). However, these hydrophobic chemotypes are not representative of medicinal decoctions consumed by ancient and indigenous peoples. For instance, the Ashaninka Indians of the Amazon basin typically boiled UT in water and consumed the resulting hydrophilic chemotypes (Keplinger et al., 1999; Mammone et al., 2006). Recent experiments have demonstrated that carboxy alkyl esters (CAEs; see FIG. 4) are the bioactive components of these hydrophilic chemotypes (Akesson et al., 2005; Sheng et al., 2005). The documented health benefits of CAEs include: antioxidant protection, augmentation of DNA repair, anti-inflammation and immunomodulation (Akesson et al., 2003a, 2003b; Sandoval et al., 2002). These and other health benefits are based on the potency of CAEs to potentiate several biochemical cascades in order to increase the overall capacity of cells to survive and maintain functional integrity (Pero, 2010; Pero et al., 2009; Pero and Lund, 2010). Furthermore current human, animal and in vitro research has supported a role for CAEs in augmenting cellular repair from various physical or chemical exposures (Akesson et al., 2003a, 2003b; Belkaid et al., 2006; Gurrola-Diaz et al., 2010; Lemaire et al., 1999; Mammone et al., 2006; Pero et al., 2002). However, a role for CAEs in preserving auditory function following noise injury has not been studied. Exposure to high levels of sound may induce a multiplicative array of biochemical cascades that perpetuate cell death and/or loss of auditory function (Le Prell et al. 2007; Ohlemiller, 2008). These biochemical cascades may propagate within minutes following exposure and are driven by processes such as ionic dyshomeostasis, mitochondriopathy, energy catastrophe and the proliferation of free radicals. For instance, loud-sound exposure may alter cochlear homeostasis of $Ca2+$, $K+$, and $Na+$ particularly through glutamate excitotoxicity (Hakuba et al., 2000; Le Prell et al. 2007). Mitochondriopathy is evidenced by sound induced increase in mitochondrial permeability and the independent release of at least two mitochondrial nucleases, endonuclease-G and apoptosis inducing-factor (Han et al., 2006; Yamashita et al., 2004b). Furthermore, it is known that loud-sound exposure activates the mitochondria-mediated caspase-dependent cell death pathway (Nicotera et al., 2003; Wang et al., 2007). Energy catastrophe relates to depleted stores of high energy phosphates (e.g., ATP) following loud-sound exposure (Minami et al., 2007). The proliferation of free radicals is exemplified by increased production of reactive lipid, oxygen and nitrogen species (Ohlemiller et al., 1999; Yamashita et al., 2004a). These combined processes (ionic dyshomeostasis, mitochondriopathy, energy catastrophe and free radical production) complement each other to elicit acute and chronic inflammation that ultimately results in cell death and/or loss of auditory function (Masuda et al., 2006; Ohlemiller, 2008). The clinical manifestation of this combinatorial process includes permanent sensorineural hearing loss, tinnitus, loudness recruitment, hyperacusis, diplacusis and speech intelligibility deficits (Basta et al., 2005; Pienkowski and Eggermont, 2010). These auditory impairments reduce an individual's quality of life and work productivity such that the economic burden to society may average $297,000 over an individual's life span (Mohr et al., 2000). A major goal in audiologic rehabilitation and neurootologic medicine is the development of biomedical strategies that preserve auditory sensory and/or neural function following loud-sound exposure. To this end an impressive mosaic of pharmaceuticals that target individual pathophysiologic cascades has been employed (Le Prell et al. 2007; Ohlemiller, 2008). For instance, Ca2+ blockers have been used to regulate ionic homeostasis, creatine supplementation has been employed to restore energy and several types of free radical scavengers have been tested (Minami et al., 2007; Shen et al., 2007). Unfortunately, none of these single-target approaches has gained wide-spread clinical acceptance due in part to inconsistent outcomes. Since loud-sound exposure induces multiple pathologic cascades, then, an alternative approach might be to employ a multifunctional agent that simultaneously targets several pathophysiologic mechanisms. Given that CAEs of UT have demonstrated efficacy as a multifunctional cytoprotective agent in both human and animal studies, we speculated that CAEs might be otoprotective. Therefore, in the current experiment we tested the hypothesis that CAEs of UT will augment recovery of sensory and neuronal functions following noise injury.

Materials

CAEs of UT were prepared by Optigenex Inc. (Hoboken, N.J., USA) as AC-11® (also known as C-MED-100®). The extraction and purification protocol followed a patented (U.S. Pat. Nos. 6,039,649; 6,238,675 B1; 6,361,805 B2 and 6,964,784 B2) process that partly mimics the extraction procedure used by the Ashaninka Indians. The procedure has been published previously (Sheng et al., 2000a, 2000b, 2005). Briefly, the bark (~150 g) of UT is heated in water for 12-24 h at 90-100° C. and the soluble extracts are decanted and ultra-filtered to remove components with a molecular weight that is greater than 10 kDa (e.g., tannins and flavonoids) while the remaining low molecular weight components are spray dried on maltodextrin. Spray dried maltodextrin may be used to manufacture dosage forms for the desired routes of administration, e.g., oral, inhalation, parenteral injection, or topical applications. Bartos chemistry was used to demonstrate the presence of CAEs (Bartos, 1980). For instance, the extracts react with hydroxylamine (10% hydroxylamine hydrochloride in methanol, 10% sodium hydroxide in methanol, pH 10) to produce hydroxamic acid which was then reacted with ferric chloride (0.3% ferric chloride hexahydrate) to exhibit a chromophore with absorbance at 490 nm (Lamm et al., 2001; Sheng et al., 2005). To further confirm the presence of CAE, the extracts produced a 200 nm UV absorption maxima which was standardized against dioctyl phthalate, a typical benzoic acid-type CAE (Sheng et al., 2005). Lastly, a NaOH neutralization procedure served as a third method to verify the presence of CAE. Here NaOH is used to neutralize the extracts in order to determine the base equivalents needed to adjust the pH to 7. Up to 20% of the extracts are CAEs which are the only bioactive constituents (Mammone et al., 2006; Sheng et al., 2005). In the current experiment, the extracts (Optigenex, lot #280809.1785) contained 10.25% CAE. All animals in the CAE treatment groups were treated with this particular lot of extracts.

Animals

Thirty pigmented male Long-Evans rats (250-300 g at 2 months old) were acquired from Harlan Laboratories, Inc. (Livermore, Calif., USA) and served as subjects in these experiments. The animals were housed at the Veterinary Medical Unit (VMU) at the Loma Linda Veteran's Hospital (Loma Linda, Calif., USA). The VMU is accredited by the Association for Assessments and Accreditation of Laboratory Animal Care (AAALAC) and is staffed with a medical veterinarian and veterinary technicians. The animals were maintained in a low-stress and physically-enriched environment where they had free access to food and water. The environmental temperature was maintained at 21° C.±1° C. and the lighting followed a 12 hour light/dark cycle (6:30 am to 6:30 pm). All experimental protocols were conducted during the light cycle and each protocol was approved by the Hospital's Institutional Animal Care and Use Committee. The experimental protocols were designed to minimize the number of animals used, pain and discomfort. Table 1 describes the different animal groups, their treatment regimen and the experimental design. After arriving from Harlan the animals were given 1 week to acclimatize to the VMU. Baseline DPOAEs were then collected on each animal to verify auditory function. The animals were then assigned to one of four groups based on their DPOAE measurements to counterbalance auditory function between groups. CAEs were dissolved in double-distilled water at a concentration of 160 mg/mL to produce a homogenous solution suitable for gastric gavage (Sheng et al., 2000a). A 20-gage animal feeding stainless steel needle was used to intubate alert animals in order to administer 160 mg of the CAE solution per kilogram of animal weight. Fresh solutions were prepared each day and administered via gastric intubation for 28 consecutive days. A control group of animals received water vehicle (volume/body weight) via gastric intubation instead of the CAE solution. Two groups (CAE+noise and noise-only) were exposed to noise (see Noise exposure) on the 29th day. DPOAE was measured again at 1 day, 1 week and 4 weeks following the noise exposure. CAP recordings and tissue collection for hair cell counts (cytocochleograms) were obtained at 4 weeks (end of the study) post-noise exposure.

TABLE 1

Experimental design.

| Groups | Baseline DPOAE testing | 28 days of gavage | Noise exposure | 1-day, 1-week and 4 week post-noise exposure data collection (DPOAE + CAP + hair cell count) |
|---|---|---|---|---|
| CAE + noise | + | CAE | 105 dB OBN | + |
| CAE-only | + | CAE |  | + |
| Noise only | + |  | 105 dB OBN | + |
| Control | + | Water |  | + |

Abbreviations:
CAE, carboxy alkyl ester;
DPOAE, distortion product otoacoustic emission;
CAP, compound action potential;
105 dB OBN, 105 decibel (dB) octave band noise centered at 8 kHz for 4 h.

Noise Exposure

In order to elicit noise induced auditory dysfunction, the animals in the CAE+noise and noise-only groups were exposed to an 8 kHz OBN at 105 dB SPL for 4 h. This noise exposure exceeds the permissible doses for work-place safety in the United States and is known to produce permanent sensorineural auditory dysfunction in rats (Chen and Fechter, 2003; Lorito et al., 2006). Awake and alert animals were placed in a small wire-cloth enclosure (15×13×11 cm) within a reverberant 40 L chamber. Broadband noise was driven by a DS335 Function Generator (Stanford Research System, Menlo Park, Calif., USA) and bandpass filtered with a Frequency Device 9002-Dual-Channel Filter/Amplifier Instrument (Frequency Device Inc., Haverhill, Mass., USA) with a roll-off of 48 dB/octave to produce an OBN with center frequency at 8 kHz. This OBN was then amplified by a HCA1000A Parasound Amplifier (Parasound Products, Inc., San Francisco, Calif., USA) and delivered to Vifa D25AG-05 speakers (Vifa International A/S, Videbaek, Denmark) located approximately 5 cm above the animals' wire-cloth enclosure. Sound pressure levels measured at the rats' pinnae were 105 dBlin SPL in the octave band centered around 8 kHz. These sound pressure measurements were made using an OB-300Quest Type-1 Sound Pressure Meter with ⅓ octave filter set (Quest Electronics, Oconomowoc, Wis., USA).

Assessment of Sensory Function

DPOAE was used to assess the function of the OHCs in the right ear. Each animal was lightly anesthetized with ketamine (44 mg/kg) and xylazine (7 mg/kg) while normal body temperature was maintained using a direct current (dc) heating unit built into the surgical table. All measurements were obtained in a double-walled sound-isolation chamber (Industrial Acoustics Company Inc., Bronx, N.Y., USA). The cubic 2f1–f2 DPOAE was recorded with two primaries, f2 and f1; where f2 is basal to f1 at an f2/f1 ratio of 1.25. The f1 and f2 frequencies were swept basalward in 0.1-octave increments of f2 along the cochlear spiral from f2=3.2 to 63 kHz. The sound pressure level (SPL) for the f1 primary was 65 dB SPL (L1) and that for the f2 primary was 55 dB SPL (L2) with a level ratio of 1.18 (L1/L2). These combined frequency and level ratios were selected to maximize the 2f1–f2 SPL recorded from the external auditory meatus (Whitehead et al., 1995a, 1995b, 1995c.). Two separate realistic dual radial horn tweeters (Radio Shack, Tandy Corp., Ft Worth, Tex., USA) were used to present the primaries, f2 and f1. The primaries were acoustically mixed in the external auditory meatus to avoid artifactual distortion. An ER-10B+ emissions microphone assembly (Etymotic Research, Elk Grove Village, Ill., USA) was used to capture SPLs in the external auditory meatus. A customized signal presentation, acquisition and analysis program written in LabVIEW version 7.1 (National Instruments, Austin, Tex., USA) was used to drive a PCI-4461 computer-based DSP board (National Instruments, Austin, Tex., USA). This allowed for the delivery of the primaries, synchronous averaging and Fourier analysis of 2f1–f2 dB SPLs as a function of f2 frequencies ranging from 3.2 to 63 kHz in 0.1-octave increments. The noise floor was computed by averaging SPLs from the external auditory meatus for frequency bins above and below the 2f1–f2 bin (±3.75 Hz). The measuring microphone assembly and the stimulus delivery system were extended to a probe that was physically and acoustically coupled to each animal's external auditory meatus. A 0.2 cm2 hard-walled cavity that approximates the rat's external auditory meatus was used to calibrate the DPOAE recordings. These calibrations were free of artifacts and did not produce DPOAE SPLs that exceeded the noise floor. A DPOAE is considered to be present when the SPL exceed the noise floor by at least 3 dB.

Assessment of Neural Function

The CAP was used to access the sensitivity of the auditory branch of the VIIIth craniofacial nerve in the right ear. This procedure is terminal (nonsurvival) and therefore deployed at the end of the study (4 weeks post-noise exposure). The animals were anesthetized with xylazine (13 mg/kg, im) and ketamine (87 mg/kg, im) while normal body temperature was maintained using a dc heating unit built into the surgical table. All recordings were obtained in a double-walled sound-isolation chamber (Industrial Acoustics Inc.). The auditory bulla was approached and opened via a ventrolateral surgical approach. The cochlea was warmed using a low-voltage high-intensity lamp. A fine Teflon-coated silver-wire-recording electrode (A-M Systems, Inc., Carlsborg, Wash., USA) with an outer-diameter of 0.1 mm was placed on the round window membrane while a silver chloride electrode (ground) was inserted into neck musculature. A speaker-probe assembly was acoustically coupled to the surgically-resected external auditory meatus. A customized program written in LabVIEW 7.1 (National Instruments) was used to drive a SoundMax Integrated Digital Audio board in order to generate and shape stimulus frequency, timing and intensity. Stimulus frequencies were shaped as a 10 ms burst with ramps of ims on/off-sets. Frequencies between 2 and 40 kHz in approximately ½ octave steps were presented through the probe assembly at a rate of 9.7/s per frequency. The intensity of the stimulus was adjusted in 1 dB steps until an action potential was discernible on a TDS1002 digital oscilloscope (Tektronix Inc., Beaverton, Oreg., USA). Action potentials were amplified (1000-fold) between 0.1 and 1.0 kHz with a Grass A.C. preamplifier (Model P15, W. Warwick, R.I., USA) and averaged over four sweeps. Neural sensitivity was tracked by monitoring the N1 action potential from a descending intensity series. The N1 component of the action potential was identified based on its shape and latency relative to stimulus onset. The approximate response amplitude of the N1 component at the lowest stimulus needed to stimulate the nerve was 1 mV as measured at the output of the preamplifier. Neural sensitivity for a particular frequency was the lowest stimulus intensity in dB SPL needed to elicit an N1 above background noise.

Cytocochleogram

OHCs are among the most sensitive cell types to noise-injury therefore cytocochleograms of missing OHCs were constructed for each animal's right ear. This was conducted at the end of the study (4 weeks post-noise exposure) on the same animals that received CAP testing. Under high-dose anesthesia (xylazine/ketamine 13/87 mg/kg, im) each animal was decapitated and within 60 s *cochleae* were fixed by round-window perilymphatic perfusion with 1 mL of periodate-lysine-paraformaldehyde (PLP). The *cochleae* were then post-fixed for 24 h at 22° C. in PLP. Following fixation the cochlea was washed with 0.1 M phosphate buffered saline then stained with 2% OsO4 in water for 2 h and finally washed again with 70% ethanol. The cochlear neurosensory epithelium was micro-dissected in 70% ethanol then mounted in glycerin on microscope slides. A 40× objective mounted on a Carl Zeiss upright light microscope was used to visualize and count OHCs. OHCs were counted as present when the cell nucleus could be visualized. The degree of cellular damage to surviving cells was not determined. The Müller-rat frequency-place map was used to estimate frequency loci as a function of length along the cochlear spiral (Müller, 1991). This map reflects the logarithmic-tonotopic scale of a rat's cochlea where high frequency receptive OHCs are located at the base while low frequency receptive OHCs are located at the apex. A cytocochleogram showing the percentage of OHC loss as a function of distance from the apex of the cochlea was plotted for each animal. The results were then averaged across each group of subjects for between-group comparisons.

Statistical Analyses

All statistical analyses were conducted with Prism 5 version 5.03 (GraphPad Software, Inc., La Jolla, Calif., USA). The DPOAE data was analyzed for within-group effects. A 16×4 repeated measures analysis of variance (ANOVA) was calculated for DPOAE levels where 16 frequencies within 8-24 kHz were compared across four time points (baseline, 1 day, 1 week and 4 weeks post-noise exposure) within each group (control, noise-only, CAE-only and CAE+noise). Dunnett's post-hoc analyses were performed to determine statistically significant differences between DPOAE levels obtained at baseline compared with those obtained at subsequent time points; 1 day, 1 week and 4 weeks post-noise exposure. The frequency range between 8 and 24 kHz was chosen for statistical analysis because it was the largest area affected by the 8 kHz OBN and it is 1½-octave above the center frequency (8 kHz) of the OBN. This high frequency shift is common among humans and animals exposed to damaging noise and represent the interaction between the maximum displacement of the basilar membrane and the Helmholtz resonance of the external auditory meatus (Johnstone et al., 1986).

The CAP data were analyzed for between-group effects. Therefore, CAP recordings of neural sensitivity in dB SPL were subjected to an 11×4 two-way ANOVA where 11 frequencies (~½ octave steps) within 2-40 kHz were compared across the four treatment groups (control, noise-only, CAE-only and CAE+noise). Lastly, the OHC-count data was also analyzed for between-group effects. A 29×4 two-way ANOVA was calculated where the percent of missing OHCs at 29 serial locations (0.31 mm increments along the entire epithelium) within 9 mm of the neurosensory epithelium was compared between the four treatment groups. Data from CAP and OHC-counts were treated with Dunnett's post-hoc testing to determine significant differences relative to the control group.

Results

Sensory Function

Sensory function as determined by distortion product otoacoustic emission (DPOAE) revealed that CAE treatment preserved outer hair cell (OHC) activity following noise exposure. All groups started and ended the study at the same time therefore DPOAE measurements from vehicle-only and CAE-only groups followed the same time schedule as the noise exposure groups. FIG. 1A shows DPOAE measurements for the vehicle-only group (control). These measurements reveal that DPOAE levels exhibited little variability across time-points. This small variability is representative of normal physiologically active OHCs (Wagner et al., 2008). FIG. 1B shows DPOAE levels for the noise treated group. Note that FIG. 1B shows a significant loss in DPOAE levels at 1 day following noise exposure. At 1 week following noise exposure DPOAE levels of apical (low frequency: 3-7 kHz) and basal (high frequency: 25-34 kHz) components showed marked recovery. However, the middle frequency components (8-24 kHz) and the highest frequency components (frequencies greater than 34 kHz) failed to recover to the same extent as the other frequency components. At 4 weeks post-noise exposure there was a slight improvement in DPOAE levels for the middle frequency components, however, these DPOAE components and the highest frequency components are still significantly depressed relative to that at baseline. These remaining depressions in DPOAE levels are consistent with a permanent sensory impairment. The combined results suggest that the noise exposure induced permanent loss of DPOAE levels 1-4 weeks following noise-treatment.

FIG. 1C shows that CAE treatment alone does not adversely affect OHC function and similar to the control group, DPOAE levels exhibited little variability between time-points. FIG. 1D shows DPOAE levels for the CAE+noise treated group. Note the significant loss in DPOAE levels at 1 day following noise exposure. At 1 week following noise exposure DPOAE levels across-frequencies showed marked recovery. Interestingly, this recovery was almost complete at only 1 week following noise exposure which indicates significant preservation of OHC function. Additionally, at 4 weeks post-noise exposure DPOAE levels across frequencies further improved to approximate DPOAE levels recorded at baseline. The combined results suggest that CAE treatment facilitated almost complete recovery of OHC function following noise injury.

Statistical analyses were conducted on DPOAE levels. Table 2 provides a summary of the F-ratios from several two-way repeated measures ANOVAs where time (baseline, 1 day, 1 week and 4 weeks) and frequency (8-24 kHz) served as main effects for the four groups (control, noise, CAE, CAE+noise). For each group Dunnett's post-hoc testing was used to compare the mean DPOAE levels at baseline to the other three time points. FIG. 1 shows that the noise only group exhibited the largest DPOAE amplitude shifts (Dunnett $p<0.05$) between baseline and the other three time points.

TABLE 2

Results of two-way repeated measures analysis of variance on DPOAE levels.

| | | F-values | | | |
|---|---|---|---|---|---|
| Source | df | Control | Noise | CAE | CAE + noise |
| Time (T) | 3 | 12.33$^a$ | 128.3$^a$ | 11.82$^a$ | 114.9$^a$ |
| Frequency (F) | 15 | 2.386$^a$ | 0.621 | 2.863$^a$ | 0.3557 |
| T × F | 45 | 0.2471 | 1.514$^b$ | 3.072$^a$ | 1.576$^b$ |
| MS$_{ERROR}$ | | (28.49) | (77.34) | (24.67) | (44.93) |

The F-ratios are shown for separate analyses on DPOAE levels from the four treatment groups (control group, noise-only group, CAE-only group and CAE + noise group). Significant main effects of time (baseline, 1-day, 1-week and 4-weeks post-noise exposure) and frequency (8-24 kHz) and the significant time × frequency interactions are indicated.
$^a$p < 0.01.
$^b$p < 0.05.

Neural Function

Compound action potential (CAP) recordings suggested that CAE treatment limited neural impairment following noise exposure. FIG. 3 reveals neural sensitivity within a frequency range of 2-40 kHz for the four treatment groups at 4 weeks post-noise exposure. Note that the noise exposure produced a significant loss in neural sensitivity while the CAE treatment provided significant protection (ANOVA main effect of treatment; $F3,264=65.22$, $p<0.01$). In the noise-only group, neural sensitivity was significantly impaired between 8.0 and 40.0 kHz where the average sensitivity loss was 28 dB relative to untreated control subjects (Dunnett's post-hoc contrast; $p<0.05$). For the CAE treated group, neural sensitivity was slightly elevated between 8.0 and 40.0 kHz where the average sensitivity loss was only 7 dB relative to untreated control subjects (Dunnett's post-hoc contrast; $p>0.05$). This slight shift of 7 dB indicates that systemic CAE treatment affects inner ear neurons possibly by potentiating endogenous mechanisms (see Discussion section). In the CAE+noise group neural sensitivity was mildly impaired between 8.0 and 40.0 kHz where the average sensitivity loss was 13 dB relative to untreated control subjects (Dunnett's post-hoc contrast; $p<0.05$). This mild impairment suggests that the noise treatment had a damaging effect in this group, but the damage was less than that of the noise-only group.

Cytocochleogram

Cytocochleograms of OHC counts from each group of animals revealed that the noise exposure induced cellular loss, but CAE treatment limited the magnitude of the loss. FIG. 2 reveals OHC loss (for rows 1-3) along the length of the cochlear neurosensory epithelium for the different treatment groups (control, noise only, CAE-only and CAE+noise) at a 4 week post-noise exposure survival time. There were statistically significant differences between the four treatment groups (ANOVA main effect of treatment; F3,232=21.45, p<0.01). Cell loss as a function of distance along the neurosensory epithelium of the control group provided a reference for determining the effect of individual treatment (noise-only, CAE-only or CAE+noise). In the noise-only group cell loss was significant toward the basal end of the neurosensory epithelia relative to that of the untreated control subjects (Dunnett's post-hoc contrast; p<0.01). This suggests that the noise exposure produced permanent cell loss which was more prominent at the basal coil (high-frequency responsive area). For the CAE treated group cell loss was similar to that of untreated control subjects (Dunnett's post-hoc contrast; p>0.05). This reveals that the CAE treatment does not adversely affect the OHCs. In the CAE+noise group there was a mild increase in cell loss relative to untreated control subjects (Dunnett's post-hoc contrast; p<0.05). This mild loss suggests that the noise treatment had a damaging effect in this group, but the damage was less than that of the noise-only group.

Discussion

This study provides the first demonstration that treatment with CAE of UT may augment recovery of sensory and neural functions following noise injury. Exposure to an 8 kHz octave band of noise (OBN) at 105 dB SPL for four hours significantly reduced DPOAE levels in all animals at 1 day post-exposure. However, at 1 week post-exposure the CAE treated animals showed almost complete recovery of DPOAE levels while the animals which received only noise failed to show significant recovery. At 4 weeks post-noise exposure the CAE treated animals exhibited additional recovery in DPOAE levels while the animals which received only noise continued to experience reduced DPOAE levels. These findings suggest that CAEs may enhance the recovery of OHC function from both temporary (1 week) and permanent (4 weeks) noise-injury. Indeed, cytocochleograms of the percent of missing OHCs revealed that CAE treated animals suffered from less OHC loss compared to animals which received only noise. The functional and structural preservation observed for OHCs was consistent with round-window recordings of action potentials. Here, CAE treatment prevented significant impairment in neural sensitivity following noise exposure. The combined results imply an otoprotective role for CAE in noise-injury.

REFERENCES FOR EXAMPLE 1

Akesson, C., Lindgren, H., Pero, R. W., Leanderson, T., Ivars, F., 2003a. An extract of Uncaria tomentosa inhibiting cell division and NF-kappa B activity without inducing cell death. Int. Immunopharmacol. 3, 1889-900.

Akesson, C., Lindgren, H., Pero, R. W., Leanderson, T., Ivars, F., 2005. Quinic acid is a biologically active component of the Uncaria tomentosa extract C-Med 100. Int Immunopharmacol. 5, 219-229.

Akesson, C., Pero, R. W., Ivars, F., 2003b. C-Med 100, a hot water extract of Uncaria tomentosa, prolongs lymphocyte survival in vivo. Phytomedicine. 10, 23-33.

Bacher, N., Tiefenthaler, M., Sturm, S., Stuppner, H., Ausserlechner, M. J., Kofler, R., Konwalinka, G., 2006. Oxindole alkaloids from Uncaria tomentosa induce apoptosis in proliferating, G0/G1-arrested and bcl-2-expressing acute lymphoblastic leukaemia cells. Br J Haematol. 132, 615-622.

Bartos, J., 1980. Colorimetric determination of organic compounds by formation of hydroxamic acids. Talanta. 27, 583-590.

Basta, D., Tzschentke, B., Ernst, A., 2005. Noise-induced cell death in the mouse medial geniculate body and primary auditory cortex. Neurosci Lett. 381, 199-204.

Belkaid, A., Currie, J. C., Desgagnés, J., Annabi, B., 2006. The chemopreventive properties of chlorogenic acid reveal a potential new role for the microsomal glucose-6-phosphate translocase in brain tumor progression. Cancer Cell Int. 6, 7.

Chen, G. D., Fechter, L. D., 2003. The relationship between noise-induced hearing loss and hair cell loss in rats. Hear Res. 177, 81-90.

Chung, J. S., Lee, S. B., Park, S. H., Kang, S. T., Na, A. R., Chang, T. S., Kim, H. J., Yoo, Y. D., 2009. Mitochondrial reactive oxygen species originating from Romo1 exert an important role in normal cell cycle progression by regulating p27 (Kip1) expression. Free Radic Res. 43, 729-737.

Coling, D. E., Yu, K. C., Somand, D., Satar, B., Bai, U., Huang, T. T., Seidman, M. D., Epstein, C. J., Mhatre, A. N., Lalwani, A. K., 2003. Effect of SOD1 overexpression on age- and noise-related hearing loss. Free Radic Biol Med. 34, 873-880.

Desmarchelier, C., Mongelli, E., Coussio, J., Ciccia, G., 1997. Evaluation of the in vitro antioxidant activity in extracts of Uncaria tomentosa (Willd.) DC. Phytotherapy Research. 11, 254-256.

Endo, T., Nakagawa, T., Iguchi, F., Kita, T., Okano, T., Sha, S H., Schacht, J., Shiga, A., Kim, T. S., Ito, J., 2005. Elevation of superoxide dismutase increases acoustic trauma from noise exposure. Free Radic Biol Med. 38, 492-498.

Fujioka, M., Kanzaki, S., Okano, H. J., Masuda, M., Ogawa, K., Okano, H., 2006. Proinflammatory cytokines expression in noise-induced damaged cochlea. J Neurosci Res. 83, 575-583.

Gongalves, C., Dinis, T., Batista, M. T., 2005. Antioxidant properties of proanthocyanidins of Uncaria tomentosa bark decoction: a mechanism for anti-inflammatory activity. Phytochemistry. 66, 89-98.

Gurrola-Diaz, C. M., Garcia-López, P. M., Gulewicz, K., Pilarski, R., Dihlmann, S., 2010 Inhibitory mechanisms of two Uncaria tomentosa extracts affecting the Wnt-signaling pathway. Phytomedicine. doi:10.1016

Guthrie, O. W., Carrero-Martinez, F. A., 2010. Real-time quantification of Xeroderma pigmentosum mRNA from the mammalian cochlea. Ear Hear. 31, 714-721.

Guthrie, O. W., 2009. DNA repair proteins and telomerase reverse transcriptase in the cochlear lateral wall of cis-platin-treated rats. J Chemother. 21, 74-79.

Hakuba, N., Koga, K., Gyo, K., Usami, S. I., Tanaka, K., 2000. Exacerbation of noise-induced hearing loss in mice lacking the glutamate transporter GLAST. J Neurosci. 20, 8750-8753.

Han, W., Shi, X., Nuttall, A. L., 2006. AIF and endoG translocation in noise exposure induced hair cell death. Hear Res. 211, 85-95.

Hirose, K., Discolo, C. M., Keasler, J. R., Ransohoff, R., 2005. Mononuclear phagocytes migrate into the murine cochlea after acoustic trauma. J Comp Neurol. 489, 180-194.

Hu, B. H., Henderson, D., Nicotera, T. M., 2006. Extremely rapid induction of outer hair cell apoptosis in the chinchilla cochlea following exposure to impulse noise. Hear Res. 211, 16-25.

Johnstone, B. M., Patuzzi, R., Yates, G. K., 1986. Basilar membrane measurements and the travelling wave. Hear Res. 22, 147-153.

Keplinger, K., Laus, G., Wurm, M., Dierich, M. P., Teppner, H., 1999. *Uncaria tomentosa* (Willd.) DC.—ethnomedicinal use and new pharmacological, toxicological and botanical results. J Ethnopharmacol. 64, 23-34.

Lamm, S., Sheng, Y., Pero, R. W., 2001. Persistent response to pneumococcal vaccine in individuals supplemented with a novel water soluble extract of *Uncaria tomentosa*, C-Med-100. Phytomedicine. 8, 267-274.

Laus, G., 2004. Advances in chemistry and bioactivity of the genus *Uncaria*. Phytother Res. 18, 259-274.

Lemaire, I., Assinewe, V., Cano, P., Awang, D. V., Arnason, J. T., 1999. Stimulation of interleukin-1 and -6 production in alveolar macrophages by the neotropical liana, *Uncaria tomentosa* (uña de gato). Ethnopharmacol. 64, 109-115.

Lorito, G., Giordano, P., Prosser, S., *Martini*, A., Hatzopoulos, S., 2006. Noise-induced hearing loss: a study on the pharmacological protection in the Sprague Dawley rat with N-acetyl-cysteine. Acta Otorhinolaryngol Ital. 26, 133-139.

Mammone, T., Akesson, C., Gan, D., Giampapa, V., Pero, R. W., 2006. A water soluble extract from *Uncaria tomentosa* (Cat's Claw) is a potent enhancer of DNA repair in primary organ cultures of human skin. Phytother Res. 20, 178-183.

Masuda, M., Nagashima, R., Kanzaki, S., Fujioka, M., Ogita, K., Ogawa, K., 2006. Nuclear factor-kappa B nuclear translocation in the cochlea of mice following acoustic overstimulation. Brain Res. 1068, 237-247.

McFadden, S. L., Ohlemiller, K. K., Ding, D., Shero, M., Salvi, R. J., 2001. The Influence of Superoxide Dismutase and Glutathione Peroxidase Deficiencies on Noise-Induced Hearing Loss in Mice. Noise Health. 3, 49-64.

Minami, S. B., Yamashita, D., Ogawa, K., Schacht, J., Miller, J. M., 2007. Creatine and tempol attenuate noise-induced hearing loss. Brain Res. 1148, 83-89.

Mohr, P. E., Feldman, J. J., Dunbar, J. L., McConkey-Robbins, A., Niparko, J. K., Rittenhouse, R. K., Skinner, M. W., 2000. The societal costs of severe to profound hearing loss in the United States. Int J Technol Assess Health Care. 16, 1120-1135.

Müller, M., 1991. Frequency representation in the rat cochlea. Hear Res. 51, 247-254. Nicotera, T. M., Hu, B. H., Henderson, D., 2003. The caspase pathway in noise-induced apoptosis of the chinchilla cochlea. J Assoc Res Otolaryngol. 4, 466-477.

Ohlemiller, K. K., 2003. Oxidative cochlear injury and the limitations of antioxidant therapy. Semin Hear. 24, 123-134.

Ohlemiller, K. K., 2008. Recent findings and emerging questions in cochlear noise injury. Hear Res. 245, 5-17.

Ohlemiller, K. K., Wright, J. S., Dugan, L. L., 1999. Early elevation of cochlear reactive oxygen species following noise exposure. Audiol Neurootol. 4, 229-236.

Pero, R. W., Amiri, A., Sheng, Y., Welther, M., Rich, M., 2005. Formulation and in vitro/in vivo evaluation of combining DNA repair and immune enhancing nutritional supplements. Phytomedicine. 2005, 12, 255-263.

Pero, R. W., Giampapa, V., Vojdani, A., 2002. Comparison of a broad spectrum anti-aging nutritional supplement with and without the action of a DNA repair enhancing cat's claw extract. J Anti Aging Med. 5, 345-355.

Pero, R. W., 2010. Health consequences of catabolic synthesis of hippuric acid in humans. Curr Clin Pharmacol. 5, 67-73.

Pero, R. W., Lund, H., 2010. Dietary quinic acid supplied as the nutritional supplement AIO+AC-11® leads to induction of micromolar levels of nicotinamide and tryptophan in the urine. Phytother Res. doi: 10.1002/ptr.3348.

Pero, R. W., Lund, H., Leanderson, T., 2009. Antioxidant metabolism induced by quinic acid. Increased urinary excretion of tryptophan and nicotinamide. Phytother Res. 23, 335-346.

Pienkowski, M., Eggermont, J. J., 2010. Intermittent exposure with moderate-level sound impairs central auditory function of mature animals without concomitant hearing loss. Hear Res. 261, 30-35.

Pilarski, R., Zieliński, H., Ciesiołka, D., Gulewicz, K., 2005. Antioxidant activity of ethanolic and aqueous extracts of *Uncaria tomentosa* (Willd.) DC. J Ethnopharmacol. 104, 18-23.

Sandoval, M., Okuhama, N. N., Zhang, X. J., Condezo, L. A., Lao, J., Angeles, F. M., Musah, R. A., Bobrowski, P., Miller, M. J., 2002. Anti-inflammatory and antioxidant activities of cat's claw (*Uncaria tomentosa* and *Uncaria guianensis*) are independent of their alkaloid content. Phytomedicine. 9, 325-337.

Satou, K., Hori, M., Kawai, K., Kasai, H., Harashima, H., Kamiya, H., 2009. Involvement of specialized DNA polymerases in mutagenesis by 8-hydroxy-dGTP in human cells. DNA Repair. 8, 637-642.

Shen, H., Zhang, B., Shin, J. H., Lei, D., Du, Y., Gao, X., Wang, Q., Ohlemiller, K. K., Piccirillo, J., Bao, J., 2007. Prophylactic and therapeutic functions of T-type calcium blockers against noise-induced hearing loss. Hear Res. 226, 52-60.

Sheng, Y., Akesson, C., Holmgren, K., Bryngelsson, C., Giamapa, V., Pero, R. W., 2005. An active ingredient of Cat's Claw water extracts identification and efficacy of quinic acid. J Ethnopharmacol. 96, 577-584.

Sheng, Y., Bryngelsson, C., Pero, R. W., 2000a. Enhanced DNA repair, immune function and reduced toxicity of C-MED-100, a novel aqueous extract from *Uncaria tomentosa*. J Ethnopharmacol. 69, 115-126.

Sheng, Y., Li, L., Holmgren, K., Pero, R. W., 2001. DNA repair enhancement of aqueous extracts of *Uncaria tomentosa* in a human volunteer study. Phytomedicine. 8, 275-282.

Sheng, Y., Pero, R. W., Wagner, H., 2000b. Treatment of chemotherapy-induced leukopenia in a rat model with aqueous extract from *Uncaria tomentosa*. Phytomedicine. 7, 137-143.

Schildkraut, E., Miller, C. A., Nickoloff, J. A., 2005. Gene conversion and deletion frequencies during double-strand break repair in human cells are controlled by the distance between direct repeats. Nucleic Acids Res. 33, 1574-1580.

Van Campen, L. E., Murphy, W. J., Franks, J. R., Mathias, P. I., Toraason, M. A., 2002. Oxidative DNA damage is associated with intense noise exposure in the rat. Hear Res. 164, 29-38.

Wang, J., Ruel, J., Ladrech, S., Bonny, C., van de Water, T. R., Puel, J. L., 2007. Inhibition of the c-Jun N-terminal kinase-mediated mitochondrial cell death pathway restores auditory function in sound-exposed animals. Mol Pharmacol. 71, 654-666.

Wagner, H., Kreutzkamp, B., Jurcic, K., 1985. The alkaloids of *Uncaria tomentosa* and their phagocytosis-stimulating action. Planta Med. 5, 419-423.

Wagner, W., Heppelmann, G., Vonthein, R., Zenner, H. P., 2008. Test-retest repeatability of distortion product otoacoustic emissions. Ear Hear. 29, 378-391.

Whitehead, M. L., Stagner, B. B., Lonsbury-Martin, B. L., Martin, G. K., 1995a. Effects of ear-canal standing waves on measurements of distortion-product otoacoustic emissions. J Acoust Soc Am. 98, 3200-3214.

Whitehead, M. L., Stagner, B. B., McCoy, M. J., Lonsbury-Martin, B. L., Martin, G. K., 1995b. Dependence of distortion-product otoacoustic emissions on primary levels in normal and impaired ears. II. Asymmetry in L1,L2 space. J Acoust Soc Am. 97, 2359-2377.

Whitehead, M. L., McCoy, M. J., Lonsbury-Martin, B. L., Martin, G. K., 1995c. Dependence of distortion-product otoacoustic emissions on primary levels in normal and impaired ears. I. Effects of decreasing L2 below L1. J Acoust Soc Am. 97, 2346-2358.

Yamane, H., Nakai, Y., Takayama, M., Iguchi, H., Nakagawa, T., Kojima, A., 1995. Appearance of free radicals in the guinea pig inner ear after noise-induced acoustic trauma. Eur Arch Otorhinolaryngol. 252, 504-508.

Yamashita, D., Jiang, H. Y., Schacht, J., Miller, J. M., 2004a. Delayed production of free radicals following noise exposure. Brain Res. 1019, 201-209.

Yamashita, D., Miller, J. M., Jiang, H. Y., Minami, S. B., Schacht, J., 2004b AIF and EndoG in noise-induced hearing loss. Neuroreport. 15, 2719-2722.

Yang, W. P., Henderson, D., Hu, B. H., Nicotera, T. M., 2004. Quantitative analysis of apoptotic and necrotic outer hair cells after exposure to different levels of continuous noise. Hear Res. 196, 69-76.

Example 2

In response to stress, spiral ganglion neurons may remodel intracellular pools of DNA repair proteins. This hypothesis was addressed by determining the intracellular location of three classic DNA excision repair proteins (XPA, CSA and XPC) within the neurons under normal conditions, 1 day after noise stress (105 dB/4 hours) and following DNA repair adjuvant therapy with carboxy alkyl esters (CAEs; 160 mg/kg/28 days). Under normal conditions three intracellular compartments were enriched with at least one repair protein. These intracellular compartments were designated nuclear, cytoplasmic and perinuclear. After the noise stress each repair protein aggregated in the cytoplasm. After CAE therapy each intracellular compartment was enriched with the three DNA repair proteins. Combining noise stress with CAE therapy resulted in the enrichment of at least two repair proteins in each intracellular compartment. The combined results suggest that in response to noise stress and/or otoprotective therapy, spiral ganglion neurons may selectively remodel compartmentalized DNA repair proteins.

Methods
Animal Care and Use

Experiments were conducted on male Long-Evans rats (250-300 g at 2 months old) that were purchased from Harlan Laboratories, Inc. (Livermore, Calif., USA). The animals were housed in pairs in environmentally enriched cages in a rat vivarium (21°±1° C.; 12-hour light/dark cycle). A total of 36 animals served as subjects. Except for the control group (N=10); the animals were either exposed to noise (N=10), treated with CAE (N=8) or co-treated with CAE+noise (N=8). All experimental protocols were approved by the Institutional Animal Care and Use Committee (IACUC) at the Loma Linda Va. Medical Center. The IACUC approval process certifies that all protocols are in compliance with the Public Health Service (PHS) Policy on Humane Care and Use of Laboratory Animals and the Animal Welfare Act.

CAE Treatment

CAE treatment is known to improve DNA repair capacity among humans and rats [27],[29]. Furthermore, previous research has shown that Long-Evans rats gavaged with CAE (160 mg/kg) for 28 days exhibited protection from noise induced hearing loss [33]. Therefore this CAE treatment regimen was employed. Briefly, all animals had free access to water and their diet (ad libitum) consisted of standard non-purified Teklad 7001 rat pellets (Teklad Diets, Madison Wis., USA). This diet was supplemented with CAE for animals in the CAE groups. CAE was obtained from Optigenex Inc. (Hoboken, N.J., USA) in powdered form (AC-11®) and then dissolved in double-distilled water at a concentration of 160 mg/ml as described previously [27], [33]. A 20-gauge animal feeding stainless steel needle was used to intubate alert animals in order to administer CAE (160 mg/kg). Fresh solutions of CAE were prepared each day and administered via gastric intubation for 28 consecutive days. On the 29th day, half the animals were treated with noise.

Noise Exposure

Long-Evans rats exposed to an 8 kHz octave band of noise (OBN) at 105 dB SPL for 4 hours are known to exhibit permanent hearing loss [34],[35]. Therefore, this noise exposure was used in the current studies and the protocol has been described previously [33]. Briefly, awake and alert animals were placed in a small wire-cloth enclosure (15× 13×11 cm) within a reverberant 40-L chamber. An HCA1000A Parasound Amplifier (Parasound Products, Inc., San Francisco, Calif., USA) was used to drive speakers located approximately 5 cm above the wire-cloth enclosure. Sound pressure levels measured at the rats' pinnae were 105 dBlin SPL in the octave band centered around 8 kHz. These sound pressure measurements were made using an OB-300 Quest Type-1 Sound Pressure Meter with ⅓ octave filter set (Quest Electronics, Oconomowoc, Wis., USA). Noise exposed animals were subsequently used for immunohistochemical studies as described below.

Immunohistochemistry
Animal and Tissue Preparation

One day after the noise exposure, five animals from the control and noise groups and three animals from the CAE and CAE+noise groups (total of 16 rats) were anesthetized with ketamine/xylazine (87/13 mg/kg, im). After a negative response to a paw pinch, the animals were euthanized via transcardial perfusion with phosphate-buffered saline (PBS; 10 mM, pH 7.4) followed by periodate-lysine-paraformaldehyde fixation [36]. The animals were then decapitated and the epidermis surgically removed. The lower mandible was then dissected and the bulla was opened to allow for additional fixation. The specimens were then post-fixed in 4% paraformaldehyde for at least 24 hrs at 22° C. They were then decalcified in 10% formic acid and neutralized in 5% sodium sulfite. This procedure has been described previously [6,11,36] and included incubating the specimens in fresh formic acid every two days at 22° C. Decalcification was monitored every two days by removing 2 ml of the used formic acid and combining this with 1 ml of 5% ammonium hydroxide and 1 ml of 5% ammonium oxalate. End-point decalcification was achieved when the formic acid-ammonium hydroxide/oxalate reaction failed to produce visible white precipitates in three consecutive attempts over 1 week. The specimens were then neutralized overnight by incubating in 5% sodium sulfite at 22° C. then rinsed for at least eight hours in dH$_2$O prior to trimming and paraffin embedding. Paraffin embedded blocks were sectioned horizontally with a Leica RM2255 rotary microtome (Leica Microsystems Inc., Bannockburn, Ill., USA) at 5 or 8 μm and mounted on subbed slides. Liver tissues were simultaneously harvested, post-fixed, paraffin embedded, sectioned and mounted on subbed slides. The sections were then stored at 22° C. prior to immunolabeling.

Immunolabeling

Figure 5:
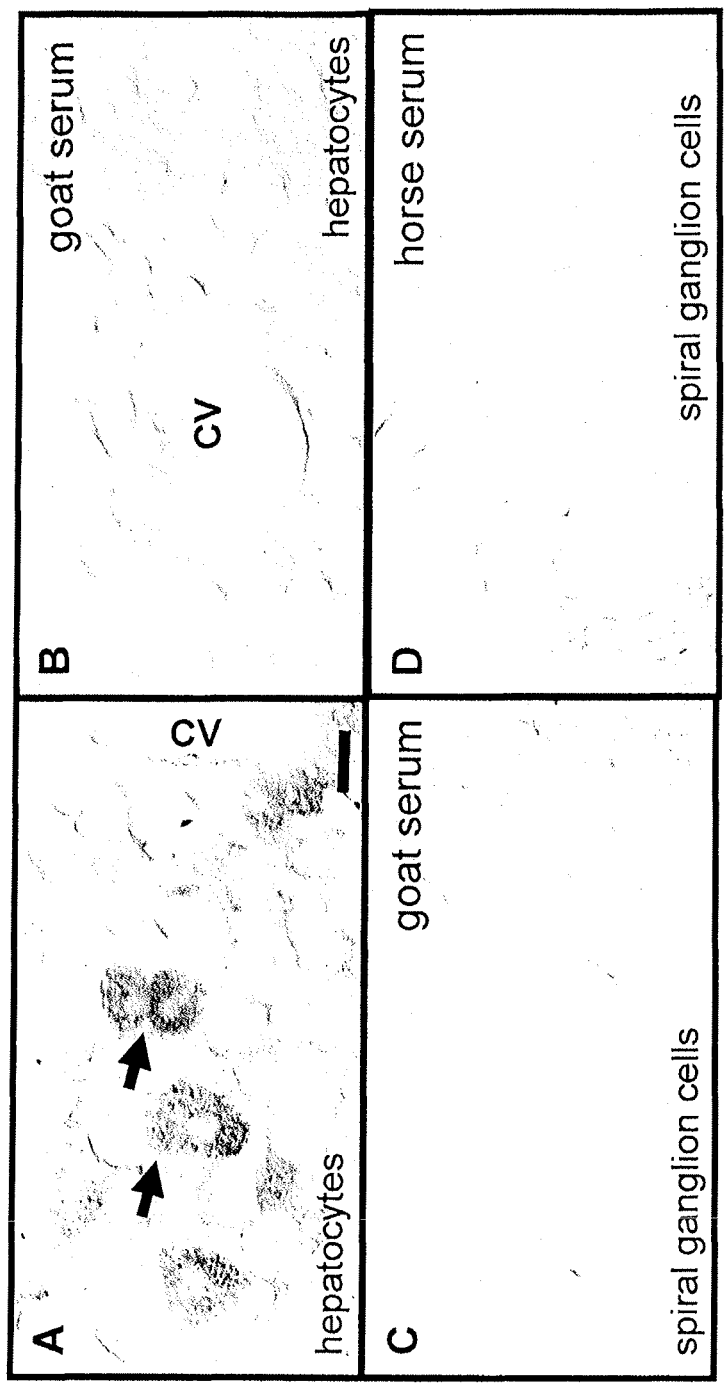
FIG. 5. Positive and negative controls. (A) The immunohistochemistry procedure produced prominent reaction products (see arrows) within hepatocytes (positive control cells). (B-D) Omitting the primary antibody from the immunohistochemistry procedure resulted in negative reaction products (negative control). The respective blocking serum for each antibody is indicated. The abbreviation CV is central vein. Scales bar (10 µm) in (A) applies to all panels.

Tissue sections were de-paraffinized then incubated in 30% $H_2O_2$ for 10 min at 22° C. They were then heated to 90-98° C. in a low pH (0.80-3.06) sodium citrate-citric acid buffer for 20 min (antigen retrieval). Afterwards, the sections were rinsed thoroughly with PBS (pH 7.4). They were then pre-treated with a blocking solution of normal horse or goat serum, 10% Triton X-100 and 2% bovine serum albumin (BSA; Sigma, St. Louis, Mo., USA) in PBS for 1 hour. The primary antibodies were diluted in the blocking solution at a 1:100 concentration. The primary antibodies are commercially available and included anti-XPC (sc-22535), anti-XPA (sc-853) and anti-CSA (sc-25369) (Santa Cruz Biotechnology, Inc., Santa Cruz, Calif., USA). These primary antibodies have been characterized previously through pre-absorption experiments, immunohistochemistry and Western blots [36],[37],[12]. Nevertheless, negative control experiments were conducted such that the sections were incubated with blocking serum instead of the primary antibodies (FIG. 5). After 48 hr incubation at 0° C. with the primary antibodies (or blocking serum for negative control sections) the sections were rinsed with PBS. They were then treated with biotinylated anti-goat or anti-rabbit secondary antibodies (Vector Laboratories, Temecula, Calif., USA) diluted 1:100 in PBS+2% BSA for 24 hours at 0° C. The sections were then rinsed in PBS (pH 7.4) and incubated with preformed avidin-biotin-peroxidase complexes (Vectastain ABC reagent; Vector Laboratories, Inc., Burlingame, Calif., USA) for one hour, rinsed again with PBS and then treated with a solution of Trizma pre-set crystals (1.58 g; Sigma-Aldrich, St. Louis, Mo., USA). Afterwards the sections were washed in PBS (pH 7.4) and stained for 10 min with 3,3'-diaminobenzidine tetrahydrochloride. These stained sections were then dehydrated in a graded series of ethyl alcohol then cleared with xylene and cover slipped in Shandon-Mount (Anatomical Pathology, Pittsburgh, Pa., USA).

Data Analysis

Spiral ganglion cells were counted by three researchers who were blind to the experimental conditions. For each animal, 80 m (control and noise groups) or 45 m (CAE and CAE+noise groups) of mid-modiolar cochlear sections were analyzed under oil immersion at 100× magnification. The number of spiral ganglion cells showing cytoplasmic, diffuse, nuclear or perinuclear immunoreactivity was determined for each of the three proteins (XPC, XPA and CSA). Profiles of spiral ganglion cells were detected throughout the entire thickness of the sections and only neurons with a well-defined soma and nucleus was included in the cell counts. Image-Pro® plus version 6.3 (Media Cybemetics Inc., Bethesda, Md., USA) for Windows™ was used for recording of 1-pixel wide linescans. These linescans were recorded along the central axis of the cell bodies of neurons to objectively verify the subcellular localization patterns (FIGS. 6C, F, I and L). Statistical differences were determined with analysis of variance (ANOVA) followed by Tukey-Kramer post-hoc testing. Within group analyses were conducted, therefore within a particular group the number of cells that exhibit each pattern was compared to determine significant differences between the patterns. Additionally, between group comparisons were conducted to determine differences as a function of treatment conditions.

Results

Controls

DNA repair activity in the rat liver is among the highest of all the major organs such as heart, brain, lung, spleen and muscle [38]. Furthermore, the mRNA of several types of DNA repair genes including XPC and XPA has previously been purified from the liver [39]. Additionally, recent immunohistochemical experiments have confirmed the expression of DNA repair proteins such as XPC and XPA within rat hepatocytes [40]. Therefore in the current study, rat hepatocytes served as positive controls for the immunohistochemical experiments. FIG. 5A is a Nomarski micrograph that reveals XPC immunoreactivity within hepatocytes. The reaction products are prominent and granular to homogenous in appearance. This immunoreactivity was representative of that observed for XPA and CSA within hepatocytes. Omitting only the antibodies from the immunohistochemical procedure (negative control) yielded no reaction products in hepatocytes or spiral ganglion neurons (FIG. 5B-5D).

Intracellular Distribution Patterns

Figure 6:
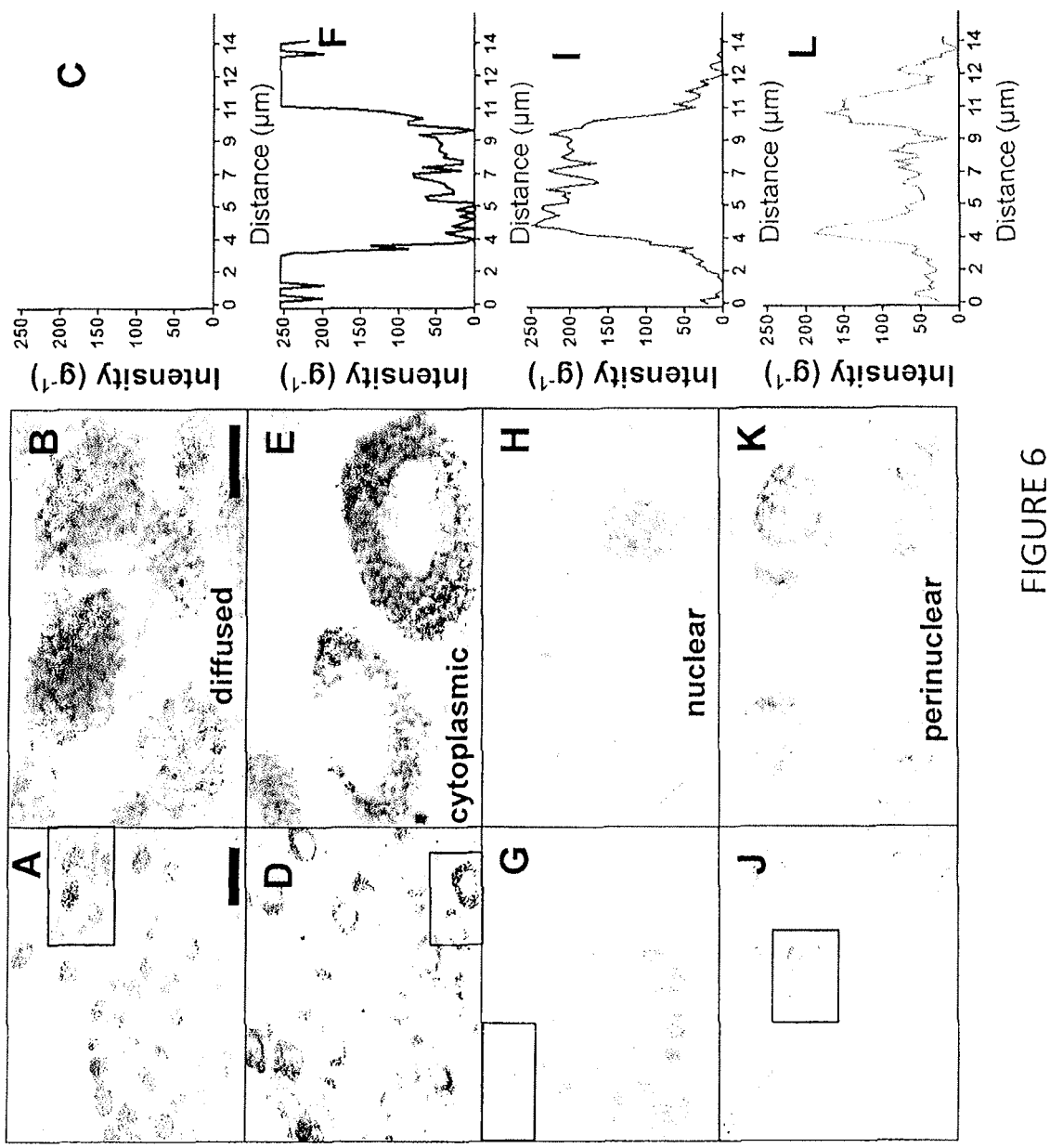
FIG. 6. Representative examples of the intracellular distribution patterns. (A) Photomicrograph of a field of neurons exhibiting diffuse expression. (B) Enlargement of the area outlined in (A) showing that reaction products were distributed throughout the soma. (C) A representative 1-pixel wide linescan demonstrate that neurons with this diffuse pattern exhibit a specific morphologic profile where chromogen intensity is linear across the soma. The y-axis in panels C, F, I and L are inverted gray (g) levels (l/g). (D) Photomicrograph of a field of neurons exhibiting cytoplasmic expression. (E) Enlargement of the area outlined in (D) showing that reaction products were predominantly localized in the cytoplasm. (F) A representative 1-pixel wide linescan demonstrate that cytoplasmic reactive neurons exhibit a specific morphologic profile where chromogen intensity in the nucleoplasm is minimal compared to the cytoplasm. (G) Photomicrograph of a field of neurons exhibiting nuclear and diffuse expression. (H) Enlargement of the area outlined in (G) showing nuclear reactive neurons. (I) A representative 1-pixel wide linescan reveal that nuclear reactive neurons exhibit a specific morphologic profile where chromogen intensity in the nucleoplasm is maximal compared to the cytoplasm. (J) Photomicrograph of a field of neurons exhibiting perinuclear expression. (K) Enlargement of the area outlined in (J) showing reaction products were predominantly localized around the nucleus with residual staining around the plasmalemma. (L) A representative 1-pixel wide linescan reveal that the perinuclear localization pattern exhibits a specific morphologic profile where chromogen intensity is maximal at the nuclear annulus. The scale bar (20 µm) in panel A applied to panels D, G and J. The scale bar (10 µm) in panel B applied to panels E, H, and K.

Spiral ganglion neurons were found to compartmentalize the repair proteins in their cytoplasm, nucleoplasm or at perinuclear loci. This compartmentalization was manifested in four distinct intracellular distribution patterns designated as diffuse, cytoplasmic, nuclear and perinuclear. FIG. 6 reveals each of these patterns for the XPC protein, which is representative of the other DNA repair proteins. FIGS. 6A-6B are high resolution photomicrographs of the diffuse pattern. The immunoreactivity is diffused throughout the soma and there is no clear distinction between the nucleoplasm and the cytoplasm. This pattern can be objectively profiled with linescans across the diameter of the soma as demonstrated in FIG. 6C. FIGS. 6D-6E are representative high resolution photomicrographs of the cytoplasmic localization pattern. This particular localization pattern can be objectively profiled with linescans across the diameter of the soma as demonstrated in FIG. 6F. FIGS. 6G-6H reveals the nuclear localization pattern where immunoreactivity is predominantly localized in the nucleoplasm. This pattern shows a distinct linescan profile (FIG. 6I). FIGS. 6J-6K illustrate the perinuclear localization pattern which also produces a unique linescan signature (FIG. 6L).

Cell Counts

Figure 7:
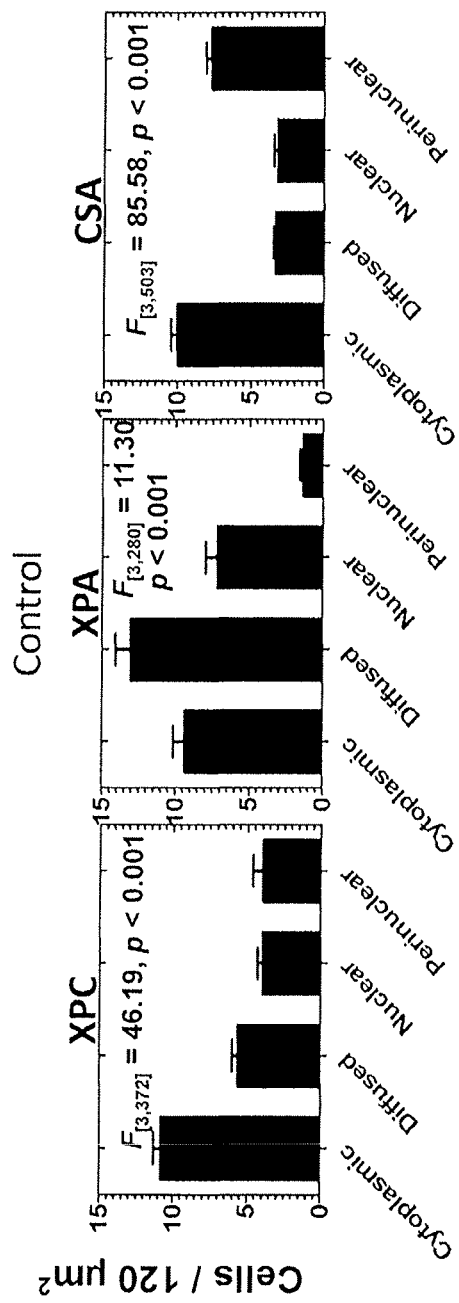
FIG. 7. Allocation of repair proteins across subcellular compartments. The panels illustrate cell counts from the control group (normal, N=5). Each subcellular compartment is enriched with at least one repair protein. For instance, the XPC protein is predominantly localized in the cytoplasm while XPA is primarily diffused throughout the cytoplasm and nucleus. Additionally, the CSA protein exhibits a preference for cytoplasmic and perinuclear loci. Each bar represents mean±SEM.

FIG. 7 is an illustration of spiral ganglion cell counts as a function of distribution pattern from the control group. Note that all three intracellular compartments (cytoplasmic, nuclear and perinuclear) were enriched with at least one protein. For instance, the XPC protein was preferentially compartmentalized in the cytoplasm while the XPA protein was diffused (diffuse pattern) throughout the cytoplasm and the nucleus. Furthermore, the CSA protein was preferentially localized in the cytoplasm and at perinuclear loci. This heterogeneous distribution was further supported by statistical analyses conducted on the number of patterns derived from individual proteins. A one-way repeated measure ANOVA revealed significant differences between the intracellular distribution patterns for the XPC ($p<0.001$), XPA ($p<0.001$) and CSA ($p<0.001$) proteins. For instance, there was a gradient in the distribution of XPC and Tukey-Kramer pairwise comparisons revealed that the cytoplasmic distribution pattern was significantly higher than the other patterns ($p<0.05$). XPA positive cells showed significant cytoplasmic, diffuse and nuclear patterns compared to the perinuclear pattern but the diffuse pattern was the most dominant (Tukey-Kramer pairwise contrasts; $p<0.05$). For the CSA protein, the cytoplasmic and perinuclear patterns were significantly higher than the other patterns (Tukey-Kramer pairwise contrasts; $p<0.05$).

Figure 8:
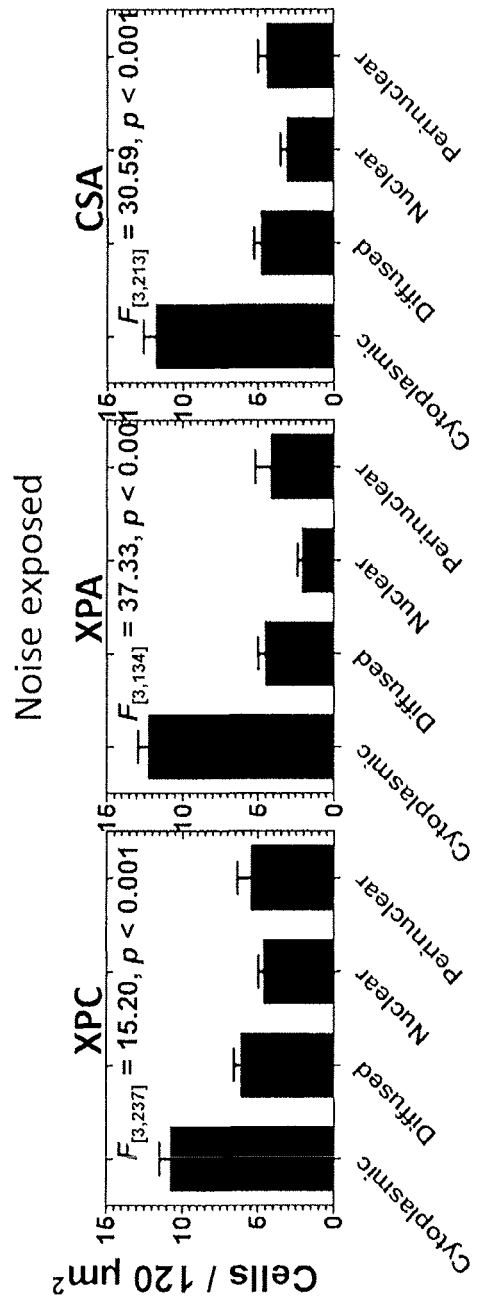
FIG. 8. Re-allocation of repair proteins to the cytoplasmic compartment. The panels illustrate cell counts from the noise exposed group (N=5). Note that all the proteins exhibited preferential localization in the cytoplasm. Each bar represents mean±SEM.

FIG. 8 is an illustration of spiral ganglion cell counts as a function of distribution pattern following the noise exposure. Note that all three proteins (XPC, XPA and CSA) were preferentially compartmentalized in the cytoplasm. This uniform cytoplasmic response is in contrast with that of the control condition where all compartments were enriched with at least one repair protein. A one-way repeated measure ANOVA revealed significant differences between the intracellular distribution patterns for the XPC ($p<0.001$), XPA ($p<0.001$) and CSA ($p<0.001$) proteins. For instance, the cell counts as a function of distribution pattern can be described as a gradient where cytoplasmic location is the most significant (Tukey-Kramer pairwise contrasts; $p<0.05$).

Figure 9:
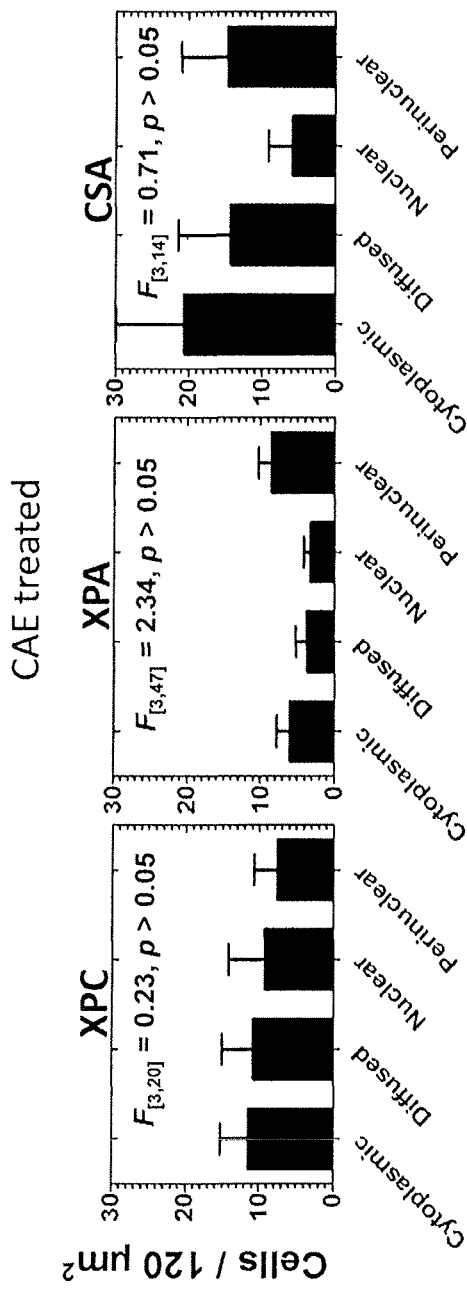
FIG. 9. Allocation of repair proteins across subcellular compartments. The panels illustrate cell counts from the CAE treated group (N=3). The CAE treatment apparently equalized the distribution of the proteins across patterns. For instance, statistical analyses reveal that no one localization pattern is significantly different than the other patterns for a given protein. Each bar represents mean±SEM.

FIG. 9 is an illustration of spiral ganglion cell counts as a function of distribution pattern following CAE treatment. Gradients in the cell counts for all three proteins could be detected. However, unlike noise exposure there was no preference for a single distribution pattern or intracellular compartment. For instance, a one-way repeated measures ANOVA revealed no significant differences between the intracellular distribution patterns for the XPC ($p>0.05$), XPA ($p>0.05$) and CSA ($p>0.05$) proteins. Therefore, after CAE treatment no one distribution pattern emerged as more significant that the other patterns for a given protein (Tukey-Kramer pairwise contrasts; $p>0.05$).

Figure 10:
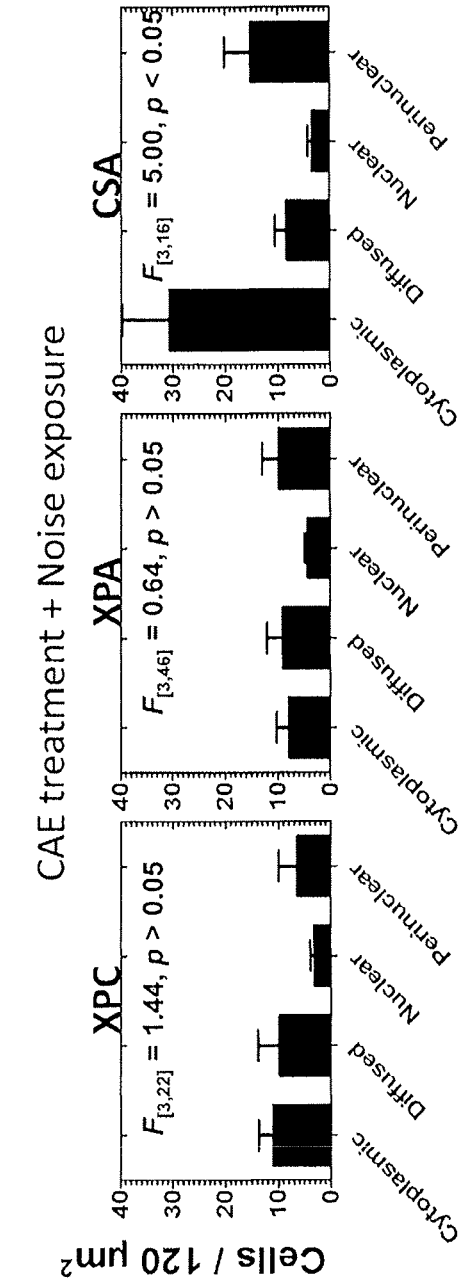
FIG. 10. Mixed allocation of repair proteins across subcellular compartments. The panels illustrate cell counts from the CAE+noise treated group (N=3). CAE+noise equalized the intracellular distribution of the XPC and XPA proteins. For instance, statistical analyses reveal that no one localization pattern is significantly different than the other patterns. However, the CSA protein exhibited a preference for cytoplasmic and perinuclear loci. Each bar represents mean±SEM.

FIG. 10 is an illustration of spiral ganglion cell counts as a function of distribution pattern following co-treatment with CAE and noise. The results appear as a merger between the results from the control and the CAE-only groups. For instance, similar to the CAE-only group, gradients in the cell counts for all three proteins could be detected. However, a one-way repeated measure ANOVA revealed no significant differences between the intracellular localization patterns for the XPC ($p>0.05$) and XPA ($p>0.05$) proteins. For each of these proteins no one distribution pattern emerged as more significant than the other patterns (Tukey-Kramer pairwise contrasts; $p>0.05$). The data for the CSA protein was similar to that of the control group. A one-way repeated measure ANOVA revealed significant differences between the intracellular distribution patterns ($p<0.05$). For instance, the cytoplasmic and perinuclear patterns were significantly higher than the other patterns (Tukey-Kramer pairwise contrasts; $p<0.05$).

Figure 11:
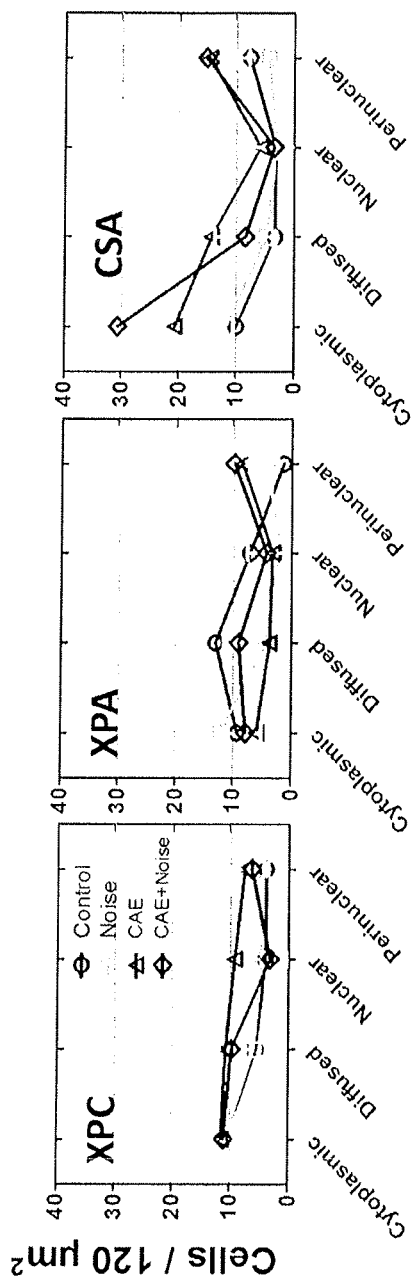
FIG. 11. The effect of the experimental conditions on the distribution patterns. The experimental conditions did not significantly change the distribution patterns for the XPC protein. However, there were significant changes for the XPA and CSA proteins. The experimental conditions were control (N=5), noise (N=5), CAE (N=3) and CAE+noise (N=3). Each plot displays the mean±SEM. Statistical analyses including pot-hoc test results are described in the text.

FIG. 11 reveals the effect of the four experimental conditions (control, noise exposed, CAE-only and CAE+noise) on the four distribution patterns (cytoplasmic, diffused, nuclear and perinuclear). One-way ANOVA testing on the mean number of XPC positive cells from each group revealed no significant ($p>0.05$) differences across distribution patterns. This implies that treatment condition does not affect the number of cells immunopositive for XPC regardless of subcellular distribution. However, ANOVA testing on the mean number of XPA positive cells from each group revealed significant ($p<0.01$) differences that were dependent on the distribution patterns. For instance, the cytoplasmic distribution pattern showed a significant (Tukey-Kramer pairwise contrasts; $p<0.05$) difference only between noise exposure and CAE-only treatment. The diffused distribution pattern exhibited significant differences between the groups (ANOVA; $p<0.01$). For instance, significant differences were evident between control and noise exposure (Tukey-Kramer pairwise contrasts; $p<0.01$) and between control and CAE-only treatment (Tukey-Kramer pairwise contrasts; $p<0.05$). Interestingly, the nuclear distribution pattern did not exhibit significant (ANOVA: $p>0.05$) differences between the groups. In contract, the perinuclear distribution pattern evidenced significant (ANOVA: $p<0.05$) differences between the groups and post host testing revealed that this difference was only evident between the control and CAE+noise groups (Tukey-Kramer pairwise contrasts; $p<0.05$). The combined results for XPA suggest that the number of cells immunopositive for XPA is affected by the treatment conditions and subcellular distribution.

Statistical testing on the mean number of CSA positive cells from each group revealed significant (ANOVA; $p<0.01$) differences in the number of cell exhibiting a cytoplasmic distribution pattern. For instance, Tukey-Kramer pairwise testing revealed significant difference between control and CAE ($p<0.01$), control and CAE+noise ($p<0.01$), noise and CAE ($p<0.05$), noise and CAE+noise ($p<0.01$) and CAE and CAE+noise ($p<0.05$). The diffused distribution pattern exhibited significant differences between the groups (ANOVA; $p<0.01$). For instance, significant differences were evident between control and CAE treatment (Tukey-Kramer pairwise contrasts; $p<0.01$) and between noise and CAE-only treatment (Tukey-Kramer pairwise contrasts; $p<0.05$). There were no significant differences between the groups for the other distribution patterns (Tukey-Kramer pairwise contrasts; $p>0.05$). In contrast, the nuclear distribution pattern did not exhibit significant (ANOVA: $p>0.05$) differences between the groups. However, the perinuclear distribution pattern evidenced significant (ANOVA: $p<0.01$) differences between the groups and Tukey-Kramer post host testing revealed differences between the control and noise groups ($p<0.01$), control and CAE groups ($p<0.05$), control and CAE+noise groups ($p<0.01$), noise and CAE group ($p<0.01$) and noise and CAE+noise groups ($p<0.05$). The combined results for CSA suggest that the number of cells immunopositive for CSA is affected by the treatment conditions and subcellular distribution.

Discussion

Under normal conditions neurons exhibit high intrinsic metabolic activity which necessitates intracellular reservoirs of DNA repair proteins [13]. In the current study spiral ganglion neurons were observed to compartmentalize DNA repair proteins in their nucleus, cytoplasm and at perinuclear loci. These three intracellular compartments were embodied by four intracellular distribution patterns. The four patterns were distinct and could be described as nuclear, cytoplasmic, diffuse (both nuclear and cytoplasmic) and perinuclear. The relevance of these patterns to individual spiral ganglion neurons is not known. However, each pattern has been reported previously within a variety of human and animal cell types. The nuclear pattern is characteristic of some neurons in the cerebral cortex, striatum, hippocampus and cerebellum [12]. It is believed that this pattern may increase DNA repair efficiency since the proteins are already localized in the nucleus [41],[9]. The cytoplasmic pattern is characteristic of some human neurons in the dentate gyrus and region CA4 of the hippocampus as well as several types of human cell lines [41],[42]. It is believed that cytoplasmic compartmentalization serves as a reservoir for the translocation of repair proteins to the nucleus when needed [14], [43]. Additionally, cytoplasmic repair proteins provide protection for nucleotide pools in the cytoplasm as well as mitochondrial DNA (mtDNA) [44]. This is important because cytoplasmic nucleotide pools (e.g., 2'-deoxyribonucleoside-5'-triphospates) are precursors to nuclear DNA (nDNA) and in the cytoplasm these precursors are particularly vulnerable to damage [45],[46]. The diffuse pattern is characteristic of some neurons in the substantia nigra, motor neurons of hypoglossal nucleus and neurons in the ventral tegmental area [12]. The benefit of this diffusion pattern is unresolved but it may allow for simultaneous protection of the nucleus and the cytoplasm. The perinuclear pattern has been demonstrated in human and animal fibroblast cells [47],[14]. Recent experiments have indicated that perinuclear localization reflects binding to mtDNA within mitochondria localized around the nucleus [7]. However, there is some evidence that perinuclear localization may reflect protein binding to the nuclear envelope with residual binding to the plasma membrane [41],[42]. Nevertheless, perinuclear repair proteins are believed to serve as a reservoir for both the nucleus and the cytoplasm.

Intracellular stress gradients are known to drive the spatial distribution of DNA repair proteins. For instance, nuclear localization indicates more localized stress in the nucleus and cytoplasmic localization indicates more localized stress in the cytoplasm [14],[48]. This phenomenon seems to be conserved because similar observations have been reported for *Saccharomyces cerevisiae* (yeast) under experimentally induced oxidative conditions [17],[10]. For instance when the nucleus of yeast cells is challenged by reactive oxygen species, DNA repair proteins from the cytoplasm translocate to the nucleus to protect nDNA. Conversely, when the cytoplasm is challenged by oxidative stress, DNA repair proteins in the nucleus translocate to the cytoplasm to defend cytoplasmic pools of DNA. These observations imply that the spatial remodeling of DNA repair proteins is dependent on oxidative demands on the cell.

It is known that noise exposure increases oxidative demands on spiral ganglion neurons [49]. In the current study noise exposure remodeled the endogenous compartmentalization of DNA repair proteins. For instance, under normal conditions the proteins were distributed such that each intracellular compartment was enriched with at least one repair protein. However, after noise exposure all three proteins were enriched in the cytoplasmic compartment. The relevance of this noise induced effect is not clear but is associated with neuronal threshold shifts of around 31 dB.

Treatment with CAE resulted in the enrichment of all three proteins in multiple intracellular compartments. Interestingly, this specific effect was associated with significant preservation of neural sensitivity following noise exposure.

In summary, the current study revealed for the first time that spiral ganglion neurons exhibit multiple compartmentalizing modes for DNA repair proteins and these modes were remodeled following noise stress and after DNA repair adjuvant therapy with CAEs. These findings are important because DNA repair proteins are necessary for protecting active genes and preserving cellular functions. Therefore, pharmacologic regulation of the intracellular localization of DNA repair proteins may represent a novel approach to preserving neural function following stress.

REFERENCES FOR EXAMPLE 2

1. Wood R D, Mitchell M, Lindahl T. Human DNA repair genes, 2005. Mutat Res. 2005; 577:275-283.
2. Fernandez-Capetillo O, Murga M. Why cells respond differently to DNA damage: a chromatin perspective. Cell Cycle. 2008; 7:980-983.
3. Köberle B, Roginskaya V, Wood R D. XPA protein as a limiting factor for nucleotide excision repair and UV sensitivity in human cells. DNA Repair 2006; 5:641-648.
4. Köberle B, Roginskaya V, Zima K S, Masters J R, Wood R D. Elevation of XPA protein level in testis tumor cells without increasing resistance to cisplatin or UV radiation. Mol Carcinog. 2008; 47:580-586.
5. Kang T H, Reardon J T, Sancar A. Regulation of nucleotide excision repair activity by transcriptional and post-transcriptional control of the XPA protein. Nucleic Acids Res. 2011; 39:3176-3187.
6. Guthrie O W, Li-Korotky H S, Durrant J D, Balaban C (2008) Cisplatin induces cytoplasmic to nuclear translocation of nucleotide excision repair factors among spiral ganglion neurons. Hear Res 239:79-91.
7. Mirbahai L, Kershaw R M, Green R M, Hayden R E, Meldrum R A, Hodges N J. Use of a molecular beacon to track the activity of base excision repair protein OGG1 in live cells. DNA Repair. 2010; 9:144-152.
8. Tell G, Crivellato E, Pines A, Paron I, Pucillo C, Manzini G, Bandiera A, Kelley M R, Di Loreto C, Damante G. Mitochondrial localization of APE/Ref-1 in thyroid cells. Mutat Res. 2001; 485:143-152.
9. Ahmad A, Enzlin J H, Bhagwat N R, Wijgers N, Raams A, Appledoorn E, Theil A F, J Hoeijmakers J H, Vermeulen W, J Jaspers N G, Scharer O D, Niedernhofer L J. Mislocalization of XPF-ERCC1 nuclease contributes to reduced DNA repair in XP-F patients. PLoS Genet. 2010; 6:e1000871.
10. Griffiths L M, Swartzlander D, Meadows K L, Wilkinson K D, Corbett A H, Doetsch P W. Dynamic compartmentalization of base excision repair proteins in response to nuclear and mitochondrial oxidative stress. Mol Cell Biol. 2009; 29:794-807.
11. Guthrie O W. Dys-synchronous regulation of XPC and XPA in trigeminal ganglion neurons following cisplatin treatment cycles. Anticancer Res. 2008; 2637-2640.
12. Yang S Z, Zhang Y F, Zhang L M, Huang Y L, Sun F Y. Immunohistochemical analysis of nucleotide excision repair factors XPA and XPB in adult rat brain. Anat Rec (Hoboken). 2008; 291:775-780.
13. Brooks P J. The case for 8,5'-cyclopurine-2'-deoxynucleosides as endogenous DNA lesions that cause neurodegeneration in xeroderma pigmentosum. Neuroscience. 2007; 145:1407-1417.
14. Seluanov A, Danek J, Hause N, Gorbunova V. Changes in the level and distribution of Ku proteins during cellular senescence. DNA Repair. 2007; 6:1740-8.
15. Swartzlander D B, Griffiths L M, Lee J, Degtyareva N P, Doetsch P W, Corbett A H. Regulation of base excision repair: Ntg1 nuclear and mitochondrial dynamic localization in response to genotoxic stress. Nucleic Acids Res. 2010; 38:3963-3974.
16. Jung Y, Lippard S J. Direct cellular responses to platinum-induced DNA damage. Chem Rev. 2007; 107:1387-1407.
17. Swartzlander D B, Griffiths L M, Lee J, Degtyareva N P, Doetsch P W, Corbett A H. Regulation of base excision repair: Ntg1 nuclear and mitochondrial dynamic localization in response to genotoxic stress. Nucleic Acids Res. 2010; 38:3963-3974.
18. Li Z, Musich P R, Zou Y. Differential DNA damage responses in p53 proficient and deficient cells: cisplatin-induced nuclear import of XPA is independent of ATR checkpoint in p53-deficient lung cancer cells. Int J Biochem Mol Biol. 2011; 2:138-145.
19. Kujawa S G, Liberman M C. Acceleration of age-related hearing loss by early noise exposure: evidence of a misspent youth. J Neurosci. 2006; 26:2115-2123.

20. Kujawa S G, Liberman M C. Adding insult to injury: cochlear nerve degeneration after "temporary" noise-induced hearing loss. J Neurosci. 2009; 29:14077-14085.
21. Akesson, C, Lindgren H, Pero R W, Leanderson T, Ivars F. An extract of *Uncaria tomentosa* inhibiting cell division and N F-kappa B activity without inducing cell death. Int. Immunopharmacol. 2003a; 3: 1889-1900.
22. Akesson C, Pero R W, Ivars F. C-Med 100, a hot water extract of *Uncaria tomentosa*, prolongs lymphocyte survival in vivo. Phytomedicine. 2003b; 10: 23-33.
23. Mammone T, Akesson C, Gan D, Giampapa V, Pero R W. A water soluble extract from *Uncaria tomentosa* (Cat's Claw) is a potent enhancer of DNA repair in primary organ cultures of human skin. Phytother Res. 2006; 20: 178-183.
24. Pero R W, Giampapa V, Vojdani A. Comparison of a broad spectrum anti-aging nutritional supplement with and without the action of a DNA repair enhancing cat's claw extract. J Anti Aging Med. 2002; 5: 345-355.
25. Pero R W, Amiri A, Sheng Y, Welther M, Rich M. Formulation and in vitro/in vivo evaluation of combining DNA repair and immune enhancing nutritional supplements. Phytomedicine. 2005; 12: 255-263.
26. Pero R W, Lund H, Leanderson T. Antioxidant metabolism induced by quinic acid. Increased urinary excretion of tryptophan and nicotinamide. Phytother Res. 2009; 23: 335-346.
27. Sheng Y, Bryngelsson C, Pero R W. Enhanced DNA repair, immune function and reduced toxicity of C-MED-100, a novel aqueous extract from *Uncaria tomentosa*. J Ethnopharmacol. 2000a; 69: 115-126.
28. Sheng Y, Pero R W, Wagner H. Treatment of chemotherapy-induced leukopenia in a rat model with aqueous extract from *Uncaria tomentosa*. Phytomedicine. 2000b; 7: 137-143.
29. Sheng Y, Li L, Holmgren K, Pero R W, DNA repair enhancement of aqueous extracts of *Uncaria tomentosa* in a human volunteer study. Phytomedicine. 2001; 8: 275-282.
30. Sheng Y, Akesson C, Holmgren K, Bryngelsson C, Giamapa V, Pero R W. An active ingredient of Cat's Claw water extracts identification and efficacy of quinic acid. J Ethnopharmacol. 2005; 96: 577-584.
31. Costa R M, Chigangas V, Galhardo Rda S, Carvalho H, Menck C F. The eukaryotic nucleotide excision repair pathway. Biochimie 2003; 85:1083-1099.
32. Hanawalt P C, Spivak G. Transcription-coupled DNA repair: two decades of progress and surprises. Nat Rev Mol Cell Biol 2008; 9:958-970.
33. Guthrie O W, Gearhart C A, Fulton S, Fechter L D. Carboxy alkyl esters of Uncariatomentosa augment recovery of sensorineural functions following noise injury. Brain Res. 2011; 1407:97-106.
34. Chen G D, Fechter L D. The relationship between noise-induced hearing loss and hair cell loss in rats. Hear Res. 2003; 177: 81-90.
35. Lorito G, Giordano P, Prosser S, *Martini* A, Hatzopoulos S. Noise-induced hearing loss: a study on the pharmacological protection in the Sprague Dawley rat with N-acetyl cysteine. Acta Otorhinolaryngol Ital. 2006; 26, 133-139.
36. Guthrie O W, Carrero-Martinez F A. Real-time quantification of Xeroderma pigmentosum mRNA from the mammalian cochlea. Ear Hear. 2010; 31:714-721.
37. Mirkin N, Fonseca D, Mohammed S, Cevher M A, Manley J L, Kleiman F E. The 3' processing factor CstF functions in the DNA repair response. Nucleic Acids Res 2008; 36:1792-1804
38. Gospodinov A, Ivanov R, Anachkova B, Russev G. Nucleotide excision repair rates in rat tissues. Eur J Biochem. 2003; 270:1000-1005.
39. Kasahara T, Kuwayama C, Hashiba M, Harada T, Kakinuma C, Miyauchi M, Degawa M. The gene expression of hepatic proteins responsible for DNA repair and cell proliferation in tamoxifen-induced hepatocarcinogenesis. Cancer Sci. 2003; 94:582-588.
40. Guthrie O W. DNA repair proteins and telomerase reverse transcriptase in the cochlear lateral wall of cis-platin-treated rats. J Chemother. 2009; 21:74-79.
41. Youssoufian H. Localization of Fanconi anemia C protein to the cytoplasm of mammalian cells. Proc Natl Acad Sci USA. 1994; 91:7975-7979.
42. Duguid J R, Eble J N, Wilson T M, Kelley M R. Differential cellular and subcellular expression of the human multifunctional apurinic/apyrimidinic endonuclease (APE/ref-1) DNA repair enzyme. Cancer Res. 1995; 55:6097-6102.
43. Knudsen N O, Andersen S D, Liitzen A, Nielsen F C, Rasmussen L J. Nuclear translocation contributes to regulation of DNA excision repair activities. DNA Repair. 2009; 8:682-689.
44. Rai P. Oxidation in the nucleotide pool, the DNA damage response and cellular senescence: Defective bricks build a defective house. Mutat Res. 2010; 703:71-81.
45. Hudson E K, Hogue B A, Souza-Pinto N C, Croteau D L, Anson R M, Bohr V A, Hansford R G. Age-associated change in mitochondrial DNA damage. Free Radic Res. 1998; 29:573-579.
46. Santos J H, Mandavilli B S. Measuring oxidative mtDNA damage and repair using quantitative PCR. Van Houten B. Methods Mol Biol. 2002; 197:159-176
47. Cool B L, Sirover M A. Immunocytochemical localization of the base excision repair enzyme uracil DNA glycosylase in quiescent and proliferating normal human cells. Cancer Res. 1989; 49:3029-3036.
48. Frossi B, Tell G, Spessotto P, Colombatti A, Vitale G, Pucillo C. H(2)O(2) induces translocation of APE/Ref-1 to mitochondria in the Raji B-cell line. J Cell Physiol. 2002; 193:180-186.
49. Xiong M, He Q, Lai H, Wang J. Oxidative stress in spiral ganglion cells of pigmented and albino guinea pigs exposed to impulse noise. Acta Otolaryngol. 2011; 131: 914-920.

Example 3

Materials and Methods
Animals and Experimental Design

Experiments were conducted on male Long-Evans rats (250-300 g) that were acquired from Harlan Laboratories, Inc. (Livermore, Calif. USA). All experimental protocols were approved by the Institutional Animal Care and Use Committee at the Loma Linda Veteran's Affairs Hospital. A total of 48 animals were used in the experiments. After arriving at the vivarium, the animals were allowed to acclimate for one week. Baseline distortion product otoacoustic emissions (DPOAE) were then collected on each animal to verify cochlear function. The animals were assigned to one of four groups based on their DPOAE recordings in order to counterbalance cochlear function between the groups. The four groups included a CAE group (n=10), a noise+CAE group (n=11), a control group (n=14) and a noise exposure group (n=13). A formulation of CAE that has been standardized to increase DNA repair activity was prepared by Optigenex Inc. (Hoboken, N.J. USA) as reported previously (Guthrie et al., 2011; Sheng et al., 2005). The animals in the CAE and CAE+noise groups were administered 160 mg/kg of CAE by gastric gavage for 28 consecutive days (Guthrie et al., 2011; Sheng et al, 2000a). The control group was also treated via gastric gavage with distilled water (dissolving agent for CAE) for 28 consecutive days. The noise group did not receive any treatment beyond being exposed to the nose dose (see below). Noise exposure of the noise and CAE+noise groups occurred on the 29th day (one day after the 28 days of water or CAE treatment). Then post-exposure DPOAE measurements and tissue harvesting were conducted from each group on the 30th day (1-day after the noise exposure). Tissues were harvested to evaluate whether or not γ-H2Ax expression increased in the organ of *Corti* after noise exposure and whether or not CAE treatment could reduce the expression of γ-H2Ax in the organ of *Corti* at an early time point (1-day post trauma) after the exposure. To evaluate whether a putative effect on γ-H2Ax expression is associated with long-term recovery of cochlear function, some of the animals were allowed to survive for 4 weeks post-noise exposure and cochlear function was evaluated again with DPOAE. Table 3 describes the different animal groups, their treatment regimen and the experimental design.

TABLE 3

Experimental design.

| Groups | Baseline DPOAE Day 0 | CAE treatment 28 days of treatment | Noise Day 29 | DPOAE + Sacrifice Day 30 | DPOAE recovery 1-week and 4-week post-noise |
|---|---|---|---|---|---|
| Control | (N = 14) | water | | + | (N = 9) |
| Noise | (N = 13) | | noise | + | (N = 8) |
| CAE | (N = 10) | CAE | | + | |
| Noise + CAE | (N = 11) | CAE | noise | + | (N = 6) |

Abbreviations:
CAE, Carboxy alkyl esters;
DPOAE, distortion product otoacoustic emissions.

Distortion Product Otoacoustic Emissions (DPOAE)

The cubic $2f_1-f_2$ DPOAE is particularly sensitive to cochlear noise damage. Therefore DPOAEs ($2f_1-f_2$ level as a function of increasing stimulus frequency, commonly referred to as a DP-gram) were recorded as described previously (Guthrie and Xu, 2012). Briefly, each animal was anesthetized with ketamine/xylazine (44/7 mg/kg, im.) while normal body temperature was maintained using a direct current (dc) heating unit built into the surgical table. The cubic $2f_1-f_2$ DPOAE was recorded with two primaries, $f_2$ and $f_1$; where $f_2$ is higher than $f_1$ at an $f_2/f_1$ ratio of 1.25. The primaries (L) were presented in 0.1-octave increments from 3.2 to 63 kHz. The levels of the primaries were set to $L_1-10=L_2$ as indicated in the figures. The frequency and level ratios of the primaries were selected to maximize the $2f_1-f_2$ SPL recorded from the ear canal (Whatehead et al., 1995a, 1995b, and 1995c). A customized signal presentation, acquisition and analysis program written in LabVIEW version 7.1 (National Instruments, Austin, Tex. USA) was used to drive a PCI-4461 computer-based DSP board (National Instruments, Austin, Tex., USA) for generation of the primaries and Fourier analysis of the response.

Noise Exposure

Both the noise-only group and the CAE+noise group were exposed in the same noise exposure chamber at the same time. The noise exposure paradigm has been described previously (Guthrie et al., 2011). Briefly, the animals were exposed to an octave band of noise (OBN) centered at 8 kHz. The intensity of the noise was 105 dB SPL and the duration was 4 hours. The animals were awake during the exposure and were free to move around in a wire-cloth enclosure within a 40 L noise chamber. The noise was generated by a Function Generator (Sanford Research System, Menlo Park, Calif. USA) coupled to a Frequency Device (Frequency Device Inc., Haverhill, Mass. USA). Vifa D25AG-05 speakers (Vifa International A/S, Videbaek, Denmark) located approximately 5 cm above the animals' wire-cloth enclosure was used to present the noise. The frequency spectrum of the noise was verified in the noise chamber containing the rats with a sound level meter (Quest Electronics, Oconomowoc, Wis. USA) close to the animals' pinnae.

Immunolabeling

Animal and Tissue Preparation

Immunolabeling of γ-H2Ax within cells in tissue sections is a standard method of detecting DSB (Wang et al., 2009; Redon et al., 2011; Redon et al., 2012). Therefore, we employed γ-H2Ax immunolabeling and quantification to determine differences between the groups. Twenty anesthetized animals (control group=5, noise group=5, CAE group=5 and CAE+noise group=5) were sacrificed by transcardial perfusion with phosphate-buffered saline (PBS; 10 mM, pH 7.4) followed by periodate-lysine-paraformaldehyde fixative (Guthrie, 2008a). The heads were then removed, skinned and post-fixed in 4% paraformaldehyde overnight at 22° C. Formic acid (10%) was used for chemical decalcification of the heads as described previously (Guthrie and Xu, 2012). Then the heads were paraffin embedded and sectioned at 5 μm in the midmodiolar plane. The sections were incubated in a heated water bath and mounted on subbed slides for immunolabeling. Kidney tissues were simultaneously harvested, postfixed, paraffin embedded, sectioned and mounted on subbed slides.

Immunoperoxidase Procedure

Tissue sections were de-paraffinized in zylene, hydrated in graded ethyl alcohol and water then incubated in 0.9% $H_2O_2$ for 10 minutes. They were then heated for 20 minutes at 90-98° C. in a low pH (0.80-3.06) sodium citrate-citric acid buffer (antigen retrieval) and then rinsed thoroughly with PBS. Afterwards, the sections were pre-treated with a blocking solution of normal goat serum, 10% Triton X-100 and 2% bovine serum albumin (BSA; Sigma, St. Louis, Mo., USA) in PBS for 1 hour. The primary antibody was diluted in the blocking solution at a 1:100 concentration. The primary antibody (anti-γ-H2Ax, Ser139) is commercially available (Santa Cruz Biotechnology, Inc., Santa Cruz, Calif. USA). The specificity of the antibody has been confirmed previously (Verma et al., 2010; Li et al., 2011; Gupta, et al., 2011). Nevertheless, negative control experiments were conducted such that sections were incubated with blocking serum without the primary antibody (Guthrie et al., 2008). Such negative control sections were processed at the same time as the experimental sections and received simultaneous and identical treatments. Furthermore, positive control experiments were conducted by immunolabeling tissue that is known to exhibit constitutive expression of γ-H2Ax (Dmitrieva et al., 2004; see FIG. 12). After incubating the sections with the primary antibody (or blocking serum for negative control sections) for 48 hours at 4° C., the sections were rinsed with PBS. They were then treated with a biotinylated anti-rabbit secondary antibody (Vector Laboratories, Temecula, Calif. USA) diluted 1:100 in PBS+2% BSA for 24 hours at 4° C. The sections were then rinsed in PBS, incubated with preformed avidin-biotin-peroxidase enzyme complexes (Vectastain ABC reagent; Vector Laboratories, Inc., Burlingame, Calif. USA) for one hour, rinsed again with PBS and then treated with a solution of Trizma pre-set crystals (1.58 g; Sigma-Aldrich, St. Louis, Mo. USA) to stabilize peroxidase enzyme reactions. The peroxidase enzyme complexes were then used to oxidize 3,3'-diaminobenzidine tetrahydrochloride to produce a brown chromogen.

Quantitative Morphometry

Equipment.

A Leica DM2500 upright microscope (Leica Microsystems Inc., Bannockburn, Ill. USA) was used for brightfield microscopy. A ProgRes® CF$^{scan}$ digital camera (JENOPTIK Laser, Jena, Germany) mounted on the Leica DM2500 was used for digital image capturing. Image-Pro® plus version 6.3 (Media Cybernetics Inc., Bethesda, Md., USA) for Windows™ was used to control image capturing, pixel thresholding and bitmap analyses. A Dell Optiplex GX620 with an Intel Core2 processor was used for software operations.

Photomicroscopy.

The microscope current drain, light source and temperature were standardized to ensure accurate and consistent reading of each tissue section. The intensity of the light to a 1.4 megapixel charged-coupled-device color sensor was monitored over an 8 hour period by capturing a blank field (cover slip, mounting media and glass slide). The light intensity fluctuated by only 0.1% (a modest difference in mean gray value of 0.2748) within the first hour of being turned on then stabilized when the lamp housing reached a temperature of 62±1° C. All photomicrographs were taken when the microscope light intensity stabilized. To further ensure consistent spatial and temporal illumination for each tissue section during microscopy, the mean gray value (g) for blank fields adjacent to each tissue section was maintained at ≥254 g. In addition to providing consistent illumination, this high level illumination had the added advantage of masking background staining which was significantly lighter (light brown stain) than the antibody staining which exhibited a heavy brown stain and thus unmasked by the illumination. Photomicrographs of the organ of *Corti* were taken with an N-PLAN 40x/0.65 objective lens. These photomicrographs (680×512 pixels) were saved in uncompressed tagged-image file format for later retrieval. They were then converted from 48 bits/pixel to 24 bits for subsequent analyses. To further remove background staining from each photomicrograph a predetermined threshold criterion was applied via Image-Pro's threshold algorithm. This threshold criterion was empirically determined from pilot experiments. For instance, the acellular tectorial membrane of *Corti*'s organ is sometimes stained after the immunolabeling procedure. This is due to the trapping of the secondary antibody within the microfibrillar matrix of the tectorial membrane and the failure of wash steps to completely dislodge the secondary antibody. The thresholding criteria employed in this study was trained on masking background levels of staining such as the level of background found in the tectorial membrane. Therefore, applying the threshold criteria increased the signal-to-noise ratio. After thresholding, an area of interest (AOI) field was selected within each organ of *Corti*. Bitmap readings were then taken within the AOI. The bitmaps record the positional matrix ($n_1 \times n_1$) and brightness (b) of each primary colored (red, green and blue or RGB) pixel ($n_1 \times n_1 \times 3$). These bitmap readings were then used in the determination of absolute chromogen levels by the cumulative signal strength technique.

Cumulative Signal Strength.

Cumulative signal strength is an objective technique that quantifies the absolute amount of immunolabeling (staining intensity) in photomicrographs (Matkowskyj et al., 2000; Matkowskyj et al., 2003). This is achieved by measuring the mathematical energy (E) within each $n_1 \times n_1 \times 3$ pixel of an $N_1 \times N_1 \times 3$ photomicrograph. The computation is as follows (Hu et al., 2008);

$$E = \sqrt{\frac{1}{N_1 N_2} \sum_{n_1=1}^{N_1} \sum_{n_2=1}^{N_2} [I_R(n_1, n_2)]^2} + \sqrt{\frac{1}{N_1 N_2} \sum_{n_1=1}^{N_1} \sum_{n_2=1}^{N_2} [I_G(n_1, n_2)]^2} + \sqrt{\frac{1}{N_1 N_2} \sum_{n_1=1}^{N_1} \sum_{n_2=1}^{N_2} [I_B(n_1, n_2)]^2} \quad (1)$$

where $I_i(n_1,n_2)$ is the energy from a particular hue (i=R, G or B) at position $n_1 \times n_2$ in the AOI frame. In photomicrographs from bright field microscopy $I_i(n_1,n_2)=255-b_i(n_1,n_2)$, where b is the brightness value or gray value. The E that reflects specific staining of the γ-H2Ax antibody ($E_{\gamma-H2Ax}$) is the absolute value of the difference between antibody induced immunolabeling ($E_{antibody[+]}$) and that induced by the absence of the antibody ($E_{antibody[-]}$) also known as the negative control;

$$E_{\gamma-H2Ax} = (E_{antibody[+]}) - (E_{antibody[-]}) \quad (2)$$

Statistical Analysis

Statistical analyses were conducted with Prism 5, version 5.03 (GraphPad Software, Inc., La Jolla, Calif. USA). The DPOAE data was analyzed for group effects such that analysis of variance (ANOVA) testing was conducted on $2f_1-f_2$ DPOAE levels to determine significant differences between the groups. Post-hoc testing employed Dunnett's paired comparison analyses. The intensity of γ-H2Ax immunolabeling was recorded from midmodiolar cochlear sections. For each animal, duplicate readings were recorded and 10 cochlear sections were used for each group (a total of 40 sections). The apical, middle and basal cochlear coils were evident in the sections therefore, 120 (40×3) cochlear coils were studied. Statistical differences between groups were determined with ANOVA and Bonferroni's multiple comparison testing.

Results

γ-H2Ax Labeling

Figure 12:
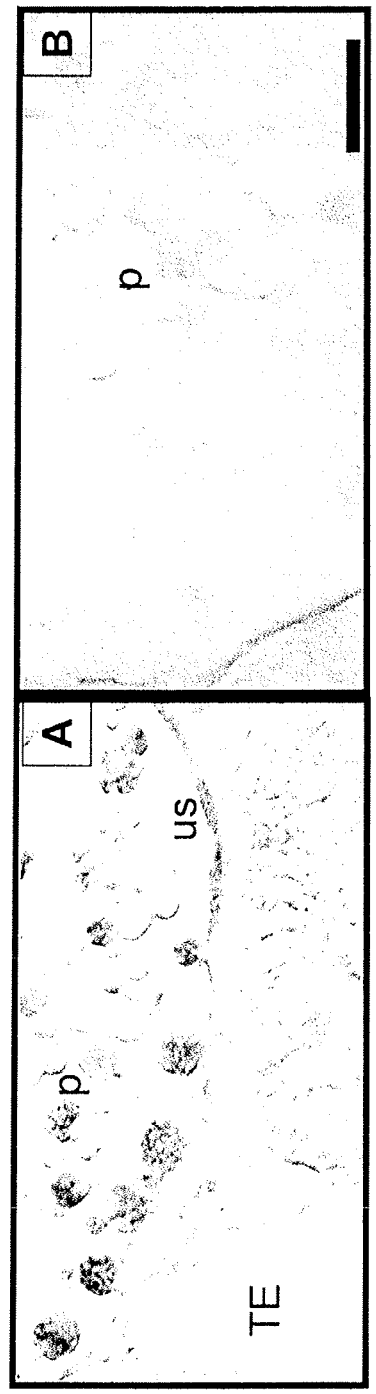
FIG. 12. γ-H2Ax labeling in kidney. Panel A shows γ-H2Ax immunolabeling in the Long-Evans rat kidney (positive control). A few podocytes (P) that line the urinary space (US) are labeled while other podocytes are not labeled. The tubular epithelia (TE) in panel A shows little or no staining. Panel B reveals that omitting the antibody from the immunolabeling procedure resulted in no staining within podocytes (negative control). The scale bar (20 µm) in panel B applies to panel A.
Figure 13:
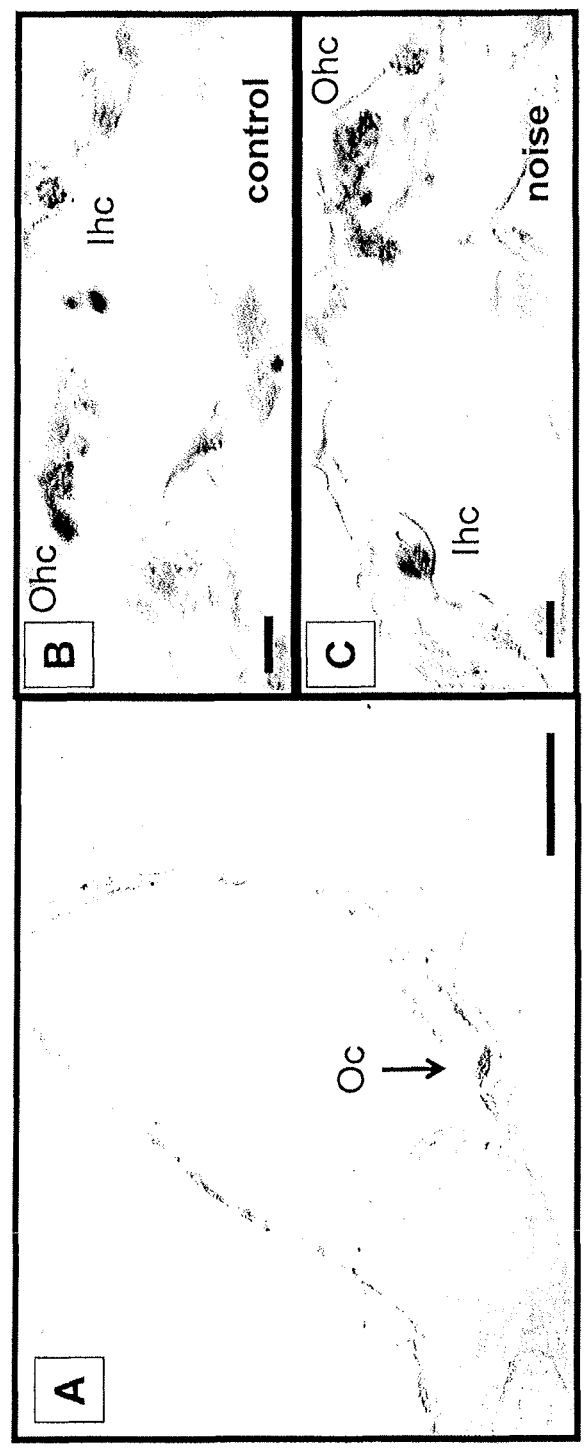
FIG. 13. γ-H2Ax labeling in scala media. Panel A shows that several structures are labeled but the most prominent is the organ of Corti. γ-H2Ax labeling can be detected in the organ of Corti with (panel C) and without (panel B) noise exposure. The labeling is predominantly localized in hair cells and supporting cells. Abbreviations: Oc, organ of Corti; Ohc, outer hair cell; Ihc, inner hair cell. The scale bar in panel A is 100 µm and the scale bars in panels B and C are 10 µm.

It is known that the kidney exhibit consistent immunolabeling of γ-H2Ax which is believed to represent DSB that form in noncoding regions of the genome called gene deserts (Dmitrieva et al., 2011; Dmitrieva et al., 2004). Therefore, kidney sections (FIG. 12) served as positive and negative controls for the immunolabeling experiments. FIG. 12A reveals γ-H2Ax labeling in podocytes of the renal corpulse (positive control). This labeling was abolished when the antibody is omitted from the immunolabeling procedure (FIG. 12B, negative control). Immunolabeling for γ-H2Ax was also detected within the organ of Corti. The labeling was present under normal (control) conditions and after noise or CAE treatment. FIG. 13A is a representative example of the staining. Several cochlear structures are labeled but labeling in the organ of Corti is particularly prominent. Panels B and C from FIG. 13 demonstrates that γ-H2Ax labeling could be detected within hair cells and supporting cells with and without noise exposure. This persistent expression of γ-H2Ax is consistent with previous research that has shown persistent expression of DNA repair proteins in the organ of Corti (Guthrie, 2008b; Guthrie, 2009; Guthrie and Carrero-Martinez, 2010).

γ-H2Ax Levels

Figure 14:
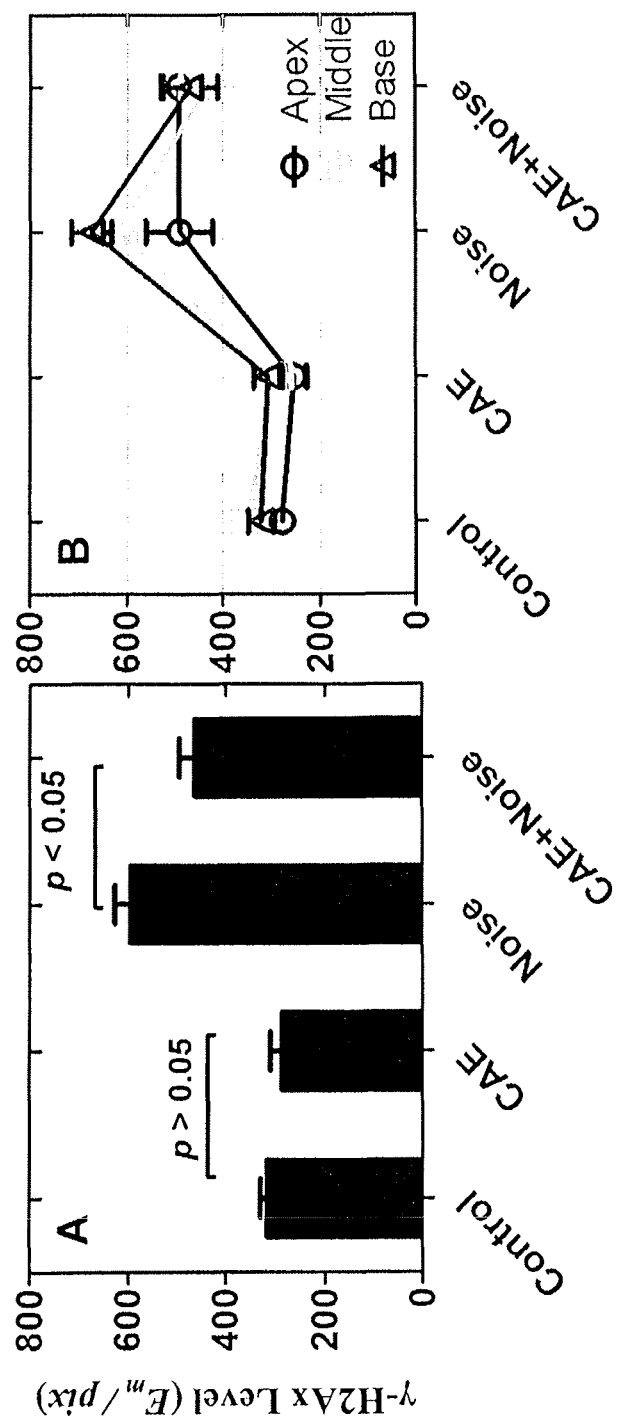
FIG. 14. γ-H2Ax levels within the organ of Corti. γ-H2Ax levels were quantified in mathematical energy units per pixel ($E_m$/pix) and displayed in panels A-B as a function of the treatment conditions. Note that there were no significant differences in γ-H2Ax level between the control and CAE conditions. However, there was a marked increase after noise or co-treatment with CAE and noise. The level of γ-H2Ax is significantly lower in the CAE+noise condition relative to the noise-only condition. This effect is further supported in Panel B where γ-H2Ax levels for individual cochlear turns were quantified. Errors bars are standard errors of the means.

The prominence of γ-H2Ax labeling in the organ of Corti made it difficult to make subjective judgments on the level of expression between the groups. Therefore, to determine differences in staining intensity, the level of γ-H2Ax in the organ of Corti was quantified by determining the absolute amount of chromogen per pixel by employing the cumulative signal strength technique (Matkowshyj et al., 2000; Matkowskyj et al., 2003; Hu et al., 2008). This technique measures the signal energy as a function of pixel, where energy is defined in the mathematical sense. Therefore, the values are unit less and thus reported as mathematical energy units per pixel ($E_M$/pix). FIG. 14A reveals that γ-H2Ax level in the control group was similar to that in the CAE group. However, noise exposure induced an increase in γ-H2Ax. This increase was also observed after co-treatment with CAE and noise. Note that γ-H2Ax level was lower in the CAE+noise treated group relative to that in the noise-only group. FIG. 14B reveals γ-H2Ax levels for each cochlear turn (apical, middle and basal coils) as a function of the treatment groups. In all cochlear turns, γ-H2Ax levels were similar between the control and CAE groups. However, γ-H2Ax levels were highest among the noise and CAE+noise groups. In the middle and basal turn γ-H2Ax levels were higher in the noise group compared to the CAE+noise group. Therefore, inspection of individual cochlear turns further supported the notion that CAE treatment reduced noise induced levels of γ-H2Ax.

Statistical analyses were conducted on γ-H2Ax level measurements. A one-way ANOVA where treatment condition served as a between subjects factor revealed that there was a statistically significant difference in γ-H2Ax levels between the four groups ($F_{[3,36]}$=30.33, p<0.01). Bonferroni pairwise contrast revealed no statistically significant differences between the control and CAE groups (p>0.05). But these groups exhibited significantly lower γ-H2Ax levels compared to the noise exposed group (p<0.01). Furthermore, the noise exposed group exhibited significantly higher γ-H2Ax levels compared to the CAE+noise group (p<0.05). These statistical calculations suggest that CAE treatment reduced noise induced γ-H2Ax within the organ of Corti. This conclusion was further supported by statistical calculations on γ-H2Ax level measurements from individual cochlear turns. For instance, the control and CAE group showed no significant difference (p>0.05) in γ-H2Ax levels regardless of cochlear turn (apical, middle or basal). However, the noise group and the CAE+noise group were significantly (p<0.05) different at the basal and middle turns. In these cochlear turns, γ-H2Ax was significantly (p<0.05) lower within the CAE+noise group. The pooled results indicate that CAE treatment reduced noise induced γ-H2Ax levels in the basal and middle cochlear turns. This is significant because basalward turns are known to be more vulnerable to cell death and the loss of cochlear function after exposure to the same noise dose used in the current study (Guthrie et al., 2011).

Protection from Noise Injury

Figure 15:
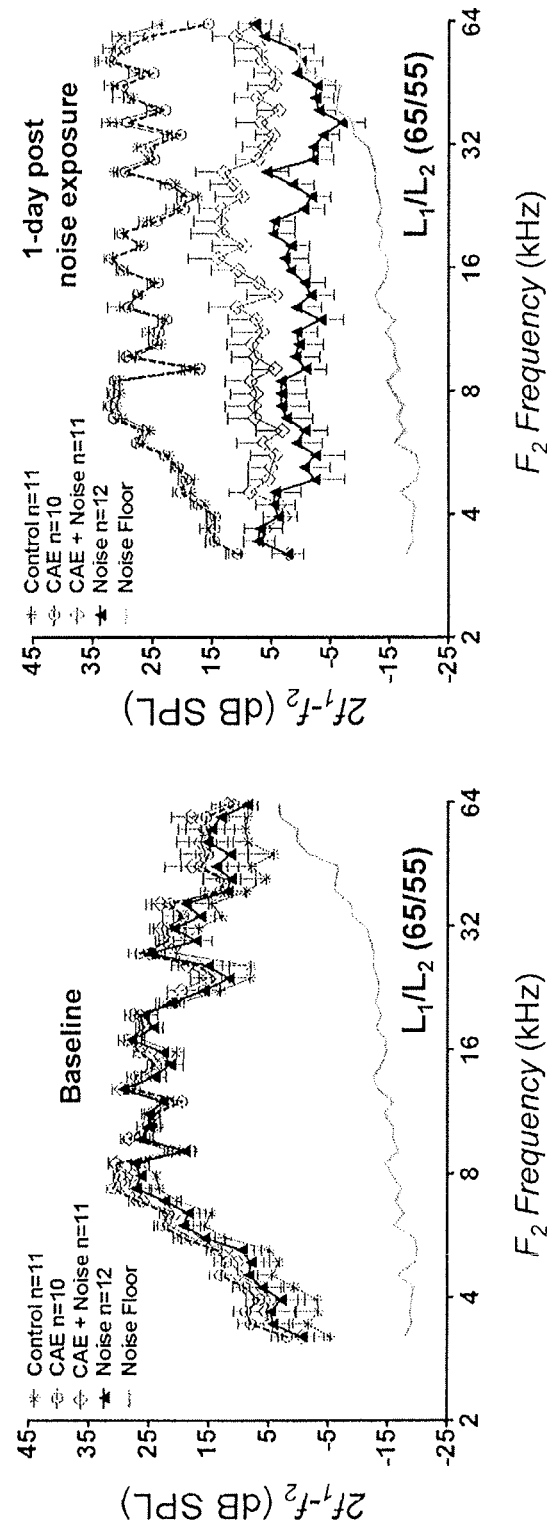
FIG. 15. Protection from noise injury. The levels of $2f_1-f_2$ as a function of $f_2$ frequency (DP-gram; $L_1/L_2$=65/55) are shown for each treatment group at baseline and 1 day post-noise exposure. The vertical gray bar in this and all figures represent the frequency range of the damaging noise. Both the noise-only group and the CAE+noise group were exposed in the same noise exposure chamber at the same time. Note that the CAE+noise group exhibited better (higher) levels than the noise only group at 1 day post-noise exposure. Errors bars are standard errors of the means.

To evaluate protection from noise injury, DP-grams of $2f_1-f_2$ were recorded. These recordings were obtained at baseline and 1 day following noise exposure. FIG. 15 shows the response of $2f_1-f_2$ DPOAE as a function of $f_2$ frequency driven with primary levels (L) at 65/55 dB SPL. Baseline recordings revealed that all groups had large $2f_1-f_2$ levels that exceeded the noise floor by at least 6 dB. At 1 day post-noise exposure, the control groups (vehicle-control and CAE treated groups) showed equivalent $2f_1-f_2$ levels (two-way ANOVA: $F_{[1,43]}$=2.09, p>0.05). However there was a significant difference (two-way ANOVA: $F_{[1,43]}$=56.37, p<0.01) between the noise treated groups where the CAE+noise group exhibited higher (better) levels than the noise-only group. Furthermore, the highest frequency components (>32 kHz) of the noise-only group was suppressed into the noise floor (average=1.27 dB above noise floor) while that of the CAE+noise group remained above the noise floor (average=7.31 dB above noise floor). These findings suggest that $2f_1-f_2$ DPOAE levels from the CAE+noise group was better preserved than that of the noise group as early as 1 day post-noise exposure.

Recovery from Noise Injury

Figure 16:
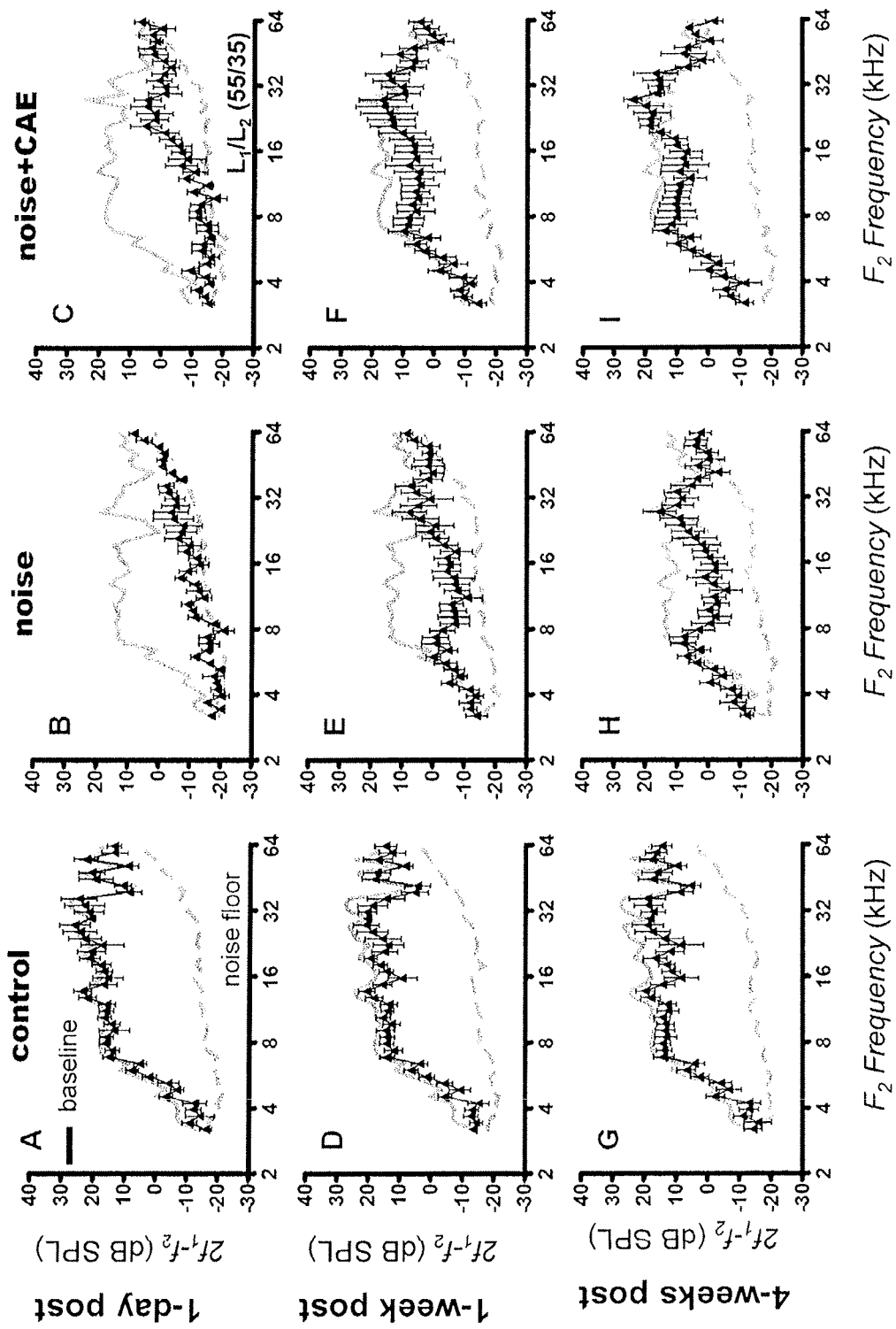
FIG. 16. Recovery from noise injury. DP-grams ($L_1/L_2$=55/35) obtained at 1 day, 1 week and 4 weeks post noise exposure are illustrated for the control, noise and CAE+ noise groups. Both the noise-only group and the CAE+noise group were exposed in the same noise exposure chamber at the same time. Note that the CAE treated group showed faster recovery than the noise exposure group.

Recordings of the $2f_1-f_2$ DPOAE were conducted out to 4 weeks post-noise exposure to evaluate functional recovery from the noise exposure. The stimulus primary levels were set at 55/35 ($L_1/L_2$) which increases the sensitivity of the $2f_1-f_2$ recordings (Avan et al., 2003). FIG. 16 illustrates the change in $2f_1-f_2$ levels for three time points (1-day, 1-week and 4-weeks post noise exposure). In the control group, $2f_1-f_2$ levels were robust and exhibited modest variations between time points. However, in the noise exposed group there was wide-spread loss of $2f_1-f_2$ levels at 1 day post exposure. For instance, the $2f_1-f_2$ DPOAE levels were reduced to approximate the noise floor over the entire $f_2$ frequency range. At 1 week post-noise exposure there was some recovery in $2f_1-f_2$ levels but the frequency range between ~8-24 kHz showed prominent loss. At 4 weeks post-noise exposure there was still a prominent loss in the ~8-24 kHz range. These results indicate that the noise exposure resulted in permanent loss 1½-octave above the center frequency (8 kHz) of the OBN. Indeed, permanent cochlear loss in Long-Evans rats exposed to an 8 kHz OBN at 105 dB SPL for 4 hours typically occurs at 4 weeks post-exposure (Chen and Fechter, 2003; Lorito et al., 2006).

The capacity of the CAE+noise group to recover from noise injury is shown in FIG. 16. At 1 day post-noise exposure the CAE+noise group showed loss of $2f_1-f_2$ levels. For instance, frequencies below ~16 kHz were suppressed in to the noise floor. However, high frequencies between ~16-32 kHz were not reduced into the noise floor which is in contrast with the noise-only treatment where the entire frequency spectrum was suppressed into the noise floor. These data support that of FIG. 15 in suggesting that CAE may provide early protection against noise injury. Indeed, at only 1 week post-noise exposure the CAE+noise group showed recovery while the noise-only group still exhibited a prominent loss. One week following noise exposure is considered an early time point because functional recovery is still occurring. Interestingly, the CAE+noise group showed almost complete recovery of $2f_1-f_2$ levels at 4 weeks post-noise exposure. This indicates that the CAE treated group was able to recover from the noise exposure.

Statistical analyses were conducted on the $2f_1-f_2$ levels obtained at 4 weeks post noise exposure. A one-way ANOVA revealed significant ($F_{[2,129]}$=11.17, p<0.01) main effects for the groups. Dunnett's multiple comparison testing demonstrated that there was a statistically significant (p<0.01) difference between the control and noise groups but there was no significant (p>0.05) difference between the control and CAE+noise groups.

REFERENCES FOR EXAMPLE 3

Akesson, C., Lindgren, H., Pero, R. W., Leanderson, T., Ivars, F., 2003a. An extract of *Uncaria tomentosa* inhibiting cell division and N F-kappa B activity without inducing cell death. Int. Immunopharmacol. 3, 1889-900.

Akesson C, Pero R W, Ivars F., 2003b. C-Med 100, a hot water extract of *Uncaria tomentosa*, prolongs lymphocyte survival in vivo. Phytomedicine. 10: 23-33.

Avan P, Bonfils P, Gilain L, Mom T. 2003. Physiopathological significance of distortion-product otoacoustic emissions at 2f1–f2 produced by high-versus low-level stimuli. J Acoust Soc Am. 113: 430-441.

Chen G D, Fechter L D., 2003. The relationship between noise-induced hearing loss and hair cell loss in rats. Hear Res. 177: 81-90.

Crowe, S. L., Movsesyan, V. A., Jorgensen, T. J., Kondratyev, A., 2006. Rapid phosphorylation of histone H2A.X following ionotropic glutamate receptor activation. Eur J Neurosci 23, 2351-1361.

Dmitrieva N I, Cai Q, Burg M B. 2004. Cells adapted to high NaCl have many DNA breaks and impaired DNA repair both in cell culture and in vivo. Proc Natl Acad Sci USA. 101: 2317-2322.

Dmitrieva N I, Cui K, Kitchaev D A, Zhao K, Burg M B., 2011. DNA double-strand breaks induced by high NaCl occur predominantly in gene deserts. Proc Natl Acad Sci USA. 108:20796-20801.

Firsanov D, Vasilishina A, Kropotov A, Mikhailov V., 2012. Dynamics of γH2AX formation and elimination in mammalian cells after X-irradiation. Biochimie. 94: 2416-2422.

Frenzilli, G., Lenzi, P., Scarcelli, V., Fornai, F., Pellegrini, A., Soldani, P., Paparelli, A., Nigro, M., 2004. Effects of loud noise exposure on DNA integrity in rat adrenal gland. Environ Health Perspect, 112:1671.

Fryatt, A. G., Mulheran, M., Egerton, J., Gunthorpe, M. J., Grubb, B. D.,2011. Ototrauma induces sodium channel plasticity in auditory afferent neurons. Mol Cell Neurosci 48, 51-61.

Ghabili, K., Shoja, M. M., Tubbs, R. S., Rahimi-Ardabili, B., Ansarin, K., 2007. Sonocarcinogenesis: loud noise may cause malignant transformation of cells. Med Hypotheses 69, 1156.

Gupta, K., Chakrabarti, A., Rana, S., Ramdeo, R., Roth, B. L., Agarwal, M. L., Tse, W., Agarwal, M. K., Wald, D. N., 2011. Securinine, a myeloid differentiation agent with therapeutic potential for AML. PLoS One 6, e, 21203.

Guthrie O W, Xu H., 2012. Noise exposure potentiates the subcellular distribution of nucleotide excision repair proteins within spiral ganglion neurons. Hear Res. 294: 21-30.

Guthrie O W, Gearhart C A, Fulton S, Fechter L D. 2011. Carboxy alkyl esters of *Uncaria tomentosa* augment recovery of sensorineural functions following noise injury. Brain Res. 1407:97-106.

Guthrie O W, Carrero-Martinez F A., 2010. Real-time quantification of Xeroderma pigmentosum mRNA from the mammalian cochlea. Ear Hear. 31: 714-721.

Guthrie O W., 2009. DNA repair proteins and telomerase reverse transcriptase in the cochlear lateral wall of cisplatin-treated rats. J Chemother. 21: 74-79.

Guthrie O W., 2008a. Dys-synchronous regulation of XPC and XPA in trigeminal ganglion neurons following cisplatin treatment cycles. Anticancer Res. 2637-2640.

Guthrie O W., 2008b. Preincision complex-I from the excision nuclease reaction among cochlear spiral limbus and outer hair cells. J Mol Histol. 39:617-625.

Guthrie O W., 2008c. Aminoglycoside induced ototoxicity. Toxicology, 249(2-3):91-96.

Guthrie O W, Li-Korotky H S, Durrant J D, Balaban C., 2008. Cisplatin induces cytoplasmic to nuclear translocation of nucleotide excision repair factors among spiral ganglion neurons. Hear Res. 239, 79-91.

Han, W., Shi, X., Nuttall, A. L., 2006. AIF and endoG translocation in noise exposure induced hair cell death. Hear Res 211, 85-95.

Hatahet, Z., Purmal, A. A., Wallace, S. S., 1994. Oxidative DNA lesions as blocks to in vitro transcription by phage T7 RNA polymerase. Ann N Y Acad Sci 726, 346-348.

Henderson, D., Bielefeld, E. C., Harris, K. C., Hu, B. H., 2006. The role of oxidative stress in noise-induced hearing loss. Ear Hear 27, 1-19.

Huang, H., Das, R. S., Basu, A. K., Stone, M. P., 2011. Structure of (5'S)-8,5'-cyclo-2'-deoxyguanosine in DNA. J Am Chem Soc 133, 20357-20368.

Hu, B. H., Henderson, D., Nicotera, T. M., 2006. Extremely rapid induction of outer hair cell apoptosis in the chinchilla cochlea following exposure to impulse noise. Hear Res 211, 16-25.

Hu J J, Ambrus A, Fossum T W, Miller M W, Humphrey J D, Wilson E., 2008. Time courses of growth and remodeling of porcine aortic media during hypertension: a quantitative immunohistochemical examination. J Histochem Cytochem. 56: 359-370.

Kathe S D, Shen G P, Wallace S S., 2004. Single-stranded breaks in DNA but not oxidative DNA base damages block transcriptional elongation by RNA polymerase II in HeLa cell nuclear extracts. J Biol Chem. 279: 18511-18520.

Kenyon, J., Gerson, S. L., 2007. The role of DNA damage repair in aging of adult stem cells. Nucleic Acids Res 35, 7557-7565

Khanna K K, Jackson S P. 2001. DNA double-strand breaks: signaling, repair and the cancer connection. Nat Genet. 27: 247-254.

Koike M, Mashino M, Sugasawa J, Koike A., 2008. Histone H2AX phosphorylation independent of ATM after X-irradiation in mouse liver and kidney in situ. J Radiat Res. 49: 445-449.

Lamm, S., Sheng, Y., Pero, R. W., 2001. Persistent response to pneumococcal vaccine in individuals supplemented with a novel water soluble extract of *Uncaria tomentosa*, C-Med-100. Phytomedicine. 8, 267-274.

Lee, S. C., Bohne, B. A., Harding, G. W., 2008. Cochlear base-apex differences in cell death pathways following exposure to low-frequency noise. Otorhinolaryngol J 2, 29-43.

Le Prell, C. G., Yamashita, D., Minami, S. B., Yamasoba, T., Miller, J. M., 2007. Mechanisms of noise-induced hearing loss indicate multiple methods of prevention. Hear Res 226, 22-43.

Li C, Fan S, Owonikoko T K, Khuri F R, Sun S Y, Li R. 2011., Oncogenic role of EAPII in lung cancer development and its activation of the MAPK-ERK pathway. Oncogene, 30: 3802-3812.

Lomonaco, S. L., Xu, X. S., Wang, G., 2009. The role of Bcl-x(L) protein in nucleotide excision repair-facilitated cell protection against cisplatin-induced apoptosis. DNA Cell Biol 28, 285-294.

Lorito G, Giordano P, Prosser S, *Martini* A, Hatzopoulos S., 2006. Noise-induced hearing loss: a study on the pharmacological protection in the Sprague Dawley rat with N-acetyl-cysteine. Acta Otorhinolaryngol Ital. 26: 133-139.

Mammone T, Akesson C, Gan D, Giampapa V, Pero R W., 2006. A water soluble extract from *Uncaria tomentosa* (Cat's Claw) is a potent enhancer of DNA repair in primary organ cultures of human skin. Phytother Res. 20: 178-183.

Matkowskyj K A, Cox R, Jensen R T, Benya R V., 2003. Quantitative immunohistochemistry by measuring cumulative signal strength accurately measures receptor number. J Histochem Cytochem. 51:205-214.

Matkowskyj K A, Schonfeld D, Benya R V., 2000. Quantitative immunohistochemistry by measuring cumulative signal strength using commercially available software photoshop and matlab. J Histochem Cytochem. 48: 303-312.

Murai, N., Kirkegaard, M., Jarlebark, L., Risling, M., Suneson, A., Ulfendahl, M.,2008. Activation of JNK in the inner ear following impulse noise exposure. J Neurotrauma 25, 72-77.

Pero, R. W., Amiri, A., Sheng, Y., Welther, M., Rich, M., 2005. Formulation and in vitro/in vivo evaluation of combining DNA repair and immune enhancing nutritional supplements. Phytomedicine. 2005, 12, 255-263.

Pero R W, Giampapa V, Vojdani A., 2002. Comparison of a broad spectrum anti-aging nutritional supplement with and without the action of a DNA repair enhancing cat's claw extract. J Anti Aging Med. 5: 345-355.

Pero R W, Lund H, Leanderson T., 2009. Antioxidant metabolism induced by quinic acid. Increased urinary excretion of tryptophan and nicotinamide. Phytother Res. 23: 335-346.

Preston-Martin, S., Thomas, D. C., Wright, W. E., Henderson, B. E., 1989. Noise trauma in the aetiology of acoustic neuromas in men in Los Angeles County. Br J Cancer 59, 783-786.

Rogakou E P, Boon C, Redon C, Bonner W M. 1999. Megabase chromatin domains involved in DNA double-strand breaks in vivo. J Cell Biol. 146: 905-916.

Rogakou E P, Pilch D R, Orr A H, Ivanova V S, Bonner W M. 1998. DNA double-stranded breaks induce histone H2AX phosphorylation on serine 139. J Biol Chem. 273: 5858-5868.

Rothkamm K, Lobrich M. 2003. Evidence for a lack of DNA double-strand break repair in human cells exposed to very low x-ray doses. Proc Natl Acad Sci USA. 100: 5057-5062.

Redon C E, Nakamura A J, Martin O A, Parekh P R, Weyemi U S, Bonner W M. 2011. Recent developments in the use of γ-H2AX as a quantitative DNA double-strand break biomarker. Aging 3: 168-174.

Redon C E, Weyemi U, Parekh P R, Huang D, Burrell A S, Bonner W M. 2012. γ-H2AX and other histone post-translational modifications in the clinic. Biochim Biophys Acta. 1819:743-756.

Satou K, Hori M, Kawai K, Kasai H, Harashima H, Kamiya H., 2009. Involvement of specialized DNA polymerases in mutagenesis by 8-hydroxy-dGTP in human cells. DNA Repair (Amst). 8: 637-642.

Sheng Y, Akesson C, Holmgren K, Bryngelsson C, Giamapa V, Pero R W., 2005. An active ingredient of Cat's Claw water extracts identification and efficacy of quinic acid. J Ethnopharmacol. 96: 577-584.

Sheng Y, Bryngelsson C, Pero R W., 2000a. Enhanced DNA repair, immune function and reduced toxicity of C-MED-100, a novel aqueous extract from *Uncaria tomentosa*. J Ethnopharmacol. 69: 115-126.

Sheng Y, Li L, Holmgren K, Pero R W, 2001. DNA repair enhancement of aqueous extracts of *Uncaria tomentosa* in a human volunteer study. Phytomedicine, 8: 275-282.

Sheng Y, Pero R W, Wagner H., 2000b. Treatment of chemotherapy-induced leukopenia in a rat model with aqueous extract from *Uncaria tomentosa*. Phytomedicine, 7: 137-143.

Stiff T, O'Driscoll M, Rief N, Iwabuchi K, Lobrich M, Jeggo P A. 2004. ATM and DNA-PK function redundantly to phosphorylate H2AX after exposure to ionizing radiation. Cancer Res. 64: 2390-2396.

Taggart, R. T., McFadden, S. L., Ding, D. L., Henderson, D., Jin, X., Sun, W., Salvi, R., 2001. Gene Expression Changes in Chinchilla Cochlea from Noise-Induced Temporary Threshold Shift. Noise Health. 3, 1-18.

Van Campen, L. E., Murphy, W. J., Franks, J. R., Mathias, P. I., Toraason, M. A., 2002. Oxidative DNA damage is associated with intense noise exposure in the rat. Hear Res 164, 29-38.

Verma R, Rigatti M J, Belinsky G S, Godman C A, Giardina C., 2010. DNA damage response to the Mdm2 inhibitor nutlin-3. Biochem Pharmacol. 79, 565-574.

Wang C, Jurk D, Maddick M, Nelson G, Martin-Ruiz C, von Zglinicki T. 2009. DNA damage response and cellular senescence in tissues of aging mice. Aging Cell. 8: 311-323.

Wang, J., Ruel, J., Ladrech, S., Bonny, C., van de Water, T. R., Puel, J. L., 2007. Inhibition of the c-Jun N-terminal kinase-mediated mitochondrial cell death pathway restores auditory function in sound-exposed animals. Mol Pharmacol 71, 654-666.

Whitehead, M. L., Stagner, B. B., Lonsbury-Martin, B. L., Martin, G. K., 1995a. Effects of ear-canal standing waves on measurements of distortion-product otoacoustic emissions. J Acoust Soc Am. 98, 3200-3214.

Whitehead, M. L., Stagner, B. B., McCoy, M. J., Lonsbury-Martin, B. L., Martin, G. K., 1995b. Dependence of distortion-product otoacoustic emissions on primary levels in normal and impaired ears. II. Asymmetry in L1,L2 space. J Acoust Soc Am. 97, 2359-2377.

Whitehead, M. L., McCoy, M. J., Lonsbury-Martin, B. L., Martin, G. K., 1995c. Dependence of distortion-product otoacoustic emissions on primary levels in normal and impaired ears. I. Effects of decreasing L2 below L1. J Acoust Soc Am. 97, 2346-2358.

Wang X, Michaelis E K., 2010. Selective neuronal vulnerability to oxidative stress in the brain. Front Aging Neurosci., 2:12.

Yamashita, D., Miller, J. M., Jiang, H. Y., Minami, S. B., Schacht, J., 2004. AIF and EndoG in noise-induced hearing loss. Neuroreport 15, 2719-2722.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive. All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating hearing loss or deafness in a subject, the method comprising administering to said subject an effective amount of a composition comprising an aqueous extract derived from *Uncaria tomentosa* bark, thereby treating the hearing loss or deafness in the subject.

2. The method of claim 1, wherein the composition is formulated for administration selected from the group consisting of auricular, oral, parenteral, intraperitoneal, local, buccal, nasal, and topical administration.

3. The method of claim 1, wherein said composition is in the form of a liquid, tablet, or capsule.

4. The method of claim 1, wherein administration of the composition is effected during or after an insult that can damage the auditory system.

5. The method of claim 1, wherein the aqueous extract contains one or more carboxyl alkyl esters.

6. The method of claim 5, wherein the carboxy alkyl esters are selected from the group consisting of 3,4-O-dicaffeoylquinic acid, 3,5-O-dicaffeoylquinic acid, 1,3-O-dicaffeoylquinic acid, 4,5-O-dicaffeoylquinic acid, 1,5-O-dicaffeoylquinic acid, 3-O-feruloylquinic acid, 4-O-feruloylquinic acid, 5-O-feruloylquinic acid, 1-O-caffeoylquinic acid, 3-O-caffeoylquinic acid, 4-O-caffeoylquinic acid, 5-O-caffeoylquinic acid, (1S,3R,4R,5R)-3-[3-(3,4-dihydroxyphenyl)-3R-hydroxypropanoyl]-1,4,5-trihydroxycyclohexanecarboxylic acid, (1S,3R,4R,5R)-3-[3-(3,4 dihydroxyphenyl)-3S-hydroxypropanoyl]-1,4,5-trihydroxycyclohexanecarboxylic acid, (1S,3R,4R,5R)-5-[3-(3,4-dihydroxyphenyl) -3R-hydroxypropanoyl]-1,3,4-trihydroxycyclohexanecarboxylic acid, (1S,3R,4R,5R)-5-[3-(3,4-dihydroxyphenyl)-3S-hydroxypropanoyl]-1,3,4-trihydroxycyclohexanecarboxylic acid, (1S,3R,4R,5R)-4-[3-(3,4-dihydroxyphenyl)-3R-hydroxypropanoyl]-1,3,5-trihydroxycyclohexanecarboxylic acid, (1S,3R,4R,5R)-4-[3-(3,4-dihydroxyphenyl) -3S-hydroxypropanoyl]-1,3,5-trihydroxycyclohexanecarboxylic acid, cis-5-O-caffeoylquinic acid, 3-O-caffeoylquinic acid lactone, and 3-O-caffeoyl-4-O-feruloylquinic acid, or a pharmaceutically acceptable salt thereof.

7. The method of claim 1, wherein the composition further comprises one or more of an excipient, a preserving agent, a solubilizing agent, a stabilizing agent, a wetting agent, an emulsifier, a sweetener, a colorant, an odorant, a salt, a buffer, a coating agent, and an antioxidant.

8. A method of treating an auditory impairment in a subject, the method comprising administering to said subject an effective amount of a composition comprising an aqueous extract derived from *Uncaria tomentosa* bark, wherein the impairment was effected by an insult that can damage the auditory system, thereby treating the auditory impairment in the subject.

9. The method of claim 8, wherein the composition is formulated for administration selected from the group consisting of auricular, oral, parenteral, intraperitoneal, local, buccal, nasal, and topical administration.

10. The method of claim 8, wherein said composition is in the form of a liquid, tablet, or capsule.

11. The method of claim 8, wherein the auditory impairment is selected from a group consisting of hearing loss or deafness.

12. The method of claim 8, wherein the aqueous extract contains one or more carboxyl alkyl esters.

13. The method of claim 12, wherein the carboxy alkyl esters are selected from the group consisting of 3,4-O-dicaffeoylquinic acid, 3,5-O-dicaffeoylquinic acid, 1,3-O-dicaffeoylquinic acid, 4,5-O-dicaffeoylquinic acid, 1,5-O-dicaffeoylquinic acid, 3-O-feruloylquinic acid, 4-O-feruloylquinic acid, 5-O-feruloylquinic acid, 1-O-caffeoylquinic acid, 3-O-caffeoylquinic acid, 4-O-caffeoylquinic acid, 5-O-caffeoylquinic acid, (1S,3R,4R,5R)-3-[3-(3,4-dihydroxyphenyl)-3R-hydroxypropanoyl]-1,4,5-trihydroxycyclohexanecarboxylic acid, (1S,3R,4R,5R)-3-[3-(3,4 dihydroxyphenyl)-3S-hydroxypropanoyl]-1,4,5-trihydroxycyclohexanecarboxylic acid, (1S,3R,4R,5R)-5-[3-(3,4-dihydroxyphenyl) -3R-hydroxypropanoyl]-1,3,4-trihydroxycyclohexanecarboxylic acid, (1S,3R,4R,5R)-5-[3-(3,4-dihydroxyphenyl)-3S-hydroxypropanoyl]-1,3,4-trihydroxycyclohexanecarboxylic acid, (1S,3R,4R,5R)-4-[3-(3,4-dihydroxyphenyl)-3R-hydroxypropanoyl]-1,3,5-trihydroxycyclohexanecarboxylic acid, (1S,3R,4R,5R)-4-[3-(3,4-dihydroxyphenyl) -3S-hydroxypropanoyl]-1,3,5-trihydroxycyclohexanecarboxylic acid, cis-5-O-caffeoylquinic acid, 3-O-caffeoylquinic acid lactone, and 3-O-caffeoyl-4-O-feruloylquinic acid, or a pharmaceutically acceptable salt thereof.

14. The method of claim 8, wherein the composition further comprises one or more of an excipient, a preserving agent, a solubilizing agent, a stabilizing agent, a wetting agent, an emulsifier, a sweetener, a colorant, an odorant, a salt, a buffer, a coating agent, and an antioxidant.

15. The method of claim 1, wherein the composition comprises a single active agent consisting essentially of the aqueous extract derived from *Uncaria tomentosa* bark.

16. The method of claim 8, wherein the composition comprises a single active agent consisting essentially of the aqueous extract derived from *Uncaria tomentosa* bark.

* * * * *